US009024114B2

(12) United States Patent
Carlson et al.

(10) Patent No.: US 9,024,114 B2
(45) Date of Patent: May 5, 2015

(54) SOYBEAN EVENT 127 AND METHODS RELATED THERETO

(75) Inventors: Dale Carlson, Apex, NC (US); Francisco Jose Lima Aragao, Brasilia (BR); Carlos Alberto Arrabal Arias, Londrina (BR); Luiz Louzano, Santos (BR); Bruce M. Luzzi, Raleigh, NC (US); Tim Malefyt, Stoudsburg, PA (US); Elibio Leopoldo Rech Filho, Brasilia (BR); Siyuan Tan, Cary, NC (US); Adolfo Ulbrich, Londrina (BR); Tadashi Yotsumoto, San Paulo (BR); Ute Linemann, Gatersleben (DE)

(73) Assignees: Empresa Brasileira de Pesquisa Agropecuaria—Embrapa, Brasilia (BR); BASF Agrochemical Products B.V., Arnhem (NL)

( * ) Notice: Subject to any disclaimer, the term of this patent is extended or adjusted under 35 U.S.C. 154(b) by 833 days.

(21) Appl. No.: 13/143,491

(22) PCT Filed: Jan. 6, 2010

(86) PCT No.: PCT/US2010/020252
§ 371 (c)(1),
(2), (4) Date: Dec. 12, 2011

(87) PCT Pub. No.: WO2010/080829
PCT Pub. Date: Jul. 15, 2010

(65) Prior Publication Data
US 2012/0117676 A1 May 10, 2012

Related U.S. Application Data

(60) Provisional application No. 61/143,049, filed on Jan. 7, 2009.

(51) Int. Cl.
C12N 15/82 (2006.01)
A01H 5/00 (2006.01)
A01H 5/10 (2006.01)

(52) U.S. Cl.
CPC .............. *C12N 15/8275* (2013.01); *A01H 5/10* (2013.01)

(58) Field of Classification Search
None
See application file for complete search history.

(56) References Cited

U.S. PATENT DOCUMENTS

| 5,202,251 | A | 4/1993 | Singh et al. | |
| 6,225,105 | B1 | 5/2001 | Sathasivan et al. | |
| 2006/0174366 | A1* | 8/2006 | Andersson et al. | 800/278 |
| 2008/0320616 | A1 | 12/2008 | De Beuckeleer et al. | |

FOREIGN PATENT DOCUMENTS

| CN | 101151373 | 3/2008 |
| WO | WO 0185970 | 11/2001 |
| WO | WO 0220811 | 3/2002 |
| WO | WO 03/014357 | 2/2003 |
| WO | WO 2006/108674 | 10/2006 |
| WO | WO 2008/124495 | * 10/2008 |

OTHER PUBLICATIONS

Chang and Duggleby, "Herbicide-Resistant Forms of *Arabidopsis thaliana* Acetohydroxyacid Synthase: Characterization of the Catalytic Properties and Sensitivity to Inhibitors of Four Defined Mutants," Biochem. J., vol. 333, (1998), pp. 765-777.
Office Action, issued in corresponding Chinese Application No. 201080011786.7, dated Oct. 23, 2012.
Office Action, issued in corresponding Russian Application No. 2011133039, dated Oct. 17, 2013.
Office Action, issued in corresponding Singapore Application No. 201104983-0, dated Nov. 14, 2013.
Office Action, issued in corresponding Ukrainian Application No. 201109768, dated Mar. 17, 2014.
Office Action, issued in corresponding Chinese Application No. 201080011786.7, dated Jul. 2, 2013.
Office Action, issued in corresponding Chinese Application No. 201080011786.7, dated Jan. 20, 2014.
International Preliminary Report on Patentability, issued in PCT/US2010/020252, dated Jul. 12, 2011.
International Search Report, issued in PCT/US2010/020252, dated May 31, 2010.
Tan et al., "Herbicidal Inhibitors of Amino Acid Biosynthesis and Herbicide-Tolerant Crops," Amino Acids, vol. 30, No. 2, (Mar. 1, 2006), pp. 195-204.
Terry et al., "Event-Specific Detection and Roundup Ready Soya using Two Different Real Time PCR Detection Chemistries," European Food Research and Technology, vol. 213, No. 6, (Nov. 1, 2001), pp. 425-431.
Windels et al., "Characterisation of the Roundup Ready Soybean Insert," European Food Research and Technology, vol. 213, No. 2, (Aug. 1, 2001), pp. 107-112.

* cited by examiner

*Primary Examiner* — David H Kruse
(74) *Attorney, Agent, or Firm* — Armstrong Teasdale LLP

(57) ABSTRACT

Compositions and methods related to transgenic AHAS-inhibiting herbicide resistant soybean plants are provided. Event 127 soybean plants having a mutated AHAS coding sequence which imparts tolerance to an AHAS-inhibiting herbicide are provided. The event 127 soybean plants having the event 127 nucleic acid molecule at the identified chromosomal location may comprise genomic/transgene junctions having at least the nucleic acid sequence of SEQ ID NO: 5 and/or 6. The characterization of the genomic insertion site of the event 127 provides for an enhanced breeding efficiency and enables the use of molecular markers to track the transgene insert in the breeding populations and progeny thereof. Various methods and compositions for the identification, detection, and use of the event 127 soybean plants are provided.

35 Claims, 19 Drawing Sheets

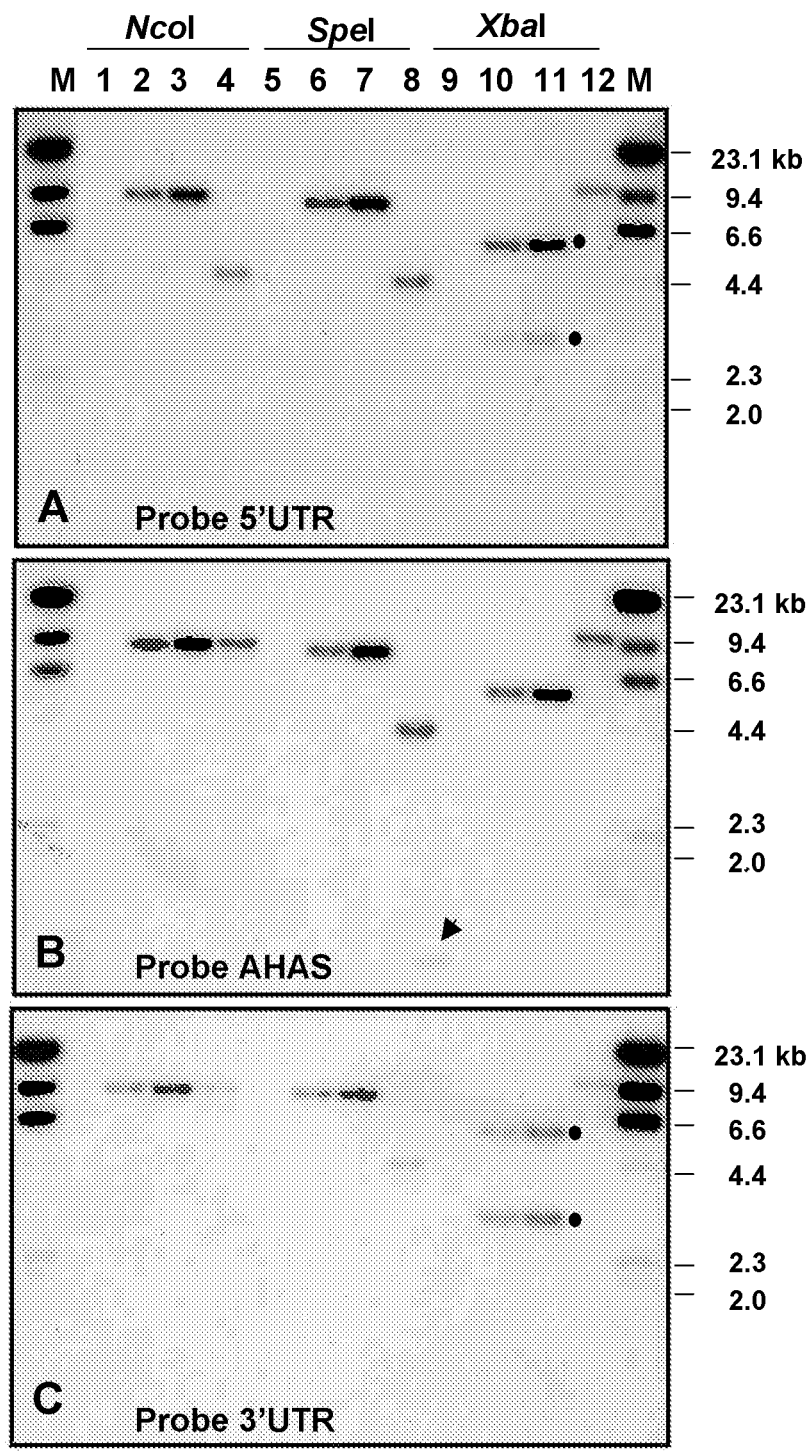
FIGURE 4A-C

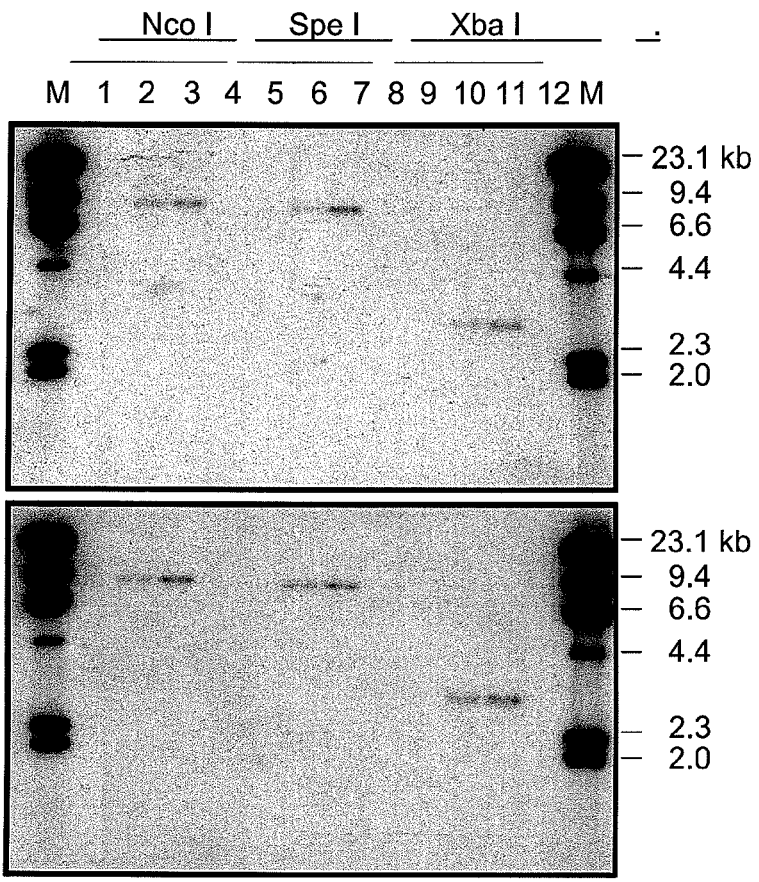
FIGURE 5A
FIGURE 5B
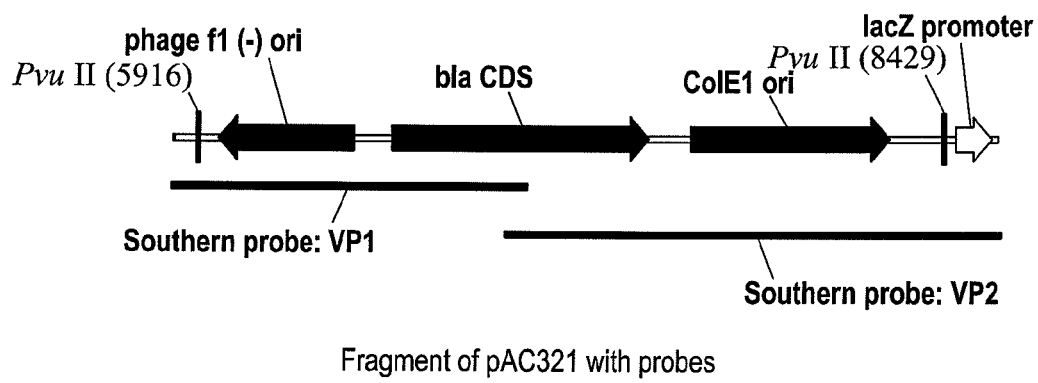
Fragment of pAC321 with probes
FIGURE 5C

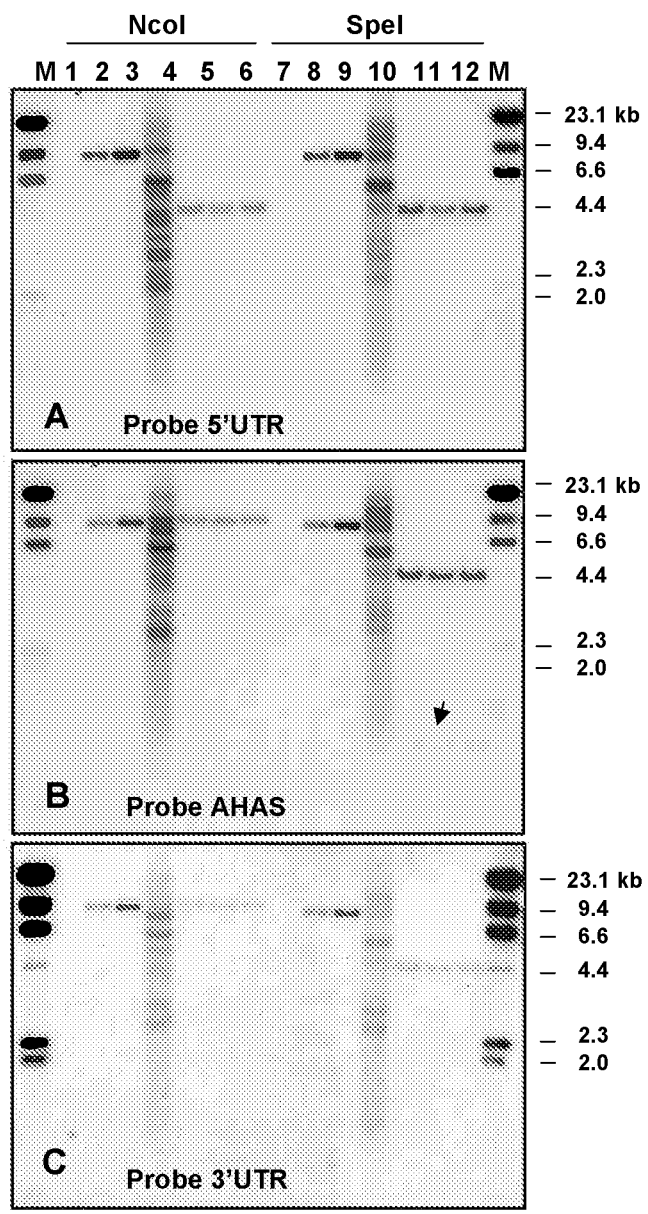
FIGURE 6A-C

Figure 8A

```
   1 gtgagactcc aacagcaaga gtcactttgt agcccactca aataaatgtg
  51 aacattaata ggtggatttg gacaatacag gcccttgtt ttaacaaggt
 101 cttgcagttt cacttaaaaa ttcatagtag ttagaagaac taatattatg
 151 tgccaactga caataaaaga aaaacaatc tttccaattt atattacaca
 201 taagacacag cctgaaaaaa gaagagagca tgtatctgta aacaagttag
 251 gcatgatgcc aaaggagcag cagcataaca aaacaaacga aaattacaag
 301 aaaatatggc ttaccagcat ggttgctggg aaggactgga tcaagaagtg
 351 agcggcaatc aacaagtgtt actacagcat acttttctct ttgataatca
 401 ggaaggcatc tagaggtcca tgcagcaatc attccagctg cagcaagtgc
 451 cccacaaagt ttgatccctc ttgatttgca tccctacatg atcttgcata
 501 attagcttaa acccatcaag ctagctacca gatcataagc aaaaagtgag
 551 cagagtgcca tatcaattat tcacagaaat tagattataa cacattggat
 601 gcataagaat gaatttcaat tacaaatacg cagagacaaa aaagaagata
 651 atgtgacatt gaggctgctt tgtaccagga aaaataatag cagctgatat
 701 tattagttat aattggctgc aaatttctcc aaattgtaaa tatgaatttc
 751 attaatcact ttatttagct gataaatcca attgatatta taaagagttt
 801 ggatcaaacc atagggctgt gacctgtgaa acacaaactc ctcattcgta
 851 ttagaggctc taccctccta atagctttgg ctttactgtc ttattgacta
 901 tctttgtaaa tgtcttacaa agactaatga cttctccaca atgtgccaat
 951 taagtttatc tttttttgaaa aataaatggc tggtatcttc atcccttaag
1001 aaaataggaa gtttaggctt gaaaatagag attgcaatag gcaagattaa
1051 tttagggcgt gtttgggaaa aagttgcatc caacattctc tttaattcag
1101 tacaagagct ccttcgccgt ttagtgtata ggaaagcgca aactgatgtt
1151 tggaagcttg aaacggcaat aaaatatcaa aatctttata ttaaagctga
1201 acaaaagggg ccctccttat ttatcccctt agttttttatt ttcatttctt
1251 tctaataaag gggcaaacta gtctcgtaat atattagagg ttaattaaat
1301 ttatattcct caaataaaac ccaattttca tccttaaacg aacctgctga
1351 aaccctaatt tcgattacca attccgatct aaaagaagt catggaagcc
1401 attgattccg caatcgatcc tctcagagat ttcgctaaga gcagtgttcg
1451 tctcgtccag cgctgtcaca aacccgatcg caagggtaac gccttttctc
1501 aaaaaaatct catttccgat ttttgatctg tagattaggg ttttctgaaa
1551 ttttgatatc atttgtaatt gaattggtta tcagaattca cgaaagtagc
1601 tgtgcgtacg gcgattggat ttgtggtgat gggattcgtt ggattcttcg
1651 tgaagctcgt tttcatccca atcaacaaca tcatcgttgg atcttcttag
1701 tgtagtactt tctttacgag gtaattgatc tcgcattata tatctacatt
1751 ttggttatgt tacttgacat atagtcattg attcaatagt tctgttaatt
1801 cctttaaaga tcatttgac tagaccacat tcttggttca ttcctcaata
1851 atttgtaatc atattggtgg atatagaagt agattggtta tagatcagat
1901 agtggaagac tttaggatga atttcagcta gtttttttt ttggcttatt
1951 gtctcaaaag attagtgctt tgctgtctcc attgcttctg ctatcgacac
2001 gcttctgtct ccttgtatct ttattatatc tattcgtccc atgagttttg
2051 tttgttctgt attcgttcgc tctggtgtca tggatggagt ctctgttcca
2101 tgtttctgta atgcatgttg ggttgtttca tgcaagaaat gctgagataa
2151 acactcattt gtgaaagttt ctaaactctg aatcgcgcta caggcaatgc
2201 tccgaggagt aggaggagaa gaacgaacca aacgacatta tcagcccttt
2251 gaggaagctc ttagttttgt tattgttttt gtagccaaat tctccattct
2301 tattccattt tcacttatct cttgttcctt atagacctta taagtttttt
2351 attcatgtat acaaattata ttgtcatcaa gaagtatctt taaaatctaa
2401 atctcaaatc accaggacta tgtttttgtc caattcgtgg aaccaacttg
2451 cagcttgtat ccattctctt aaccaataaa aaaagaaaga aagatcaatt
2501 tgataaattt ctcagccaca aattctacat ttaggtttta gcatatcgaa
2551 ggctcaatca caaatacaat agatagacta gagattccag cgtcacgtga
```

Figure 8B

```
2601 gttttatcta taaataaagg accaaaaatc aaatcccgag ggcattttcg
2651 taatccaaca taaaacccdt aaacttcaag tctcattttt aaacaaatca
2701 tgttcacaag tctcttcttc ttctctgttt ctctatctct tgctcatctt
2751 tctcctgaac catggcggcg gcaacaacaa caacaacaac atcttcttcg
2801 atctccttct ccaccaaacc atctccttcc tcctccaaat caccattacc
2851 aatctccaga ttctccctcc cattctccct aaacccaac aaatcatcct
2901 cctcctcccg ccgccgcggt atcaaatcca gctctccctc ctccatctcc
2951 gccgtgctca acacaaccac caatgtcaca accactccct ctccaaccaa
3001 acctaccaaa cccgaaacat tcatctcccg attcgctcca gatcaacccc
3051 gcaaaggcgc tgatatcctc gtcgaagctt tagaacgtca aggcgtagaa
3101 accgtattcg cttaccctgg aggtgcatca atggagattc accaagcctt
3151 aacccgctct tcctcaatcc gtaacgtcct tcctcgtcac gaacaaggag
3201 gtgtattcgc agcagaagga tacgctcgat cctcaggtaa accaggtatc
3251 tgtatagcca cttcaggtcc cggagctaca aatctcgtta gcggattagc
3301 cgatgcgttg ttagatagtg ttcctcttgt agcaatcaca ggacaagtcc
3351 ctcgtcgtat gattggtaca gatgcgtttc aagagactcc gattgttgag
3401 gtaacgcgtt cgattacgaa gcataactat cttgtgatgg atgttgaaga
3451 tatccctagg attattgagg aagctttctt tttagctact tctggtagac
3501 ctggacctgt tttggttgat gttcctaaag atattcaaca acagcttgcg
3551 attcctaatt gggaacaggc tatgaaatta cctggttata tgtctaggat
3601 gcctaaacct ccggaagatt ctcatttgga gcagattgtt aggttgattt
3651 ctgagtctaa gaagcctgtg ttgtatgttg gtggtggttg tttgaattct
3701 agcgatgaat tgggtaggtt tgttgagctt acggggatcc ctgttgcgag
3751 tacgttgatg gggctgggat cttatccttg tgatgatgag ttgtcgttac
3801 atatgcttgg aatgcatggg actgtgtatg caaattacgc tgtggagcat
3851 agtgatttgt tgttggcgtt tggggtaagg tttgatgatc gtgtcacggg
3901 taagcttgag gcttttgcta gtagggctaa gattgttcat attgatattg
3951 actcggctga gattgggaag aataagactc ctcatgtgtc tgtgtgtggt
4001 gatgttaagc tggctttgca agggatgaat aaggttcttg agaaccgagc
4051 ggaggagctt aagcttgatt ttggagtttg gaggaatgag ttgaacgtac
4101 agaaacagaa gtttccgttg agctttaaga cgtttgggga agctattcct
4151 ccacagtatg cgattaaggt ccttgatgag ttgactgatg gaaaagccat
4201 aataagtact ggtgtcgggc aacatcaaat gtgggcggcg cagttctaca
4251 attacaagaa accaaggcag tggctatcat caggaggcct tggagctatg
4301 ggatttggac ttcctgctgc gattggagcg tctgttgcta accctgatgc
4351 gatagttgtg gatattgacg gagatggaag ctttataatg aatgtgcaag
4401 agctagccac tattcgtgta gagaatcttc cagtgaaggt acttttatta
4451 aacaaccagc atcttggcat ggttatgcaa tgggaagatc ggttctacaa
4501 agctaaccga gctcacacat ttctcgggga tccggctcag gaggacgaga
4551 tattcccgaa catgttgctg tttgcagcag cttgcgggat tccagcggcg
4601 agggtgacaa agaaagcaga tctccgagaa gctattcaga caatgctgga
4651 tacaccagga ccttacctgt tggatgtgat ttgtccgcac caagaacatg
4701 tgttgccgat gatcccgaat ggtggcactt tcaacgatgt cataacggaa
4751 ggagatggcc ggattaaata ctgagagatg aaaccggtga ttatcagaac
4801 cttttatggt ctttgtatgc atatggtaaa aaaacttagt ttgcaatttc
4851 ctgtttgttt tggtaatttg agtttctttt agttgttgat ctgcctgctt
4901 tttggtttac gtcagactac tactgctgtt gttgtttggt ttcctttctt
4951 tcattttata aataaataat ccggttcggt ttactccttg tgactggctc
5001 agtttggtta ttgcgaaatg caaatggtaa attgagtaat tgaaattcgt
5051 tattagggtt ctaacctgtt ttaacagtca ctgggttaat atctctcgaa
5101 tcttgcatgg aaaatgctct taccattggt ttttaattga aatgtgctca
5151 tatgggccgt ggtttccaaa ttaaataaaa ctacgatgtc atcgagaagt
5201 aaaatcaact gtgtccacat tatcagtttt gtgtatacga tgaaataggg
5251 taattcaaaa tctagcttga tatgcctttt ggttcatttt aaccttctgt
5301 aaacattttt tcagattttg aacaagtaaa tccaaaaaaa aaaaaaaaaa
```

Figure 8C

```
5351 atctcaactc aacactaaat tattttaatg tataaaagat gcttaaaaca
5401 tttggcttaa aagaaagaag ctaaaaacat agagaactct tgtaaattga
5451 agtatgaaaa tatactgaat tgggtattat atgaattttt ctgatttagg
5501 attcacatga tccaaaaagg aaatccagaa gcactaatca gacattggaa
5551 gtaggaatat ttcaaaaagt ttttttttttt taagtaagtg acaaaagctt
5601 ttaaaaaata gaaagaaac tagtattaaa gttgtaaatt taataaacaa
5651 aagaaatttt ttatatttttt tcatttctttt ttccagcatg agggatctta
5701 tccttgtgat gatgagttgt cgttacatat gcttggaatg catgggactg
5751 tgtatgcaaa ttacgctgtg gagcatagtg atttgttgtt ggcgtttgga
5801 gtaaggtttg atgatcgtgt cacgggtaag cttgaggctt ttgctagtag
5851 ggctaagatt gttcatattg atattgactc ggctgagatt gggaagaata
5901 agactcctca tgtgtctgtg tgtggtgatg ttaagctggc tttgcaaggg
5951 atgaataagg ttcttgagaa ccgagcggag gagcttaagc ttgattttgg
6001 agtttggagg aatgagttga acgtacagaa acagaagttt ccgttgagct
6051 ttaagacgtt tggggaagct gtcccatgcc catcaaagaa gacagtacac
6101 gatccgagct acgaatgggt aggcccaata aggcgagaag ggccacccag
6151 tccaatgagg gaagacaaac taacacaaaa tacccatcta ataaggacct
6201 ataagtttgt atttttttaaa tgtatttgaa aaattcaaac aattttttaat
6251 tgttaatttt ttttcctaaa attaaacaaa catatttttg tagaagcaaa
6301 gatatcataa tgttttgatg atgctaaaga aacacgcttc tcaagtttga
6351 tccaaaataa aactctaaga aattcaagat aaatgataaa gttagtctat
6401 agagtcttag aaagaagttt ctaaattgat gatgcataag ttatgaccaa
6451 aggttttttc tcaaaagctt ttaaaagaga tatttattct ctgataatca
6501 attactagtg acaaaaatgt ttactggaat gctttaaaat gttttttaata
6551 ttttgaaagc ttgtaatcga ttacacaaga cttgtaatcg attaccaaaa
6601 gttttgaaca ttttaagaca acctttagaa atttgaattt aaatttcaaa
6651 gtctgtaatc gattaccaga attaaaatta aaattttaga tgtgaagagt
6701 caaaagtctt cagaaaacaa ttgtgtaatc gattacacca ttttggtaat
6751 cgattaccac tgagaaattt tctaaaatat ctccgaacag ttacatcttt
6801 tcaaatgatt ttgaatgacc attaaaggct tatatataag tgacttggga
6851 catgaatttt cagagagttt ttctgaactg aaatgtttta tcctctcaaa
6901 aatgattcct tggtctaaca cttgcatatt taataaagaa tcttgattga
6951 tcttcaattg taatatcctt cttttaaaga gagaaacttc ttcttcttct
7001 tattcaaagg aaattgttta agagaccgag gatctcttaa atggtaagga
7051 ttcctgaaca caatggaagg attatccttg tgtgattcag actttgtaaa
7101 aggggttttt acaaagagag tggaaaatct caagtgggtt gcttgagtga
7151 ggacttgacg taggcatgaa aaatggctga accagtataa attaagttta
7201 catttctctc ttcccttaac cttcttttat ttattgttat ttatctttta
7251 ttttaaaaaa gtttattttg aattgtcttt tgagtaattc atattaatgg
7301 tgcattgtta attcaaaaaa agagtggaat tttaattgag aaatagtttt
7351 tgtatcttaa ttcaatcccc ttttcttaag ataactgaga tcacttgtct
7401 aacaattttg tgtataatta cattcaataa ttttttttagt taatatctta
7451 aatatataaa ttccaaactc ttgaaattaa aaaaatatgc ataatttatt
7501 taataaattt aaatttttagg aaaaaaagtt aagggggtcat taaatttgat
7551 aaaaagttaa gaatattatt gaattttata atttttttta tagaaaatag
7601 tgaaaacaat aaaagttttt ttctatttct taacaaccct ttcaataaaa
7651 aaatgaaatg aaaataatat gacatttta taattaagag taatataaaa
7701 ataaaataaa ataattttaa accaaaggac tcataagcat gttattgctc
7751 taccactcat aaaaatttttt ctcctattat cttttttgatg ataaaatatt
7801 gtcatactag aaataaaata tatttttttct atatcctcta tatgagtcaa
7851 tcttatttta agtacaatgt tactgaaagt cattttgcaa taaaaatctt
7901 ccaagatttt tcccaaacaa ttgttgtaat tttagttctt taaaatatac
7951 atataaaaat gcattatttg tatggtataa tataaataat agaaacaata
8001 tcaacatttc tcattgagta ttgagaagct aaagtaaatt acttgactac
8051 attgccgtag tgcgacgaat tagattgtaa tatctaaaat acttaagtag
```

Figure 8D

```
 8101 tgtagataag tctatgaatg tttttcagat taattgcacg ataatttttt
 8151 ttaattctac tataattcca tatttatttg aaaaacttca tgataacatg
 8201 catcctttat ttattacatt aaccttctta aatatttcaa atatcacgtt
 8251 tcactgcaag aaaagtttta taatctttaa taagcttcat acatgctcgt
 8301 accttcccac aataagccaa tttgggtctg ccaatgtcct cactcttgaa
 8351 aaaggaaaat ataaacctca aagtgatcat gtgatatgat aaaaatttaa
 8401 aaatatataa attcatagag aaaaaaagga atgaaaatga attgtaagaa
 8451 agtgaaatgt atgaaaatct gaactcattc aaaatcatat aagaaaataa
 8501 accgtggaag aaaacgagca tcacattcac ataacatgtt ctgctccaac
 8551 actaattatt ctgctaccgc agatatagca accagagtgg ccattttatt
 8601 acatttgtat cgatccatgc atttacgtac actccatcta gctaaacatc
 8651 atatcactac taacatgaca caaaataagg aaaaaactca gaatgtcagc
 8701 ttgaagttta atagatttcc tcctttaata acatttaaat atgatttatt
 8751 tttataataa aaatatcttt aaaaatattt atttagtagt tattttagc
 8801 ataaatatta ggaattgata cttttcttat ttatgacttg cagatataaa
 8851 aatgaagaat taaaagtaaa gaaaatccaa aaaatatcaa aaatataaat
 8901 aaggaagatt ttttggcgtc agacccaagt tcattccaac agctgtaatt
 8951 ttttcagatt aaaaaggatg aatgatgaat gaaattaaaa gtaagaaagg
 9001 aataaagaca caccgagtct cggagcaatc taatacacac ctaaagcctg
 9051 agaactctcc cttaggaaat tccttcttct ctttcatcat tctttatttc
 9101 cttttccat ctcttctctt ccatcagttc gtatatccct ttgctagtgt
 9151 aaaccccctt atggttatga gaggctaaac ccttagttag ggtttgacag
 9201 gcttaaaaag tcaaagatg tattatacac ttcatattta tcaatgcaaa
 9251 cagatgtttt ctttcctatt atccttctt atttctaatt tcatgcatca
 9301 ttcatccttg cattatcttt ggggttagg tgctcgacaa aggataatcc
 9351 caaagaaggt tttgcatgta tctatttcag gaattagtcg ctcgacagag
 9401 agtaatttct aataaaacta aaagaagaa atatcttaat aaaatcattg
 9451 ttagacataa aatgattgta ttatgcccat gcatcaaagc aaacatatag
 9501 aattataact tcatgtattt tatctattgg ctctttgcaa aaacatttgg
 9551 aagatagata ggtaaaatag gtgagacatc aggtatttta atagatgtga
 9601 gtaagataaa ttcacctgat agagaaaatc ataaataata tatcttagac
 9651 aaataagaca tgctaggtcc taacattttc atcccattga attcactatt
 9701 ttttcttttg ttatttagta ataattatta ttttatactc tgttcttta
 9751 aaattatctt ttatacctat cttatatttt tctcttataa attaaaaatt
 9801 atccaacaca aatacaaaac aaagttaaaa tcgacactca agacttccga
 9851 gttttgatc aaaaagcctt tctatctttc ctcttgcggt ctgctccatt
 9901 ttagaagaaa aggaaccaat taataaaatg gacagcgcaa tcaaataagt
 9951 aaaaatttac ttaatataat gatgcatgat agctagaagg gtaccaataa
10001 tttaaccctg atcaataacg tcaatagaga ctctccccaa accccaaatt
10051 agggtatcgc tgatccttat gaaaaccccg aaataaataa attgaaagga
10101 accctaaacg cgaaaccta tatttgcatc gtggaagcgc agaaaacttc
10151 actgagataa atgaagtcgg atagaacata gattctcgta gatcatccat
10201 cacaaaccct aaaagaagta ttagattttc gcgttcggag aaacaaacct
10251 gagtggtaga aacgaagctt gatttgttgg aacgattgtt gagagaaaga
10301 acagagagca aaataaggct tctattttct taatcaaacg ttggtgtttg
10351 ttgccaatgt tgtgttaggc ttatttataa tttctctgtt agcttgtaaa
10401 gcacgcaaca ataagatgag atataggatt tttttttat tttaaaaaaa
10451 aagacatttg ccgtcatata aggataaatt aaggcttaaa aaaagatagt
10501 tatttctttt aaaaaaataa ttatttctga aatttaatat tttgaagata
10551 gtttgaattt acttatgaaa atatttgttt tgagtttcaa tttataaaat
10601 catttctagt gtgggaagtt acatttcgtt tggattagaa attttaaaat
10651 tctaga
```

Figure 12A ctggcacgacaggtttcccgactggaaagcgggcagtgagcgcaacgcaattaatgtgagttagctcactcattaggcacc
ccaggctttacactttatgcttccggctcgtatgttgtgtggaattgtgagcggataacaatttcacacaggaaacagctatga
ccatgattacgccaagctcgaaattaaccctcactaaagggaacaaaagctggagctccaccgcggtggcggccgctcta
gattatgtatttccaactttcattaacaatataatcgcatataaatgaaaaatcgtttccaggataatattttgatgaaatctcatatt
attgttcgtactcggattgatgttgaaggcttgaagcgcttcaaattatagaccagattatttaagtttttcttttgtttactccatatc
aatttgatccattatactacctaagaaaatttaggtaacatagaattatttattgttatagtaaaaaaaaggaaaaccacaaaaat
aatctacttttacgtatatactattttcatgacataagtaattaagttgtacaacttttttttaatgaaaagagagagtaaatttatcat
gttcatgtgtagttacctcgtgaataaccgacggttatatagacgcctaacatgaattgttcagttgaagacagttcaaaacatg
tgtttcactctaaaatcctcaacaaaaaaaaagtgttaaaatttgtaaacctctttcaagcaaaaaaagaaaaagtgttagaatc
ccaagattctttcataatccggaatcttggctgaaaacgtataaaagagattgacgtagtaacaaggagtcttggtatgcttcc
atgcttttatcctttttgtcatggaaccatgatttggttaccatttattatgtaaccgaaattttcattgtaataatgaatatttaaattt
ttagcaaaaaaaaacaaaaaaaaacaaggagtcttgtcttcgttctcaaatttcagagctcttgcacttttcaagagttttacttt
gatgagtgagacatttgtcttttagtgtttattttctaaacttaaaatagtagcatcaacatcactcaattataattcttaagatgttg
tagaaaaatattttatagatggaaagtaatcgatattaagacaaataagaaaccaaaccggactttgtgttcagaccgaatcaa
atctgaattggagaaattatggtggaggcgaaagtcaacggaactaaagtataaaaccaaatgtcaaaaataaaacccaatt
ttcatccttaaacgaacctgctgaaaccctaatttcgattaccaattccgatctaaaaagaagtcatggaagccattgattccgc
aatcgatcctctcagagatttcgctaagagcagtgttcgtctcgtccagcgctgtcacaaacccgatcgcaagggtaacgcc
ttttctcaaaaaaatctcatttccgattttgatctgtagattagggttttctgaaattttgatatcatttgtaattgaattggttatcag
aattcacgaaagtagctgtgcgtacggcgattggatttgtggtgatgggattcgttggattcttcgtgaagctcgttttcatccc
aatcaacaacatcatcgttggatcttcttagtgtagtactttcttacgaggtaattgatctcgcattatatatctacattttggttatg
ttacttgacatatagtcattgattcaatagttctgttaattcctttaaagatcattttgactagaccacattcttggttcattcctcaat
aatttgtaatcatattggtggatatagaagtagattggttatagatcagatagtggaagactttaggatgaatttcagctagtttttt
tttttggcttattgtctcaaaagattagtgctttgctgtctccattgcttctgctatcgacacgcttctgtctccttgtatctttattatat
ctattcgtcccatgagttttgtttgttctgtattcgttcgctctggtgtcatggatggagtctctgttccatgtttctgtaatgcatgtt
gggttgtttcatgcaagaaatgctgagataaacactcatttgtgaaagtttctaaactctgaatcgcgctacaggcaatgctcc
gaggagtaggaggagaagaacgaaccaaacgacattatcagcccctttgaggaagctcttagttttgttattgtttttgtagcca
aattctccattcttattccattttcacttatctcttgttccttatagaccttataagttttttattcatgtatacaaattatattgtcatcaag
aagtatctttaaaatctaaatctcaaatcaccaggactatgttttttgtccaattcgtggaaccaacttgcagcttgtatccattctct
taaccaataaaaaaagaaagaaagatcaatttgataaatttctcagccacaaattctacatttaggttttagcatatcgaaggct
caatcacaaatacaatagatagactagagattccagcgtcacgtgagttttatctataaataaaggaccaaaaatcaaatccc
gagggcatttctgtaatccaacataaaacccttaaacttcaagtctcatttttaaacaaatcatgttcacaagtctcttcttcttctc
tgtttctctatctcttgctcatctttctcctgaaccatggcggcggcaacaacaacaacaacaacatcttcttcgatctccttctcc
accaaaccatcctccttcctcctccaaatcaccattaccaatctccagattctccctcccattctccctaaaccccaacaaatcat
cctcctcctcccgccgccgcggtatcaaatccagctctccctcctccatctccgccgtgctcaacacaaccaccaatgtcac
aaccactccctctccaaccaaacctaccaaacccgaaacattcatctcccgattcgctccagatcaaccccgcaaaggcgc
tgatatcctcgtcgaagctttagaacgtcaaggcgtagaaaccgtattcgcttaccctggaggtgcatcaatggagattcacc
aagccttaacccgctcttcctcaatccgtaacgtccttcctcgtcacgaacaaggaggtgtattcgcagcagaaggatacgc
tcgatcctcaggtaaaccaggtatctgtatagccacttcaggtcccggagctacaaatctcgttagcggattagccgatgcgt
tgttagatagtgttcctcttgtagcaatcacaggacaagtccctcgtcgtatgattggtacagatgcgtttcaagagactccgat
tgttgaggtaacgcgttcgattacgaagcataactatcttgtgatggatgttgaagatatccctaggattattgaggaagctttct
ttttagctacttctggtagacctggacctgttttggttgatgttcctaaagatattcaacaacagcttgcgattcctaattgggaac
aggctatgagattacctggttatatgtctaggatgcctaaacctccggaagattctcatttggagcagattgttaggttgatttct
gagtctaagaagcctgtgttgtatgttggtggtggttgtttgaattctagcgatgaattgggtaggtttgttgagcttacggggat
ccctgttgcgagtacgttgatggggctgggatcttatccttgtgatgatgagttgtcgttacatatgcttggaatgcatgggact
gtgtatgcaaattacgctgtggagcatagtgatttgttgttggcgtttggggtaaggtttgatgatcgtgtcacgggtaagcttg
aggcttttgctagtagggctaagattgttcatattgatattgactcggctgagattgggaagaataagactcctcatgtgtctgt
gtgtggtgatgttaagctggctttgcaagggatgaataaggttcttgagaaccgagcggaggagcttaagcttgattttggag
tttggaggaatgagttgaacgtacagaaacagaagtttccgttgagctttaagacgtttggggaagctattcctccacagtatg

Figure 12B cgattaaggtccttgatgagttgactgatggaaaagccataataagtactggtgtcgggcaacatcaaatgtgggcggcgc
agttctacaattacaagaaaccaaggcagtggctatcatcaggaggccttggagctatgggatttggacttcctgctgcgatt
ggagcgtctgttgctaaccctgatgcgatagttgtggatattgacggagatggaagctttataatgaatgtgcaagagctagc
cactattcgtgtagagaatcttccagtgaaggtacttttattaaacaaccagcatcttggcatggttatgcaatgggaagatcg
gttctacaaagctaaccgagctcacacatttctcggggatccggctcaggaggacgagatattcccgaacatgttgctgtttg
cagcagcttgcgggattccagcggcgagggtgacaaagaaagcagatctccgagaagctattcagacaatgctggatac
accaggaccttacctgttggatgtgatttgtccgcaccaagaacatgtgttgccgatgatcccgaatggtggcactttcaacg
atgtcataacggaaggagatggccggattaaatactgagagatgaaaccggtgattatcagaacctttatggtctttgtatgc
atatggtaaaaaaacttagtttgcaatttcctgtttgttttggtaatttgagtttcttttagttgttgatctgcctgcttttggtttacgt
cagactactactgctgttgttgtttggtttcctttctttcattttataaataaataatccggttcggtttactccttgtgactggctcag
tttggttattgcgaaatgcgaatggtaaattgagtaattgaaattcgttattagggttctaagctgttttaacagtcactgggttaat
atctctcgaatcttgcatggaaaatgctcttaccattggttttaattgaaatgtgctcatatgggccgtggtttccaaattaaata
aaactacgatgtcatcgagaagtaaaatcaactgtgtccacattatcagttttgtgtatacgatgaaatagggtaattcaaaatc
tagcttgatatgccttttggttcattttaaccttctgtaaacattttttcagattttgaacaagtaaatccaaaaaaaaaaaaaaaaa
atctcaactcaacactaaattattttaatgtataaaagatgcttaaaacatttggcttaaaagaaagaagctaaaaacatagaga
actcttgtaaattgaagtatgaaaatatactgaattgggtattatatgaattttctgatttaggattcacatgatccaaaaaggaa
atccagaagcactaatcagacattggaagtaggaatatttcaaaaagttttttttttttaagtaagtgacaaaagcttttaaaaaat
agaaaagaaactagtattaaagttgtaaatttaataaacaaaagaaatttttatattttttcatttcttttccagcatgaggttatga
tggcaggatgtggatttcattttttttccttttgatagccttttaattgatctattataattgacgaaaaaatattagttaattatagatat
attttaggtagtattagcaatttacacttccaaaagactatgtaagttgtaaatatgatgcgttgatctcttcatcattcaatggtta
gtcaaaaaaataaaagcttaactagtaaactaaagtagtcaaaaattgtactttagtttaaaatattacatgaataatccaaaac
gacatttatgtgaaacaaaaacaatatctagaactagtggatcccccgggctgcaggaattcgatatcaagcttatcgatacc
gtcgacctcgagggggggcccggtacccaattcgccctatagtgagtcgtattacaattcactggccgtcgttttacaacgtc
gtgactgggaaaaccctggcgttacccaacttaatcgccttgcagcacatccccctttcgccag

SEQUENCE LISTING

```
<160> NUMBER OF SEQ ID NOS: 70

<210> SEQ ID NO 1
<211> LENGTH: 10656
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gtgagactcc aacagcaaga gtcactttgt agcccactca aataaatgtg aacattaata      60
ggtggatttg gacaatacag gcccttgtt ttaacaaggt cttgcagttt cacttaaaaa     120
ttcatagtag ttagaagaac taatattatg tgccaactga caataaaaga aaaaacaatc     180
tttccaattt atattacaca taagacacag cctgaaaaaa gaagagagca tgtatctgta     240
aacaagttag gcatgatgcc aaaggagcag cagcataaca aaacaaacga aaattacaag     300
aaaatatggc ttaccagcat ggttgctggg aaggactgga tcaagaagtg agcggcaatc     360
```

```
aacaagtgtt actacagcat acttttctct ttgataatca ggaaggcatc tagaggtcca    420
tgcagcaatc attccagctg cagcaagtgc cccacaaagt ttgatccctc ttgatttgca    480
tccctacatg atcttgcata attagcttaa acccatcaag ctagctacca gatcataagc    540
aaaaagtgag cagagtgcca tatcaattat tcacagaaat tagattataa cacattggat    600
gcataagaat gaatttcaat tacaaatacg cagagacaaa aagaagata atgtgacatt     660 gaggctgctt tgtaccagga aaataatag cagctgatat tattagttat aattggctgc     720
aaatttctcc aaattgtaaa tatgaatttc attaatcact ttatttagct gataaatcca    780
attgatatta taaagagttt ggatcaaacc atagggctgt gacctgtgaa acacaaactc    840
ctcattcgta ttagaggctc taccctccta atagctttgg ctttactgtc ttattgacta    900
tctttgtaaa tgtcttacaa agactaatga cttctccaca atgtgccaat taagtttatc    960 tttttgaaa aataaatggc tggtatcttc atcccttaag aaaataggaa gtttaggctt    1020
gaaaatagag attgcaatag gcaagattaa tttagggcgt gtttgggaaa aagttgcatc   1080
caacattctc tttaattcag tacaagagct ccttcgccgt ttagtgtata ggaaagcgca   1140
aactgatgtt tggaagcttg aaacggcaat aaaatatcaa aatctttata ttaaagctga   1200
acaaaagggg ccctccttat ttatccccTT agttttTAtt tcatttcTT tctaataaag    1260 gggcaaacta gtctcgtaat atattagagg ttaattaaat ttatattcct caaataaaac   1320
ccaattttca tccttaaacg aacctgctga acccTAATT TCGATTACCA ATTCCGATCT    1380
aaaaagaagt catggaagcc attgattccg caatcgatcc tctcagagat ttcgctaaga   1440
gcagtgttcg tctcgtccag cgctgtcaca aacccgatcg caagggtaac gccttttctc   1500
aaaaaaatct catttccgat ttttgatctg tagattaggg ttttctgaaa ttttgatatc   1560
atttgtaatt gaattggtta tcagaattca cgaaagtagc tgtgcgtacg gcgattggat   1620
ttgtggtgat gggattcgtt ggattcttcg tgaagctcgt tttcatccca atcaacaaca   1680
tcatcgttgg atcttcttag tgtagtactt tctttacgag gtaattgatc tcgcattata   1740
tatctacatt ttggttatgt tacttgacat atagtcattg attcaatagt tctgttaatt   1800
cctttaaaga tcattttgac tagaccacat tcttggttca ttcctcaata atttgtaatc   1860
atattggtgg atatagaagt agattggtta tagatcagat agtggaagac tttaggatga   1920
atttcagcta gttttttttt ttggcttatt gtctcaaaag attagtgctt tgctgtctcc   1980
attgcttctg ctatcgacac gcttctgtct ccttgtatct ttattatatc tattcgtccc   2040
atgagttttg tttgttctgt attcgttcgc tctggtgtca tggatggagt ctctgttcca   2100
tgtttctgta atgcatgttg ggttgtttca tgcaagaaat gctgagataa acactcattt   2160
gtgaaagttt ctaaactctg aatcgcgcta caggcaatgc tccgaggagt aggaggagaa   2220
gaacgaacca aacgacatta tcagcccttt gaggaagctc ttagttttgt tattgttttt   2280
gtagccaaat tctccattct tattccattt tcacttatct cttgttcctt atagaccTTa   2340
taagtttttt attcatgtat acaaattata ttgtcatcaa gaagtatctt taaaatctaa   2400
atctcaaatc accaggacta tgttttttgtc caattcgtgg aaccaacttg cagcttgtat   2460
ccattctctt aaccaataaa aaagaaaga agatcaatt tgataaattt ctcagccaca     2520
aattctacat ttaggtttta gcatatcgaa ggctcaatca caaatacaat agatagacta   2580
gagattccag cgtcacgtga gttttatcta taaataaagg accaaaaatc aaatcccgag   2640
ggcattttcg taatccaaca taaaacccctt aaacttcaag tctcatttttt aaacaaatca  2700
```

```
tgttcacaag tctcttcttc ttctctgttt ctctatctct tgctcatctt tctcctgaac    2760
catggcggcg gcaacaacaa caacaacaac atcttcttcg atctccttct ccaccaaacc    2820
atctccttcc tcctccaaat caccattacc aatctccaga ttctccctcc cattctccct    2880 aaacccaac aaatcatcct cctcctcccg ccgccgcggt atcaaatcca gctctccctc    2940
ctccatctcc gccgtgctca acacaaccac caatgtcaca accactccct ctccaaccaa    3000
acctaccaaa cccgaaacat tcatctcccg attcgctcca gatcaacccc gcaaaggcgc    3060
tgatatcctc gtcgaagctt tagaacgtca aggcgtagaa accgtattcg cttaccctgg    3120
aggtgcatca atggagattc accaagcctt aacccgctct tcctcaatcc gtaacgtcct    3180
tcctcgtcac gaacaaggag gtgtattcgc agcagaagga tacgctcgat cctcaggtaa    3240
accaggtatc tgtatagcca cttcaggtcc cggagctaca aatctcgtta gcggattagc    3300
cgatgcgttg ttagatagtg ttcctcttgt agcaatcaca ggacaagtcc ctcgtcgtat    3360
gattggtaca gatgcgtttc aagagactcc gattgttgag gtaacgcgtt cgattacgaa    3420
gcataactat cttgtgatgg atgttgaaga tatccctagg attattgagg aagctttctt    3480
tttagctact tctggtagac ctggacctgt tttggttgat gttcctaaag atattcaaca    3540
acagcttgcg attcctaatt gggaacaggc tatgaaatta cctggttata tgtctaggat    3600
gcctaaacct ccggaagatt ctcatttgga gcagattgtt aggttgattt ctgagtctaa    3660
gaagcctgtg ttgtatgttg gtggtggttg tttgaattct agcgatgaat tgggtaggtt    3720
tgttgagctt acggggatcc ctgttgcgag tacgttgatg gggctgggat cttatccttg    3780
tgatgatgag ttgtcgttac atatgcttgg aatgcatggg actgtgtatg caaattacgc    3840
tgtggagcat agtgatttgt tgttggcgtt tggggtaagg tttgatgatc gtgtcacggg    3900
taagcttgag gcttttgcta gtagggctaa gattgttcat attgatattg actcggctga    3960
gattgggaag aataagactc ctcatgtgtc tgtgtgtggt gatgttaagc tggctttgca    4020
agggatgaat aaggttcttg agaaccgagc ggaggagctt aagcttgatt ttggagtttg    4080
gaggaatgag ttgaacgtac agaaacagaa gtttccgttg agctttaaga cgtttgggga    4140
agctattcct ccacagtatg cgattaaggt ccttgatgag ttgactgatg gaaaagccat    4200
aataagtact ggtgtcgggc aacatcaaat gtgggcggcg cagttctaca attacaagaa    4260
accaaggcag tggctatcat caggaggcct tggagctatg ggatttggac ttcctgctgc    4320
gattggagcg tctgttgcta accctgatgc gatagttgtg gatattgacg gagatggaag    4380 cttttataatg aatgtgcaag agctagccac tattcgtgta gagaatcttc cagtgaaggt    4440 actttttatta aacaaccagc atcttggcat ggttatgcaa tgggaagatc ggttctacaa    4500
agctaaccga gctcacacat ttctcgggga tccggctcag gaggacgaga tattcccgaa    4560
catgttgctg tttgcagcag cttgcgggat tccagcggcg agggtgacaa agaaagcaga    4620
tctccgagaa gctattcaga caatgctgga tacaccagga ccttacctgt tggatgtgat    4680
ttgtccgcac caagaacatg tgttgccgat gatcccgaat ggtggcactt tcaacgatgt    4740
cataacggaa ggagatggcc ggattaaata ctgagagatg aaaccggtga ttatcagaac    4800
cttttatggt ctttgtatgc atatggtaaa aaaacttagt ttgcaatttc ctgtttgttt    4860
tggtaatttg agtttctttt agttgttgat ctgcctgctt tttggtttac gtcagactac    4920
tactgctgtt gttgtttggt ttccttttctt tcattttata aataaataat ccggttcggt    4980
ttactccttg tgactggctc agtttggtta ttgcgaaatg caaatggtaa attgagtaat    5040
tgaaattcgt tattagggtt ctaacctgtt ttaacagtca ctgggttaat atctctcgaa    5100
```

```
tcttgcatgg aaaatgctct taccattggt ttttaattga aatgtgctca tatgggccgt    5160
ggtttccaaa ttaaataaaa ctacgatgtc atcgagaagt aaaatcaact gtgtccacat    5220
tatcagtttt gtgtatacga tgaaataggg taattcaaaa tctagcttga tatgccttt     5280 ggttcatttt aaccttctgt aaacattttt tcagattttg aacaagtaaa tccaaaaaaa    5340
aaaaaaaaaa atctcaactc aacactaaat tattttaatg tataaaagat gcttaaaaca    5400
tttggcttaa aagaagaag ctaaaaacat agagaactct tgtaaattga agtatgaaaa     5460
tatactgaat tgggtattat atgaattttt ctgatttagg attcacatga tccaaaaagg    5520
aaatccagaa gcactaatca gacattggaa gtaggaatat tcaaaaagt tttttttttt     5580 taagtaagtg acaaaagctt ttaaaaaata gaaagaaac tagtattaaa gttgtaaatt     5640
taataaacaa aagaaatttt ttatattttt tcatttcttt ttccagcatg agggatctta    5700
tccttgtgat gatgagttgt cgttacatat gcttggaatg catgggactg tgtatgcaaa    5760
ttacgctgtg gagcatagtg atttgttgtt ggcgtttgga gtaaggtttg atgatcgtgt    5820
cacgggtaag cttgaggctt ttgctagtag ggctaagatt gttcatattg atattgactc    5880
ggctgagatt gggaagaata agactcctca tgtgtctgtg tgtggtgatg ttaagctggc    5940
tttgcaaggg atgaataagg ttcttgagaa ccgagcggag gagcttaagc ttgattttgg    6000 agttggagg aatgagttga acgtacagaa acagaagttt ccgttgagct ttaagacgtt     6060
tggggaagct gtcccatgcc catcaaagaa gacagtacac gatccgagct acgaatgggt    6120
aggcccaata aggcgagaag ggccacccag tccaatgagg gaagcaaac taacacaaaa     6180 tacccatcta ataaggacct ataagtttgt atttttttaaa tgtatttgaa aaattcaaac   6240
aatttttaat tgttaatttt ttttcctaaa attaaacaaa catattttg tagaagcaaa     6300 gatatcataa tgttttgatg atgctaaaga aacacgcttc tcaagtttga tccaaaataa    6360
aactctaaga aattcaagat aaatgataaa gttagtctat agagtcttag aaagaagttt    6420
ctaaattgat gatgcataag ttatgaccaa aggtttttc tcaaaagctt ttaaaagaga     6480
tatttattct ctgataatca attactagtg acaaaaatgt ttactggaat gctttaaaat    6540 gttttaata ttttgaaagc ttgtaatcga ttacacaaga cttgtaatcg attaccaaaa     6600
gttttgaaca ttttaagaca acctttagaa atttgaattt aaatttcaaa gtctgtaatc    6660
gattaccaga attaaaatta aaattttaga tgtgaagagt caaagtcttt cagaaaacaa    6720
ttgtgtaatc gattacacca ttttggtaat cgattaccac tgagaaattt tctaaaatat    6780
ctccgaacag ttcatctctt tcaaatgatt ttgaatgacc attaaaggct tatatataag    6840
tgacttggga catgaatttt cagagagttt ttctgaactg aaatgttta tcctctcaaa     6900 aatgattcct tggtctaaca cttgcatatt taataaagaa tcttgattga tcttcaattg    6960
taatatcctt cttttaaaga gagaaacttc ttcttcttct tattcaaagg aaattgttta    7020
agagaccgag gatctcttaa atggtaagga ttcctgaaca caatgcaagg attatccttg    7080
tgtgattcag actttgtaaa aggggttttt acaaagagag tggaaaatct caagtgggtt    7140
gcttgagtga ggacttgacg taggcatgaa aaatggctga accagtataa attaagttta    7200
catttctctc ttcccttaac cttctttat ttattgttat ttatcttta ttttaaaaaa      7260 gtttatttg aattgtcttt tgagtaattc atattaatgg tgcattgtta attcaaaaaa     7320
agagtggaat tttaattgag aaatagtttt tgtatcttaa ttcaatcccc ttttcttaag    7380
ataactgaga tcacttgtct aacaatttg tgtataatta cattcaataa ttttttttagt   7440
```

```
taatatctta aatatataaa ttccaaactc ttgaaattaa aaaatatgc ataatttatt    7500
taataaattt aaattttagg aaaaaaagtt aagggtcat taaatttgat aaaaagttaa    7560
gaatattatt gaattttata atttttttta tagaaaatag tgaaaacaat aaaagttttt    7620
ttctatttct taacaaccct ttcaataaaa aaatgaaatg aaaataatat gacattttta    7680
taattaagag taatataaaa ataaaataaa ataattttaa accaaggac tcataagcat     7740
gttattgctc taccactcat aaaaattttt ctcctattat cttttgatg ataaaatatt     7800
gtcatactag aaataaaata tatttttct atatcctcta tatgagtcaa tcttatttta    7860
agtacaatgt tactgaaagt cattttgcaa taaaaatctt ccaagatttt tcccaaacaa    7920
ttgttgtaat tttagttctt taaaatatac atataaaaat gcattatttg tatggtataa    7980
tataaataat agaaacaata tcaacatttc tcattgagta ttgagaagct aaagtaaatt    8040
acttgactac attgccgtag tgcgacgaat tagattgtaa tatctaaaat acttaagtag    8100
tgtagataag tctatgaatg ttttcagat taattgcacg ataattttt ttaattctac     8160
tataattcca tatttatttg aaaaacttca tgataacatg catcctttat ttattacatt    8220
aaccttctta aatatttcaa atatcacgtt tcactgcaag aaaagtttta taatctttaa    8280
taagcttcat acatgctcgt accttcccac aataagccaa tttgggtctg ccaatgtcct    8340
cactcttgaa aaggaaaat ataaacctca aagtgatcat gtgatatgat aaaaatttaa    8400
aaatatataa attcatagag aaaaaaagga atgaaaatga attgtaagaa agtgaaatgt    8460
atgaaaatct gaactcattc aaaatcatat aagaaaataa accgtggaag aaaacgagca    8520
tcacattcac ataacatgtt ctgctccaac actaattatt ctgctaccgc agatatagca    8580
accagagtgg ccatttatt acatttgtat cgatccatgc atttacgtac actccatcta    8640
gctaaacatc atatcactac taacatgaca caaaataagg aaaaaactca gaatgtcagc    8700
ttgaagttta atagatttcc tcctttaata acatttaaat atgattatt tttataataa    8760
aaatatcttt aaaaatattt atttagtagt tatttttagc ataaatatta ggaattgata    8820
cttttcttat ttatgacttg cagatataaa aatgaagaat taaaagtaaa gaaaatccaa    8880
aaaatatcaa aaatataaat aaggaagatt ttttggcgtc agacccaagt tcattccaac    8940
agctgtaatt ttttcagatt aaaaaggatg aatgatgaat gaaattaaaa gtaagaaagg    9000
aataaagaca caccgagtct cggagcaatc taatacacac ctaaagcctg agaactctcc    9060
cttaggaaat tccttcttct cttcatcat tctttatttc cttttccat ctcttctctt      9120
ccatcagttc gtatatccct ttgctagtgt aaaaccccctt atggttatga gaggctaaac    9180
ccttagttag ggtttgacag gcttaaaaag tcaaagatg tattatacac ttcatattta     9240
tcaatgcaaa cagatgtttt ctttcctatt atcctttctt atttctaatt tcatgcatca    9300
ttcatccttg cattatcttt ggggttagg tgctcgacaa aggataatcc caagaaggt      9360
tttgcatgta tctatttcag gaattagtcg ctcgacagag agtaatttct aataaaacta    9420
aaagaagaa atatcttaat aaaatcattg ttagacataa aatgattgta ttatgcccat     9480
gcatcaaagc aaacatatag aattataact tcatgtattt tatctattgg ctctttgcaa    9540
aaacatttgg aagatagata ggtaaaatag gtgagacatc aggtatttta atagatgtga    9600
gtaagataaa ttcacctgat agagaaaatc ataataata tatcttagac aaataagaca     9660
tgctaggtcc taacattttc atcccattga attcactatt ttttcttttg ttatttagta    9720
ataattatta tttatactc tgttcttta aaattatctt ttataccctat cttatattt      9780
tctcttataa attaaaaatt atccaacaca aatacaaaac aaagttaaaa tcgacactca    9840
```

```
agacttccga gttttttgatc aaaaagcctt tctatctttc ctcttgcggt ctgctccatt    9900
ttagaagaaa aggaaccaat taataaaatg gacagcgcaa tcaaataagt aaaaatttac    9960
ttaatataat gatgcatgat agctagaagg gtaccaataa tttaaccctg atcaataacg   10020
tcaatagaga ctctccccaa accccaaatt agggtatcgc tgatccttat gaaaaccccg   10080
aaataaataa attgaaagga accctaaacg cgaaaccctc tatttgcatc gtggaagcgc   10140
agaaaacttc actgagataa atgaagtcgg atagaacata gattctcgta gatcatccat   10200
cacaaaccct aaaagaagta ttagattttc gcgttcggag aaacaaacct gagtggtaga   10260
aacgaagctt gatttgttgg aacgattgtt gagagaaaga acagagagca aaataaggct   10320
tctattttct taatcaaacg ttggtgtttg ttgccaatgt tgtgttaggc ttatttataa   10380
tttctctgtt agcttgtaaa gcacgcaaca ataagatgag atataggatt ttttttttat   10440
tttaaaaaaa aagacatttg ccgtcatata aggataaatt aaggcttaaa aaaagatagt   10500
tattttcttt aaaaaaataa ttatttctga aatttaatat tttgaagata gtttgaattt   10560
acttatgaaa atatttgttt tgagtttcaa tttataaaat catttctagt gtgggaagtt   10620
acatttcgtt tggattagaa attttaaaat tctaga                              10656

<210> SEQ ID NO 2
<211> LENGTH: 1311
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gtgagactcc aacagcaaga gtcactttgt agcccactca aataaatgtg aacattaata     60
ggtggatttg gacaatacag gccccttgtt ttaacaaggt cttgcagttt cacttaaaaa    120
ttcatagtag ttagaagaac taatattatg tgccaactga caataaaaga aaaacaatc    180 tttccaattt atattacaca taagacacag cctgaaaaaa gaagagagca tgtatctgta    240
aacaagttag gcatgatgcc aaaggagcag cagcataaca aaacaaacga aaattacaag    300
aaaatatggc ttaccagcat ggttgctggg aaggactgga tcaagaagtg agcggcaatc    360
aacaagtgtt actacagcat actttttctct ttgataatca ggaaggcatc tagaggtcca    420
tgcagcaatc attccagctg cagcaagtgc cccacaaagt ttgatccctc ttgatttgca    480
tccctacatg atcttgcata attagcttaa acccatcaag ctagctacca gatcataagc    540
aaaaagtgag cagagtgcca tatcaattat tcacagaaat tagattataa acattggat    600 gcataagaat gaatttcaat tacaaatacg cagagacaaa aaagaagata atgtgacatt    660
gaggctgctt tgtaccagga aaaataatag cagctgatat tattagttat aattggctgc    720
aaatttctcc aaattgtaaa tatgaatttc attaatcact ttatttagct gataaatcca    780
attgatatta taaagagttt ggatcaaacc atagggctgt gacctgtgaa acacaaactc    840
ctcattcgta ttagaggctc tacccctccta atagctttgg ctttactgtc ttattgacta    900
tctttgtaaa tgtcttacaa agactaatga cttctccaca atgtgccaat taagttttatc   960 tttttgaaa ataaatggc tggtatcttc atcccttaag aaaataggaa gtttaggctt   1020 gaaatagag attgcaatag gcaagattaa tttagggcgt gttttgggaaa aagttgcatc   1080 caacattctc tttaattcag tacaagagct ccttcgccgt ttagtgtata ggaaagcgca   1140
aactgatgtt tggaagcttg aaacggcaat aaaatatcaa aatctttata ttaaagctga   1200
```

```
acaaaagggg ccctccttat ttatcccctt agtttttatt ttcatttctt tctaataaag    1260
gggcaaacta gtctcgtaat atattagagg ttaattaaat ttatattcct c             1311
```

<210> SEQ ID NO 3
<211> LENGTH: 4587
<212> TYPE: DNA
<213> ORGANISM: Artificial Sequence
<220> FEATURE:
<223> OTHER INFORMATION: Description of Artificial Sequence: Synthetic
   polynucleotide

<400> SEQUENCE: 3

```
tgtcccatgc ccatcaaaga agacagtaca cgatccgagc tacgaatggg taggcccaat      60
aaggcgagaa gggccaccca gtccaatgag ggaagacaaa ctaacacaaa atacccatct     120
aataaggacc tataagtttg tattttttaa atgtatttga aaaattcaaa caatttttaa     180
ttgttaattt ttttttcctaa aattaaacaa acatatttt gtagaagcaa agatatcata     240
atgttttgat gatgctaaag aaacacgctt ctcaagtttg atccaaaata aaactctaag     300
aaattcaaga taaatgataa agttagtcta tagagtctta gaaagaagtt tctaaattga     360
tgatgcataa gttatgacca aaggtttttt ctcaaaagct tttaaagag atatttattc     420 tctgataatc aattactagt gacaaaaatg tttactggaa tgctttaaaa tgttttaat     480 attttgaaag cttgtaatcg attacacaag acttgtaatc gattaccaaa gttttgaac     540 attttaagac aacctttaga aatttgaatt taaatttcaa agtctgtaat cgattaccag     600
aattaaaatt aaaattttag atgtgaagag tcaaagtct tcagaaaaca attgtgtaat     660
cgattacacc atttggtaa tcgattacca ctgagaaatt ttctaaaata tctccgaaca     720
gttacatctt ttcaaatgat tttgaatgac cattaaaggc ttatatataa gtgacttggg     780
acatgaattt tcagagagtt tttctgaact gaaatgtttt atcctctcaa aaatgattcc     840
ttggtctaac acttgcatat ttaataaaga atcttgattg atcttcaatt gtaatatcct     900
tcttttaaag agagaaactt cttcttcttc ttattcaaag gaaattgttt aagagaccga     960
ggatctctta aatggtaagg attcctgaac acaatggaag gattatcctt gtgtgattca    1020
gactttgtaa aaggggtttt tacaaagaga gtggaaaatc tcaagtgggt tgcttgagtg    1080
aggacttgac gtaggcatga aaaatggctg aaccagtata aattaagttt acatttctct    1140
cttcccttaa ccttctttta tttattgtta tttatcttt attttaaaaa agtttatttt    1200
gaattgtctt ttgagtaatt catattaatg gtgcattgtt aattcaaaaa agagtggaa     1260 ttttaattga gaaatagttt ttgtatccta attcaatccc cttttcttaa gataactgag    1320
atcacttgtc taacaatttt gtgtataatt acattcaata attttttag ttaatatctt    1380 aaatatataa attccaaact cttgaaatta aaaaatatg cataatttat ttaataaatt    1440
taaattttag gaaaaaaagt taaggggtca ttaaatttga taaaaagtta agaatattat    1500 tgaatttat aatttttttt atagaaaata gtgaaaacaa taaaagtttt tttctatttc    1560
ttaacaaccc tttcaataaa aaaatgaaat gaaaataata tgacattttt ataattaaga    1620
gtaatataaa aataaaataa aataattta aaccaaagga ctcataagca tgttattgct    1680
ctaccactca taaaaatttt tctcctatta tctttttgat gataaaatat tgtcatacta    1740
gaaataaaat atatttttc tatatcctct atatgagtca atcttatttt aagtacaatg    1800
ttactgaaag tcatttgtgca ataaaaaatct tccaagattt tcccaaaaca attgttgtaa    1860
ttttagttct ttaaaatata catataaaaa tgcattattt gtatggtata atataaataa    1920
```

```
tagaaacaat atcaacattt ctcattgagt attgagaagc taaagtaaat tacttgacta   1980
cattgccgta gtgcgacgaa ttagattgta atatctaaaa tacttaagta gtgtagataa   2040
gtctatgaat gttttttcaga ttaattgcac gataatttt tttaattcta ctataattcc    2100
atatttattt gaaaaacttc atgataacat gcatccttta tttattacat taaccttctt   2160
aaatatttca aatatcacgt ttcactgcaa gaaaagtttt ataatcttta ataagcttca   2220
tacatgctcg taccttccca caataagcca atttgggtct gccaatgtcc tcactcttga   2280
aaaaggaaaa tataaacctc aaagtgatca tgtgatatga taaaaattta aaaatatata   2340
aattcataga gaaaaaaagg aatgaaaatg aattgtaaga aagtgaaatg tatgaaaatc   2400
tgaactcatt caaaatcata taagaaaata aaccgtggaa gaaaacgagc atcacattca   2460
cataacatgt tctgctccaa cactaattat tctgctaccg cagatatagc aaccagagtg   2520
gccattttat tacatttgta tcgatccatg catttacgta cactccatct agctaaacat   2580
catatcacta ctaacatgac acaaaataag gaaaaaactc agaatgtcag cttgaagttt   2640
aatagatttc ctcctttaat aacatttaaa tatgatttat ttttataata aaaatatctt   2700
taaaaatatt tatttagtag ttatttttag cataaatatt aggaattgat acttttctta   2760
tttatgactt gcagatataa aaatgaagaa ttaaaagtaa agaaaatcca aaaaatatca   2820
aaaatataaa taaggaagat ttttttggcgt cagacccaag ttcattccaa cagctgtaat   2880
tttttcagat taaaaaggat gaatgatgaa tgaaattaaa agtaagaaag gaataaagac   2940
acaccgagtc tcggagcaat ctaatacaca cctaaagcct gagaactctc ccttaggaaa   3000
ttccttcttc tctttcatca ttctttattt ccttttttcca tctcttctct tccatcagtt   3060
cgtatatccc tttgctagtg taaaacccct tatggttatg agaggctaaa cccttagtta   3120
gggtttgaca ggcttaaaaa gtcaaaagat gtattataca cttcatattt atcaatgcaa   3180
acagatgttt tctttcctat tatccttcct tatttctaat ttcatgcatc attcatcctt   3240
gcattatctt tgggggttag gtgctcgaca aaggataatc ccaaagaagg ttttgcatgt   3300
atctatttca ggaattagtc gctcgacaga gagtaatttc taataaaact aaaaagaaga   3360
aatatcttaa taaaatcatt gttagacata aaatgattgt attatgccca tgcatcaaag   3420
caaacatata gaattataac ttcatgtatt ttatctattg gctctttgca aaaacatttg   3480
gaagatagat aggtaaaata ggtgagacat caggtatttt aatagatgtg agtaagataa   3540
attcacctga tagagaaaat cataaataat atatcttaga caaataagac atgctaggtc   3600
ctaacatttt catcccattg aattcactat ttttctttt gttatttagt aataattatt    3660
attttatact ctgttctttt aaaattatct tttatatccta tcttatattt ttctcttata  3720
aattaaaaat tatccaacac aaatacaaaa caaagttaaa atcgacactc aagacttccg   3780 agttttttgat caaaaagcct ttctatcttt cctcttgcgg tctgctccat tttagaagaa   3840
aaggaaccaa ttaataaaat ggacagcgca atcaaataag taaaaattta cttaatataa   3900
tgatgcatga tagctagaag ggtaccaata atttaaccct gatcaataac gtcaatagag   3960
actctcccca aaccccaaat tagggtatcg ctgatcctta tgaaaacccc gaaataaata   4020
aattgaaagg aaccctaaac gcgaaaccct atatttgcat cgtggaagcg cagaaaactt   4080
cactgagata aatgaagtcg gatagaacat agattctcgt agatcatcca tcacaaaccc   4140
taaaagaagt attagatttt cgcgttcgga gaaacaaacc tgagtggtag aaacgaagct   4200
tgatttgttg gaacgattgt tgagagaaag aacagagagc aaaataaggc ttctatttcc   4260
```

```
ttaatcaaac gttggtgttt gttgccaatg ttgtgttagg cttatttata atttctctgt    4320
tagcttgtaa agcacgcaac aataagatga gatataggat ttttttttta ttttaaaaaa    4380
aaagacattt gccgtcatat aaggataaat taaggcttaa aaaaagatag ttattttctt    4440
taaaaaaata attatttctg aaatttaata ttttgaagat agtttgaatt tacttatgaa    4500
aatatttgtt ttgagtttca atttataaaa tcatttctag tgtgggaagt tacatttcgt    4560
ttggattaga aattttaaaa ttctaga                                        4587

<210> SEQ ID NO 4
<211> LENGTH: 6156
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
ctggcacgac aggtttcccg actggaaagc gggcagtgag cgcaacgcaa ttaatgtgag      60
ttagctcact cattaggcac cccaggcttt acactttatg cttccggctc gtatgttgtg    120
tggaattgtg agcggataac aatttcacac aggaaacagc tatgaccatg attacgccaa    180
gctcgaaatt aaccctcact aaagggaaca aaagctggag ctccaccgcg gtggcggccg    240
ctctagatta tgtatttcca actttcatta acaatataat cgcatataaa tgaaaaatcg    300
tttccaggat aatattttga tgaaatctca tattattgtt cgtactcgga ttgatgttga    360
aggcttgaag cgcttcaaat tatagaccag attatttaag ttttttcttt gtttactcca    420
tatcaatttg atccattata ctacctaaga aaatttaggt aacatagaat tatttattgt    480
tatagtaaaa aaaaggaaaa ccacaaaaat aatctacttt tacgtatata ctattttcat    540
gacataagta attaagttgt acaacttttt tttaatgaaa agagagagta aatttatcat    600
gttcatgtgt agttacctcg tgaataaccg acggttatat agacgcctaa catgaattgt    660
tcagttgaag acagttcaaa acatgtgttt cactctaaaa tcctcaacaa aaaaaaagtg    720
ttaaaatttg taaacctctt tcaagcaaaa aagaaaaaag tgttagaatc ccaagattct    780
ttcataatcc ggaatcttgg ctgaaaacgt ataaaagaga ttgacgtagt aacaaggagt    840
cttggtatgc ttccatgctt tttatccttt tttgtcatgg aaccatgatt tggttaccat    900
ttattatgta accgaaattt tcattgtaat aatgaatatt taaattttta gcaaaaaaaa    960
acaaaaaaaa acaaggagtc ttgtcttcgt tctcaaattt cagagctctt gcacttttca   1020
agagttttac tttgatgagt gagacatttg tcttttagt gttatttttc taaacttaaa   1080
atagtagcat caacatcact caattataat tcttaagatg ttgtagaaaa atatttttata  1140 gatgaaagt aatcgatatt aagacaaata agaaaccaaa ccggactttg tgttcagacc    1200
gaatcaaatc tgaattggag aaattatggt ggaggcgaaa gtcaacggaa ctaaagtata   1260
aaaccaaatg tcaaaaataa acccaatttt catccttaa acgaacctgc tgaaacccta    1320
atttcgatta ccaattccga tctaaaaaga agtcatggaa gccattgatt ccgcaatcga   1380
tcctctcaga gatttcgcta agagcagtgt tcgtctcgtc cagcgctgtc acaaacccga   1440
tcgcaagggt aacgcctttt ctcaaaaaaa tctcatttcc gattttgat ctgtagatta    1500 gggttttctg aaattttgat atcatttgta attgaattgg ttatcagaat tcacgaaagt   1560
agctgtgcgt acggcgattg gatttgtggt gatgggattc gttggattct tcgtgaagct   1620
cgttttcatc ccaatcaaca acatcatcgt tggatcttct tagtgtagta ctttctttac   1680
```

```
gaggtaattg atctcgcatt atatatctac attttggtta tgttacttga catatagtca    1740
ttgattcaat agttctgtta attcctttaa agatcatttt gactagacca cattcttggt    1800
tcattcctca ataatttgta atcatattgg tggatataga agtagattgg ttatagatca    1860
gatagtggaa gacttaggga tgaatttcag ctagttttt tttttggctt attgtctcaa    1920
aagattagtg ctttgctgtc tccattgctt ctgctatcga cacgcttctg tctccttgta    1980
tctttattat atctattcgt cccatgagtt ttgtttgttc tgtattcgtt cgctctggtg    2040
tcatggatgg agtctctgtt ccatgtttct gtaatgcatg ttgggttgtt tcatgcaaga    2100
aatgctgaga taaacactca tttgtgaaag tttctaaact ctgaatcgcg ctacaggcaa    2160
tgctccgagg agtaggagga gaagaacgaa ccaaacgaca ttatcagccc tttgaggaag    2220
ctcttagttt tgttattgtt tttgtagcca aattctccat tcttattcca tttttcactta    2280 tctcttgttc cttatagacc ttataagttt tttattcatg tatacaaatt atattgtcat    2340
caagaagtat ctttaaaatc taaatctcaa atcaccagga ctatgttttt gtccaattcg    2400
tggaaccaac ttgcagcttg tatccattct cttaaccaat aaaaaaagaa agaaagatca    2460
atttgataaa tttctcagcc acaaattcta catttaggtt ttagcatatc gaaggctcaa    2520
tcacaaatac aatagataga ctagagattc cagcgtcacg tgagttttat ctataaataa    2580
aggaccaaaa atcaaatccc gagggcattt tcgtaatcca acataaaacc cttaaacttc    2640
aagtctcatt tttaaacaaa tcatgttcac aagtctcttc ttcttctctg tttctctatc    2700
tcttgctcat ctttctcctg aaccatggcg gcggcaacaa caacaacaac aacatcttct    2760
tcgatctcct tctccaccaa accatctcct tcctcctcca aatcaccatt accaatctcc    2820
agattctccc tcccattctc cctaaacccc aacaaatcat cctcctcctc ccgccgccgc    2880
ggtatcaaat ccagctctcc ctcctccatc tccgccgtgc tcaacacaac caccaatgtc    2940
acaaccactc cctctccaac caaacctacc aaacccgaaa cattcatctc ccgattcgct    3000
ccagatcaac cccgcaaagg cgctgatatc ctcgtcgaag ctttagaacg tcaaggcgta    3060
gaaaccgtat tcgcttaccc tggaggtgca tcaatggaga ttcaccaagc cttaacccgc    3120
tcttcctcaa tccgtaacgt ccttcctcgt cacgaacaag gaggtgtatt cgcagcagaa    3180
ggatacgctc gatcctcagg taaaccaggt atctgtatag ccacttcagg tcccggagct    3240
acaaatctcg ttagcggatt agccgatgcg ttgttagata tgttcctct tgtagcaatc     3300 acaggacaag tccctcgtcg tatgattggt acagatgcgt ttcaagagac tccgattgtt    3360
gaggtaacgc gttcgattac gaagcataac tatcttgtga tggatgttga agatatccct    3420
aggattattg aggaagcttt cttttttagct acttctggta gacctggacc tgttttggtt    3480
gatgttccta aagatattca acaacagctt gcgattccta attgggaaca ggctatgaga    3540
ttacctggtt atatgtctag gatgcctaaa cctccggaag attctcattt ggagcagatt    3600
gttaggttga tttctgagtc taagaagcct gtgttgtatg ttggtggtgg ttgtttgaat    3660
tctagcgatg aattgggtag gtttgttgag cttacgggga tccctgttgc gagtacgttg    3720
atggggctgg atcttatcc ttgtgatgat gagttgtcgt tacatatgct tggaatgcat     3780
gggactgtgt atgcaaatta cgctgtggag catagtgatt tgttgttggc gtttggggta    3840
aggtttgatg atcgtgtcac gggtaagctt gaggcttttg ctagtagggc taagattgtt    3900
catattgata ttgactcggc tgagattggg aagaataaga ctcctcatgt gtctgtgtgt    3960
ggtgatgtta agctggcttt gcaagggatg aataaggttc ttgagaaccg agcggaggag    4020
cttaagcttg attttggagt ttggaggaat gagttgaacg tacagaaaca gaagtttccg    4080
```

-continued

```
ttgagcttta agacgtttgg ggaagctatt cctccacagt atgcgattaa ggtccttgat   4140
gagttgactg atggaaaagc cataataagt actggtgtcg ggcaacatca aatgtgggcg   4200
gcgcagttct acaattacaa gaaaccaagg cagtggctat catcaggagg ccttggagct   4260
atgggatttg gacttcctgc tgcgattgga gcgtctgttg ctaaccctga tgcgatagtt   4320
gtggatattg acggagatgg aagctttata atgaatgtgc aagagctagc cactattcgt   4380
gtagagaatc ttccagtgaa ggtacttttta ttaaacaacc agcatcttgg catggttatg   4440
caatgggaag atcggttcta caaagctaac cgagctcaca catttctcgg ggatccggct   4500
caggaggacg agatattccc gaacatgttg ctgtttgcag cagcttgcgg gattccagcg   4560
gcgagggtga caaagaaagc agatctccga gaagctattc agacaatgct ggatacacca   4620
ggaccttacc tgttggatgt gatttgtccg caccaagaac atgtgttgcc gatgatcccg   4680
aatggtggca ctttcaacga tgtcataacg gaaggagatg gccggattaa atactgagag   4740
atgaaaccgg tgattatcag aacctttat ggtctttgta tgcatatggt aaaaaaactt   4800
agtttgcaat ttcctgtttg ttttggtaat ttgagtttct tttagttgtt gatctgcctg   4860
cttttttggtt tacgtcagac tactactgct gttgttgttt ggtttccttt ctttcatttt   4920
ataaataaat aatccggttc ggtttactcc ttgtgactgg ctcagtttgg ttattgcgaa   4980
atgcgaatgg taaattgagt aattgaaatt cgttattagg gttctaagct gttttaacag   5040
tcactgggtt aatatctctc gaatcttgca tggaaaatgc tcttaccatt ggttttttaat   5100
tgaaatgtgc tcatatgggc cgtggtttcc aaattaaata aaactacgat gtcatcgaga   5160
agtaaaatca actgtgtcca cattatcagt tttgtgtata cgatgaaata gggtaattca   5220
aaatctagct tgatatgcct tttggttcat tttaaccttc tgtaaacatt ttttcagatt   5280
ttgaacaagt aaatccaaaa aaaaaaaaaa aaaatctcaa ctcaacacta aattattttta   5340
atgtataaaa gatgcttaaa acatttggct taaagaaag aagctaaaaa catagagaac   5400
tcttgtaaat tgaagtatga aaatatactg aattgggtat tatatgaatt tttctgattt   5460
aggattcaca tgatccaaaa aggaaatcca gaagcactaa tcagacattg gaagtaggaa   5520
tatttcaaaa agttttttt tttttaagtaa gtgacaaaag cttttaaaaa atagaaaaga   5580
aactagtatt aaagttgtaa atttaataaa caaagaaat tttttatat ttttcatttc   5640
tttttccagc atgaggttat gatggcagga tgtggatttc atttttttcc ttttgatagc   5700
cttttaattg atctattata attgacgaaa aaatattagt taattataga tatatttag    5760
gtagtattag caatttacac ttccaaaaga ctatgtaagt tgtaaatatg atgcgttgat   5820
ctcttcatca ttcaatggtt agtcaaaaaa ataaaagctt aactagtaaa ctaaagtagt   5880
caaaaattgt actttagttt aaaatatac atgaataatc caaaacgaca tttatgtgaa   5940
acaaaaacaa tatctagaac tagtggatcc cccgggctgc aggaattcga tatcaagctt   6000
atcgataccg tcgacctcga ggggggggcc ggtacccaat tcgccctata gtgagtcgta   6060
ttacaattca ctggccgtcg ttttacaacg tcgtgactgg gaaaaccctg gcgttaccca   6120
acttaatcgc cttgcagcac atccccctt cgccag                             6156
```

<210> SEQ ID NO 5
<211> LENGTH: 2
<212> TYPE: DNA
<213> ORGANISM: Artificial Sequence
<220> FEATURE:
<223> OTHER INFORMATION: Description of Artificial Sequence: Synthetic oligonucleotide

```
<400> SEQUENCE: 5 ca                                                                          2

<210> SEQ ID NO 6
<211> LENGTH: 2
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6 ct                                                                          2

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgcgttatcc cctgattctg                                                      20

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8 tgttgggggtt tagggag                                                        17

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgaaggctca atcacaaata c                                                    21

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agcaggcaga tcaacaac                                                        18

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 11
gaacatgtgt tgccgatgat                                              20

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cgcaactgtt gggaaggg                                                18

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gttttacaac gtcgtgactg                                              20

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cggttagctc cttcggtc                                                18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cactgcggcc aacttact                                                18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cttggcgtaa tcatggtc                                                18

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
```
gcagcttgta tccattctct taacc                                          25

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ttgttgattg ggatgaaaac ga                                             22

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
acgaagaatc caacgaatcc c                                              21

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aaggaaatcc agaagcacta atca                                           24

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
taatgcgaga tcaattacct c                                              21

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
caattacctc gtaaagaaag tacta                                          25

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

```
gcttgatatg cctttggtt c                                              21
```

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

```
ttgtcttccc tcattggac                                                19
```

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

```
gacgagatat tcccgaac                                                 18
```

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
gtctgattag tgcttctgg                                                19
```

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
ccctgttgcg agtacgttga                                               20
```

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
cttccgttat gacatcgttg                                               20
```

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
aaccactccc tctccaac                                                 18
```

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctgatgatag ccactgcc                                                 18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ttcgttcgct ctggtgtc                                                 18

<210> SEQ ID NO 32
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
acggtttcta cgccttg                                                  17

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gaaaatagga agtttaggct tg                                            22

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gggctgataa tgtcgtttg                                                19

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gccctcctta tttatcccct ta                                            22

```
<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
acaaacctac ccaattcatc gc                                              22

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gaaaatagga agtttaggct tg                                              22

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cactgctctt agcgaaatct c                                               21

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gccctcctta tttatcccct ta                                              22

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gccgtacgca cagctacttt c                                               21

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ataggaaagc gcaaactg                                                   18
```

-continued

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cgaacactgc tcttagcgaa at                                              22

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gccctcctta tttatcccct ta                                              22

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aggatcgatt gcggaatca                                                  19

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aacagaagtt tccgttgagc tttaagac                                        28

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
tttggggaag ctgtcccatg ccc                                             23

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cattcgtagc tcggatcgtg tac                                             23

<210> SEQ ID NO 48

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ccagcttcgc cgcttccttc                                                       20

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
cttcaccttc tatgcccctg acac                                                  24

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gaaggcaagc ccatctgcaa gcc                                                   23

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
acgaacctgc tgaaacccta at                                                    22

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
taagaatgga gaatttggct aca                                                   23

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tgaagcagca gctgagtttc gc                                                    22

<210> SEQ ID NO 54
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ggcagtctga accgtctcct c                                              21

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gcttgggaga cagagaaaga ga                                             22

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56 cctttgctt gacaacctga at                                              22

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ttggaatgca tgggactgt                                                 19

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tgtcttccct cattggactg                                                20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ccacaatgtg ccaattaagt                                                20

<210> SEQ ID NO 60
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 60
gcgtgtttct ttagcatca                                                  19

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ctccttcgcc gtttagtgta                                                 20

<210> SEQ ID NO 62
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gtttcgcgtt tagggttcc                                                  19

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ataagccaat ttgggtctgc c                                               21

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gtttcgcgtt tagggttcc                                                  19

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tggtcgcgcc ctctactc                                                   18

<210> SEQ ID NO 66
<211> LENGTH: 16
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 66
ggcgaagctg gcaacg                                                    16

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gggcaaacta gtctcgtaat atat                                           24

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
cggaattggt aatcgaaatt                                                20

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gctccttcgc cgtttagtgt atag                                           24

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
cgaaatctct gagaggatcg attg                                           24
```

SOYBEAN EVENT 127 AND METHODS RELATED THERETO

CROSS-REFERENCE TO RELATED APPLICATIONS

This application is a National Stage application of International Application No. PCT/US2010/020252, filed Jan. 6, 2010, which claims the benefit of U.S. Provisional Application No. 61/143,049, filed Jan. 7, 2009, the entire contents of which are hereby incorporated by reference herein.

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "13783US.txt" created on Dec. 30, 2011 and is 45,761 bytes in size. The sequence listing contained in this .txt file is part of the specification and is hereby incorporated by reference herein in its entirety.

FIELD

The invention relates generally to molecular biology and to compositions and methods for increasing tolerance of plants to acetohydroxyacid synthase-inhibiting herbicides and compositions and methods for weed control.

BACKGROUND

Soybean (*Glycine max*) is an important crop in many areas of the world. Biotechnological methods have been applied to soybean for improvement of the agronomic traits and the quality of the product. One such agronomic trait important in soybean production is herbicide tolerance, in particular, tolerance to glyphosate herbicide. As use of glyphosate tolerant soybeans has grown, weeds that are tolerant to glyphosate have emerged. Thus, there is a need for soybean plants that have tolerance to herbicides other than glyphosate for managing weeds.

The phenotypic expression of a transgene (such as those providing herbicide tolerance) in a plant, such as soybean, is affected by both the structure of the gene itself and by its location of integration in the plant genome. At the same time the presence of the transgene (in a foreign DNA) at different locations in the genome will influence the overall phenotype of the plant in different ways. The agronomically or industrially successful introduction of a commercially interesting trait in a plant by genetic manipulation can be a lengthy procedure dependent on different factors. The actual transformation and regeneration of genetically transformed plants are only the first in a series of selection steps, which include extensive genetic characterization, breeding, and evaluation in field trials, eventually leading to the selection of an elite event.

The ability to clearly detect and/or identify particular transgenic events is becoming increasingly important because of the increased use of genetic modification in crop improvement, to improve introgression of transgenes into commercial varieties, for segregation of GMO and non-GMO products, and the identification of proprietary material. There remains a need for the development of methods that are both quick and simple, without the need for an extensive laboratory set-up, for the detection of particular transgenic events. In addition, methods for detecting a particular event would be helpful for complying with regulations requiring the pre-market approval and labeling of foods derived from recombinant crop plants, or for use in environmental monitoring, monitoring traits in crops in the field, or monitoring products derived from a crop harvest, as well as, for use in ensuring compliance of parties subject to regulatory or contractual terms.

SUMMARY

In one embodiment, the present invention provides methods for controlling weeds in a cultivated area, comprising: applying an effective amount of a non-selective herbicide to the cultivated area having a soybean plant comprising an event 127 nucleic acid molecule.

In another embodiment, the present invention provides methods for controlling glyphosate tolerant weeds in a crop field, comprising: applying an effective amount of an AHAS-inhibiting herbicide to the crop field having a soybean plant comprising an event 127 nucleic acid molecule.

In still another embodiment, the present invention provides an isolated nucleic acid molecule having the nucleic acid sequence of positions 1312 to 6069 of SEQ ID NO:1.

In another embodiment, the present invention also provides transgenic soybean plants having a heterologous nucleic acid molecule having the nucleic acid sequence of nucleotides 1302 to 6079 of SEQ ID NO:1.

The present invention also provides an isolated pair of nucleic acid primers comprising: a first and a second isolated nucleic acid molecule capable of amplifying an event 127 nucleic acid molecule.

In another embodiment, the present invention provides a kit for identifying an event 127 nucleic acid molecule in a biological sample, comprising: a first and a second nucleic acid primer, wherein the first and second nucleic acid primers are capable of amplifying an event 127 nucleic acid molecule.

The present invention also provides methods for identifying an event 127 soybean plant, comprising: (a) forming a mixture comprising a biological sample containing soybean DNA and a first and second nucleic acid primer capable of amplifying an event 127 specific nucleic acid molecule; (b) reacting the mixture under conditions that allow the first and second nucleic acid primers to amplify an event 127 specific nucleic acid molecule; and (c) detecting the presence of the amplified fragment nucleic acid molecule, wherein the presence of the soybean event 127 specific nucleic acid molecule indicates that the soybean plant is an event 127 soybean plant.

In still a further embodiment, the present invention provides methods for identifying a soybean plant having an event 127 nucleic acid molecule, comprising: (a) forming a mixture comprising a biological sample containing soybean DNA and a nucleic acid molecule probe that is capable of hybridizing to an event 127 specific nucleic acid molecule; (b) reacting the mixture under conditions that allow the nucleic acid molecule probe to hybridize to an event 127 specific nucleic acid molecule; and (c) detecting hybridization of the probe to the DNA, wherein the presence of hybridization of the nucleic acid molecule probe to the soybean DNA indicates the presence of an event 127 nucleic acid molecule.

The present invention further provides methods for increasing yield in a soybean plant comprising an event 127 nucleic acid molecule, the method comprising: applying an effective amount of an AHAS-inhibiting herbicide to one or more soybean plants comprising an event 127 nucleic acid molecule and the surrounding area, wherein the AHAS-inhibiting herbicide reduces weed growth in the surrounding area; and harvesting seed from the one or more soybean plants.

In another embodiment, the present invention provides methods for breeding an AHAS-inhibiting-herbicide-resistant soybean plant, comprising: (a) crossing a soybean plant comprising an event 127 nucleic acid molecule with a second soybean plant; (b) obtaining seed from the cross of step (a); (c) obtaining a DNA sample from the seed; and (d) detecting the presence of an event 127 nucleic acid molecule in the sample, where the presence of the event 127 nucleic acid molecule indicates that the seed is capable of producing an AHAS-inhibiting-herbicide-resistant soybean plant.

The present invention also provides a seed of a soybean plant comprising an event 127 nucleic acid molecule.

In still another embodiment, the present invention provides methods for detecting the presence of an event 127 nucleic acid molecule in a biological sample, comprising: (a) forming a mixture comprising a biological sample containing DNA and a first and second nucleic acid primer capable of amplifying an event 127 specific nucleic acid molecule; (b) reacting the mixture under conditions that allow the first and second nucleic acid primers to amplify the nucleic acid molecule comprising an event 127 specific nucleic acid molecule; and (c) detecting the presence of the amplified nucleic acid molecule, wherein the presence of the event 127 specific nucleic acid molecule indicates that the sample contains event 127 nucleic acid molecule.

In another embodiment, the present invention provides methods for detecting an event 127 nucleic acid molecule in a biological sample comprising: (a) forming a mixture comprising a biological sample containing DNA and a nucleic acid probe capable of hybridizing to an event 127 specific nucleic acid molecule; (b) reacting the mixture under conditions that allow the probe to hybridize to an event 127 specific nucleic acid molecule; and (c) detecting the presence of a hybridized nucleic acid molecule, wherein the presence of the event 127 specific nucleic acid molecule indicates that the sample contains event 127 nucleic acid molecule.

The present invention also provides methods for detecting the presence of an event 127 insert nucleic acid molecule in a biological sample, comprising: (a) forming a mixture comprising a biological sample containing DNA and a first and a second primer capable of amplifying an event 127 insert nucleic acid molecule; (b) reacting the mixture under conditions that allow the first and second nucleic acid primers to amplify the nucleic acid molecule comprising an event 127 insert nucleic acid molecule; and (c) detecting the presence of the amplified nucleic acid molecule, wherein the presence of the event 127 insert nucleic acid molecule indicates that the sample contains event 127 insert DNA.

In yet another embodiment, the present invention provides methods for detecting the presence of an event 127 insert nucleic acid molecule in a biological sample, comprising: (a) forming a mixture comprising a biological sample containing DNA and a first primer capable of annealing to a region of the event 127 insert nucleic acid molecule and a second primer capable of annealing to a flanking nucleic acid molecule in a host cell genome; (b) reacting the mixture under conditions that allow the first and second nucleic acid primers to produce an amplified nucleic acid molecule comprising a fragment of the event 127 insert nucleic acid molecule; and (c) detecting the presence of the amplified nucleic acid molecule, wherein the presence of the fragment of the event 127 insert nucleic acid molecule indicates that the sample contains event 127 insert DNA.

In another embodiment, the present invention provides methods for growing a soybean plant, comprising: (a) providing a soybean seed comprising an event 127 nucleic acid molecule; (b) planting the soybean seed in a growth medium under conditions that allow the seed to germinate to produce a growing soybean plant comprising an event 127 nucleic acid molecule; and (c) contacting the growth medium, seed, or plant with an herbicidal composition comprising at least one component selected from the group consisting of imidazolinone herbicides, sulfonylurea herbicides, combinations thereof with one another, and combinations thereof with at least one other active ingredient.

In still another embodiment, the present invention provides methods for detecting an event 127 polypeptide in a sample, comprising: obtaining a biological sample from a soybean plant; and conducting at least one immunological assay on the sample, wherein the assay is capable of detecting an event 127 polypeptide.

The present invention also provides devices for use in detecting biological molecules, comprising: a solid support having a surface; and at least one event 127 diagnostic molecule attached to the surface of the solid support.

BRIEF DESCRIPTION OF THE DRAWINGS

FIGS. 4A-4C provide the results of a Southern blot hybridization of the insert copy number in one example of a soybean event 127 plant as described in Example 3.

FIG. 5 provides the results of a Southern blot hybridization showing the absence of vector backbone sequence in one example of a soybean event 127 plant as described in Example 3. FIG. 5A provides the results using probe VP1, and FIG. 5B provides the results using probe VP2. FIG. 5C provides a schematic representation of the relative locations of the regions of hybridization on the 127 event sequence.

FIG. 6 provides the results of a Southern blot hybridization analysis of the intergenerational stability of the event 127 sequence. FIG. 6A provides the results using a 5' UTR probe. FIG. 6B provides the results using an AHAS probe. FIG. 6C provides the results using a 3' UTR probe.

FIG. 8 provides the full length nucleic acid sequence for a soybean event 127 insert and flanking region (SEQ ID NO: 1). Positions 1-1311 represent the 5' flanking DNA, positions 1312-6069 represent the insert DNA encoding a modified AHASL protein, and positions 6070-10,656 represent the 3' flanking DNA.

FIG. 12 provides the DNA used to generate event 127, i.e., the 6156 bp PvuII fragment from the pAC321 construct (SEQ ID NO:4)

DETAILED DESCRIPTION

Figure 1A:
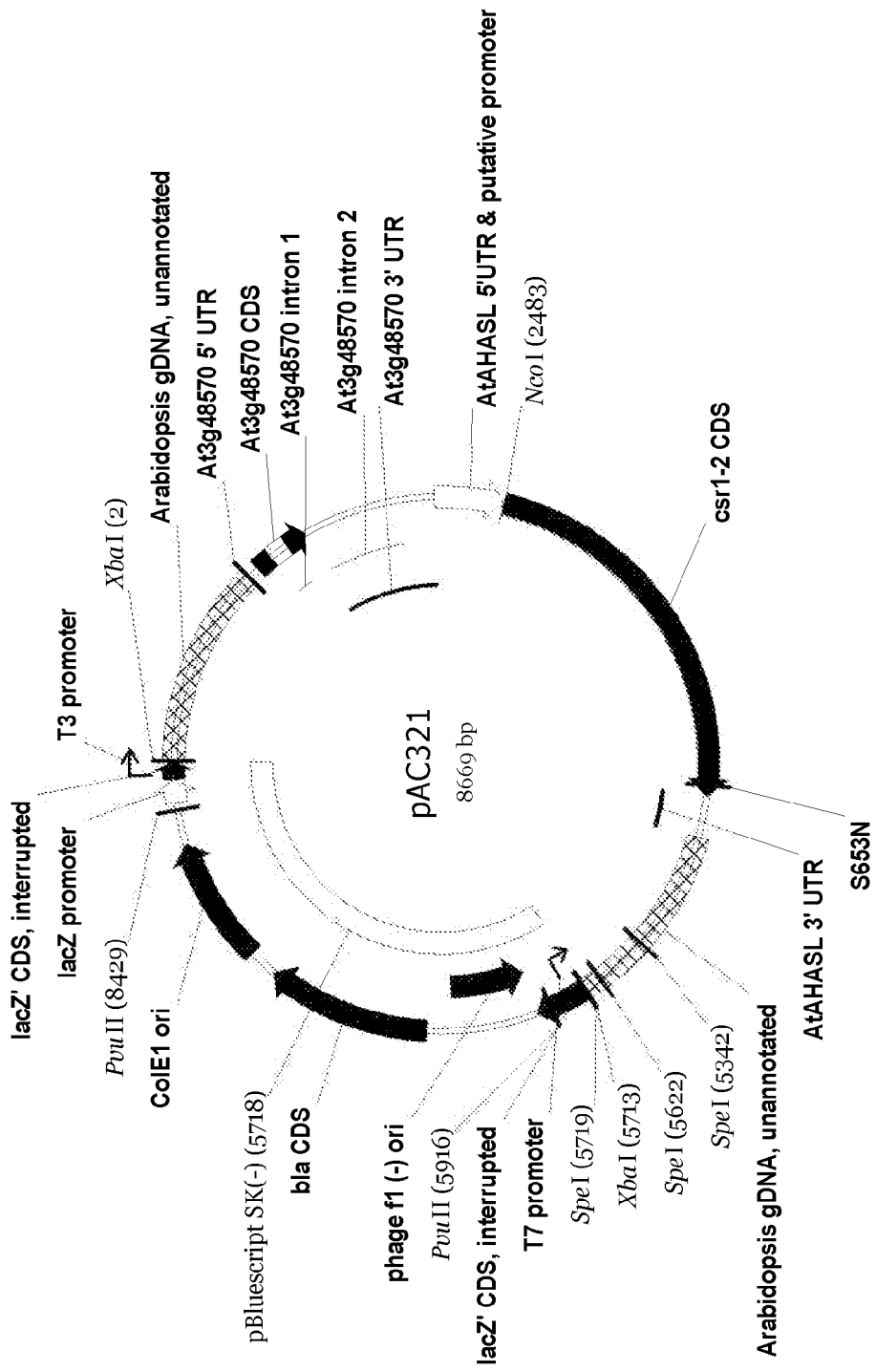
FIG. 1A provides a schematic representation of the plasmid pAC321.

The present invention provides soybean plants that demonstrate tolerance to AHAS-inhibiting herbicides such as imidazolinone herbicides, sulfonylurea herbicides, triazolopyrimidine sulfoanilide herbicides, and/or pyrimidyl oxybenzoate herbicides. The soybean plants of the present invention contain an inserted nucleic acid molecule that is located at a characterized position in the soybean genome. Also provided are methods and compositions for use with the disclosed soybean plants.

Prior to describing the invention in further detail, the following terms will first be defined.

I. DEFINITIONS

As used herein, the terms "soybean" and "soybean plants" means *Glycine max* plants and includes all plant varieties that can be bred with soybean. The term "soybean plant" includes plant parts. As used herein, the term "plant part" includes plant cells, plant organs, plant protoplasts, plant cell tissue cultures from which plants can be regenerated, plant calli, plant clumps, and plant cells that are intact in plants or parts of plants such as embryos, pollen, ovules, seeds, seed pods, leaves, flowers, branches, fruit, stalks, roots, root tips, anthers, cotyledons, hypocotyls, and the like. Grain is intended to mean the mature seed produced by commercial growers for purposes other than growing or reproducing the species. Progeny, derivatives, variants, and mutants of the regenerated plants are also included within the scope of the invention, provided that these parts comprise an event 127 nucleic acid molecule.

An "event 127 nucleic acid molecule" refers to a nucleic acid molecule that comprises a nucleic acid sequence from positions 1312-6069 of SEQ ID NO:1; a variant thereof obtained by traditional plant breeding that provides for the expression of a modified form of the AHAS enzyme having an AHASL protein containing an asparagine corresponding to position 653, rather than the natural serine (S653N), where the modified form of the AHAS enzyme exhibits tolerance to an AHAS inhibitor that would normally inhibit the enzymatic activity of the wild-type AHAS enzyme; or the complement of any of these. The event 127 nucleic acid molecule may contain additional sequences that flank positions 1312-6069 of SEQ ID NO:1 (or, for variants, additional sequences that flank the 5' and 3' positions).

An "event 127 region" refers to a nucleic acid molecule that includes at least a fragment of an event 127 nucleic acid molecule and that is indicative of an event 127 plant. An event 127 region can include one or more of the, 5' and/or 3' junction regions, insert DNA, or the junction region of the insert DNA's csr1-2 duplication with the remainder of the insert DNA, Also, 5' and/or 3' flanking sequence DNA can further be included therein.

As used herein, the term "event 127 specific nucleic acid molecule" refers to a nucleic acid molecule sequence which discriminatively identifies or which is capable of discriminatively identifying event 127 nucleic acid molecules in a sample. Event 127 specific nucleic acid molecules may include junction regions and unique mutations or duplications in the insert DNA resulting from the transformation event. For example, the use of PCR primers having the nucleic acid sequence of SEQ ID NOs:37 and 38 in a PCR reaction results in the amplification of an amplicon that is indicative of an event 127 nucleic acid molecule.

An "event 127 molecule" refers to nucleic acid molecules, polypeptide molecules and other biological molecules that are derived from, obtained from, or encoded by an event 127 nucleic acid molecule.

An "event 127 diagnostic molecule" refers to molecules that can be used to detect, either directly or indirectly an event 127 nucleic acid molecule. Event 127 diagnostic molecules include nucleic acid molecules, such as primers and probes, antibodies and their binding-site-retaining fragments (e.g. Fv, Fab, Fab', F(ab'), and H-domain-deleted antibodies), polypeptides, and derivatives thereof, nucleic acid analogs, aptamers, and the like that can be used in methods for detecting event 127 nucleic acid molecules or polypeptides expressed from such nucleic acid molecules.

As used herein, "insert DNA" refers to the heterologous DNA introduced to plant material via the transformation process and includes DNA which differs from the original DNA used for such transformation as explained herein. "Event 127 insert nucleic acid" and "event 127 insert DNA" refer to a nucleic acid molecule having the nucleic acid sequence of positions 1312-6069 of SEQ ID NO:1 (which differs from the DNA used to generate event 127, i.e., the 6156 bp PvuII fragment from the pAC321 construct provided in FIG. 12 (SEQ ID NO:4)).

An "event 127" plant, cell, seed, plant part or plant tissue refers to any plant, cell, seed, plant part or plant tissue that contains an event 127 nucleic acid molecule, and preferably contain at least one event 127 specific nucleic acid. Event 127 plants include event 127-9 soybean plants containing a nucleic acid molecule having the sequence of SEQ ID NO:1 such as those referred to as BPS-CV 127-9.

The term "flanking DNA" refers to genomic DNA naturally present in an organism, such as a plant, immediately upstream or downstream and contiguous with the inserted nucleic acid molecule. A "flanking region" or "flanking sequence" as used herein refers to a sequence of at least 10, 20, 50, 100, 200, 300, 400, 1000, 1500, 2000, 2500, or 5000 base pairs or greater which is located either immediately upstream (5') of and contiguous with or immediately downstream (3') of and contiguous with the original foreign insert DNA molecule. Non-limiting examples of the flanking regions of event 127 are set forth in SEQ ID NOs:2 and 3 and variants and fragments thereof, wherein SEQ ID NO:2 represents positions 1-1311 of SEQ ID NO:1, and SEQ ID NO:3 represents positions 6070-10,656 of SEQ ID NO:1.

Transformation procedures leading to random integration of the foreign insert DNA will result in individual transformants containing different flanking regions characteristic of and unique for each transformant. When recombinant DNA is introduced into a plant through traditional crossing, its flanking regions will generally not be changed from that of the original transformant. Individual transformation events will also contain unique junctions between a piece of heterologous insert DNA and genomic DNA, or two pieces of genomic DNA, or two pieces of heterologous DNA.

A "junction point" is a point where two specific DNA fragments join, for example, where insert DNA joins flanking DNA. A junction point also exists in a transformed organism where two DNA fragments join together in a manner that is modified from that found in the native organism. As used herein, "junction DNA" or "junction region" refers to DNA that comprises a junction point. Non-limiting examples of junction points in DNA from the soybean event 127 include sequences as set forth, for example, in SEQ ID NOs:5 and 6, wherein SEQ ID NO:5 represents positions 1311-1312 of SEQ ID NO:1 and SEQ ID NO:6 represents positions 6069-6070 of SEQ ID NO:1.

It is to be understood that as used herein the term "transgenic" includes any cell, cell line, callus, tissue, plant part, or plant, the genotype of which has been altered by the presence of a heterologous nucleic acid including those transgenics initially so altered as well as those created by sexual crosses or asexual propagation from the initial regenerated event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include those known in the art and disclosed below.

A "transgenic event" is produced by transformation of plant cells with a heterologous DNA construct(s), including a nucleic acid expression cassette that comprises a transgene of interest, the regeneration of a population of plants resulting from the insertion of the transgene into the genome of the plant, and selection of a particular regenerated plant characterized by insertion into a particular genome location. An event is characterized phenotypically by the expression of the transgene(s). At the genetic level, an event is part of the genetic makeup of a plant.

As used herein, a "sample" includes any sample that contains nucleic acid molecules or polypeptides and is derived from plants, plant material, or in products such as, but not limited to, food or feed products (fresh or processed) comprising, or derived from plant material.

By "introducing" or "introduced" in the context of transformation is intended presenting to the plant a heterologous DNA construct in such a manner that the construct gains access to the interior of a cell of the plant. The plants and methods of the invention do not depend on a particular method for introducing a nucleic acid construct to a plant, only that the nucleic acid construct gains access to the interior of at least one cell of the plant. Methods for introducing nucleic acid constructs into plants are known in the art including, but not limited to, stable transformation methods, transient transformation methods, and virus-mediated methods.

The term "progeny" refers to plants produced by a sexual cross (e.g. outcross, self-cross or back-cross) between an event 127 plant and another variety. Even after repeated backcrossing to a recurrent parent, the inserted DNA and/or flanking DNA from the event 127 parent is present in the progeny of the cross at the same chromosomal location and can be identified, for example, by screening for event 127 specific regions.

As used herein, "heterologous" in reference to a nucleic acid molecule is a nucleic acid molecule that originates from a foreign species, or, if from the same species, is modified from its native form in composition and/or genomic locus by deliberate human intervention.

An "isolated" or "purified" nucleic acid molecule, or biologically active portion thereof, is substantially or essentially free from components that normally accompany or interact with the nucleic acid molecule as found in its naturally occurring environment. Thus, an isolated or purified nucleic acid molecule is substantially free of other cellular material, or culture medium when produced by recombinant techniques, or substantially free of chemical precursors or other chemicals when chemically synthesized.

A "probe" refers to an isolated nucleic acid molecule to which is attached a detectable label or reporter molecule, e.g., a radioactive isotope, ligand, chemiluminescent agent, enzyme, etc. Such a probe is complementary to a strand of a target nucleic acid molecule, in the instant case, to a strand of isolated DNA from soybean event 127 plant biological material whether from a soybean plant or from a sample that includes DNA from the event. Probes include not only deoxyribonucleic or ribonucleic acids but also polyamides and other probe materials that can specifically detect the presence of the target DNA sequence.

As used herein, "primers" are isolated nucleic acid molecules that are capable of annealing to a complementary target DNA strand by nucleic acid hybridization to form a hybrid between the primer and the target DNA strand, which can then be extended along the target DNA strand by a polymerase, e.g., a DNA polymerase. "Primer pairs" refer to a pair of primers for use in amplification of a target nucleic acid molecule, e.g., by the polymerase chain reaction (PCR) or other conventional nucleic-acid amplification methods. "Polymerase chain reaction" or "PCR" is a technique used for the amplification of specific DNA segments.

A "line" or "strain" is a group of individuals of identical parentage that are generally inbred to some degree and that are generally isogenic or near isogenic.

The term "crossed" or "cross" in the context of this invention means the fusion of gametes, e.g., via pollination to produce progeny (i.e., cells, seeds, or plants) in the case of plants. The term encompasses both sexual crosses (the pollination of one plant by another) and, in the case of plants, selfing (self-pollination, i.e., when the pollen and, ovule are from the same plant).

The term "introgression" refers to the transmission of a desired allele of a genetic locus from one genetic background to another. In one method, the desired alleles can be introgressed through a sexual cross between two parents, wherein at least one of one of the parents has the desired allele in its genome.

II. SOYBEAN EVENT 127 PLANTS

Compositions and methods related to transgenic AHAS inhibitor-tolerant soybean plants are provided. Such compositions include event 127 soybean plants. An event 127 soybean plant has been modified from a wild-type or non-transformed soybean plant by the insertion or introgression of the imidazolinone-tolerant acetohydroxyacid synthase large subunit gene from *Arabidopsis thaliana* (csr1-2) into the soybean genome as defined herein. In some embodiments, the insertion of the csr1-2 gene into the soybean genome provides for the expression of a modified form of the acetohydroxyacid synthase (AHAS) enzyme having an AHASL protein containing an asparagine corresponding to position 653, rather than the natural serine (S653N). The AHAS enzyme is important for branched chain amino acid biosynthesis and is inhibited by certain herbicides (AHAS-inhibiting herbicides). The modification in the AHAS gene overcomes this inhibition and thus provides tolerance to a wide range of AHAS-inhibiting herbicides. Thus, a soybean event 127 plant is tolerant to at least one AHAS-inhibiting herbicide or is tolerant of increased amounts of at least one AHAS-inhibiting herbicide compared to a soybean plant lacking an event 127 nucleic acid molecule.

The nucleic acid molecule conferring the AHAS inhibitor tolerance was found to be inserted at a characterized position in the soybean genome and thereby produces the 127 event. The event 127 soybean plant harboring an event 127 nucleic acid molecule at the recited chromosomal location comprises, in one embodiment, one or more genomic/transgene junctions having at least the nucleic acid molecule sequence of SEQ ID NO:5 and/or 6. The characterization of the genomic insertion site of the event 127 provides for an enhanced breeding efficiency and enables the use of molecular markers to track the transgene insert in the breeding populations and progeny thereof. Various methods and compositions for the identification, detection, and use of the event 127 soybean plants are provided herein.

The csr1-2 expression cassette, a PvuII fragment from plasmid pAC321, was integrated at a single characterized genetic locus in the soybean genome to result in event 127. In one embodiment, the inserted csr1-2 cassette in event 127 contains three point mutations relative to the original transformation fragment from plasmid pAC321 with one mutation in the AHAS coding sequence and the other two downstream of the AHASL 3' untranslated region (UTR). Such mutations include a G to A mutation in the coding sequence, which results in the expression of an AHAS polypeptide having an amino acid substitution of $R_{272}$ to $K_{272}$. Southern blot analysis and sequence verification of the point mutation indicate that the insert is stable across at least eight generations. The inserted DNA in event 127 also contains a 376 base pair (bp) duplication of a portion of the csr1-2 coding sequence directly before the 3' integration point (the duplication is represented by positions 5694-6069 of SEQ ID NO:1). This duplicated 376 bp segment results in a 501 bp open reading frame (ORF) that extends into the 3' flanking sequence. Reverse transcription-polymerase chain reaction (RT-PCR) results suggest that this 501 bp ORF is not transcribed. In some embodiments, the event 127 nucleic acid molecule also contains the majority of the *Arabidopsis* SEC61γ subunit gene locus (At3g48570), which is a component of the DNA fragment used for transformation. In other embodiments, the SEC61γ subunit gene may be expressed in a Soybean event 127 plant. For example, as disclosed in more detail in the Examples below, RT-PCR experiments show that the *Arabidopsis* SEC61γ subunit gene is weakly transcribed in event 127 leaf tissue. A total of about 1.3 kilobases (kb) of 5' flanking soybean DNA has been sequenced together with about 4.6 kb of 3' flanking soybean DNA. The flanking sequence information can be used in the development of an event 127-specific qualitative PCR detection method in accordance with the present invention. Other characteristics of the event 127 nucleic acid molecules, such as the identified point mutations and duplications, can also be used in methods provided herein for the detection of an event 127 plant, including progeny and derivatives thereof.

The event 127 plants of the present invention are tolerant to application of AHAS-inhibiting herbicides. The event 127 plants exhibit tolerance or enhanced tolerance to levels of AHAS-inhibiting herbicides at levels of application that include amounts equivalent to amounts of herbicide application between 50 g ai/ha and about 500 g ai/ha, between 70 g ai/ha and about 400 g ai/ha, and between 70 g ai/ha and about 300 g ai/ha. Such tolerance can also include tolerance to levels of AHAS-inhibiting herbicides of 1×, 2×, 3×, 4×, 5×, or greater amounts of the commercial levels of applications of the herbicide.

Tolerance to an AHAS-inhibiting herbicide can be determined by any method of determining herbicide tolerance. For example, a soybean event 127 plant can demonstrate tolerance to an AHAS-inhibiting herbicide or other chemical if it shows damage in comparison to an appropriate control plant that is less than the damage exhibited by the control plant by at least 5%, 10%, 15%, 20%, 25%, 30%, 35%, 40%, 45%, 50%, 55%, 60%, 65%, 70%, 75%, 80%, 90%, 100%, 150%, 200%, 250%, 300%, 400%, 500%, 600%, 700%, 800%, 900%, or 1000% or more. In this manner, a plant that is tolerant to an AHAS-inhibiting herbicide or other chemical shows "improved tolerance" in comparison to an appropriate control plant. Damage resulting from the herbicide or other chemical treatment is assessed by evaluating any parameter of plant growth or well-being deemed suitable by one of skill in the art. Damage can be assessed by visual inspection and/or by statistical analysis of suitable parameters of individual plants or of a group of plants. Thus, damage can be assessed by evaluating, for example, parameters such as plant height, plant weight, leaf color, flowering, fertility, yield, seed production, and the like. Damage can also be assessed by evaluating the time elapsed to a particular stage of development (e.g., maturity or flowering) or the time elapsed until a plant has recovered from treatment with a particular chemical and/or herbicide.

Damage caused by an AHAS-inhibiting herbicide or other chemical can be assessed at various times after an event 127 plant has been treated or contacted with an herbicide. The damage can be assessed at about the time that the control plant exhibits maximum damage, or can be assessed after a period of time in which a control plant that was not treated with the herbicide or other chemical has measurably grown and/or developed in comparison to the size or stage at which the treatment was administered. In addition, the damage can be assessed at various times, for example, at 12 hours or at 1, 2, 3, 4, 5, 6, 7, 8, 9, 10, 11, 12, 13, 14 days, or three weeks, four weeks, or longer after the test plant was treated with the herbicide. Any time of assessment is suitable as long as it permits detection of a difference in response to a treatment of test and control plants.

The present invention further includes seed of soybean line CV603 (also known as "BPS-CV127-9") containing event 127 nucleic acid molecules, and deposited as NCIMB Patent Deposit No. 41603 and plants, plant cells, and seed derived therefrom. Applicant(s) have made a deposit of at least 2500 seeds of soybean plants containing an event 127 nucleic acid molecule with the National Collections of Industrial, Food, and Marine Bacteria (NCIMB), 23 St. Machar Drive, Aberdeen AB2 1RY, Scotland, United Kingdom, on Dec. 22, 2008, and the deposit was assigned NCIMB accession No. 41603. These deposits will be maintained under the terms of the Budapest Treaty on the International Recognition of the Deposit of Microorganisms for the Purposes of Patent Procedure. This deposit was made merely as a convenience for those of skill in the art and are not an admission that a deposit is required under 35 U.S.C. §112. The seeds deposited with the NCIMB on Dec. 22, 2008 were taken from the deposit maintained by Embrapa (Empresa Brasileira de Pesquisa Agropecuaria). Access to this deposit will be available during the pendency of the application to the Commissioner of Patents and Trademarks and persons determined by the Commissioner to be entitled thereto upon request. Upon allowance of any claims in the application, the Applicant(s) will make available to the public, pursuant to 37 C.F.R. §1.808, sample(s) of the deposit of at least 2500 seeds of soybean plants containing an event 127 nucleic acid molecule with the National Collections of Industrial, Food, and Marine Bacteria (NCIMB), 23 St. Machar Drive, Aberdeen AB2 1RY, Scotland, United Kingdom. This deposit of soybean line CV603 seed will be maintained in the NCIMB depository, which is a public depository, for a period of 30 years, or 5 years after the most recent request, or for the enforceable life of the patent, whichever is longer, and will be replaced if it becomes nonviable during that period. Additionally, Applicant(s) have satisfied all the requirements of 37 C.F.R. §§1.801-1.809, including providing an indication of the viability of the sample upon deposit. Applicant(s) have no authority to waive any restrictions imposed by law on the transfer of biological material or its transportation in commerce. Applicant(s) do not waive any infringement of their rights granted under this patent or rights applicable to soybean line CV603 under the Plant Variety Protection Act (7 USC 2321 et seq.). Unauthorized seed multiplication prohibited. The seed may be regulated.

Event 127 soybean plants of the present invention also include progeny, derivatives, variants, and mutants of the initial transformation event giving rise to event 127 soybean plants. Such plants may be identified using any method for identifying such plants, including, but not limited to, breeding records, herbicide tolerance methods, molecular detection methods, the methods disclosed herein, and combinations thereof.

The event 127 soybean plants of the present invention are tolerant to at least one herbicide that interferes with the activity of the endogenous AHAS enzyme (AHAS-inhibiting herbicides) lacking the S653N mutation. Herbicides that interfere with the activity of the AHAS enzyme include imidazolinone herbicides, sulfonylurea herbicides, triazolopyrimidine herbicides, pyrimidinyloxybenzoate herbicides, sulfonylamino-carbonyltriazolinone herbicides, or mixtures or combinations thereof. In one embodiment such herbicides are an imidazolinone herbicide, a sulfonylurea herbicide, or mixtures thereof. Imidazolinone herbicides include, but are not limited to, PURSUIT® (imazethapyr), CADRE® (imazapic), RAPTOR® (imazamox), SCEPTER® (imazaquin), ASSERT® (imazethabenz), ARSENAL® (imazapyr), a derivative of any of the aforementioned herbicides, and a mixture or combination of two or more of the aforementioned herbicides, for example, imazapyr/imazamox (ODYSSEY®). The imidazolinone herbicide can also be selected from, but not limited to, 2-(4-isopropyl-4-methyl-5-oxo-2-imidiazolin-2-yl)-nicotinic acid, [2-(4-isopropyl)-4-][methyl-5-oxo-2-imidazolin-2-yl)-3-quinolinecarboxylic]acid, [5-ethyl-2-(4-isopropyl-]-4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, [2-(4-isopropyl-4-methyl-5-oxo-2-]imidazolin-2-yl)-5-methylnicotinic acid, and a mixture of methyl[6-(4-isopropyl-4-]methyl-5-oxo-2-imidazolin-2-yl)-m-toluate and methyl[2-(4-isopropyl-4-methyl-5-]oxo-2-imidazolin-2-yl)-p-toluate. In one embodiment 5-ethyl-2-(4-isopropyl-4-methyl-5-oxo-2-imidazolin-2-yl)-nicotinic acid and [2-(4-isopropyl-4-methyl-5-oxo-2-imidazolin-2-]yl)-5-(methoxymethyl)-nicotinic acid are used. In another embodiment, [2-(4-isopropyl-4-]methyl-5-oxo-2-imidazolin-2-yl)-5-(methoxymethyl)-nicotinic acid is used.

Sulfonylurea herbicides that can be used in the present invention include, but are not limited to, chlorsulfuron, metsulfuron methyl, sulfometuron methyl, chlorimuron ethyl, thifensulfuron methyl, tribenuron methyl, bensulfuron methyl, nicosulfuron, ethametsulfuron methyl, rimsulfuron, triflusulfuron methyl, triasulfuron, primisulfuron methyl, cinosulfuron, amidosulfiuon, fluzasulfuron, imazosulfuron, pyrazosulfuron ethyl, halo sulfuron, azimsulfuron, cyclosulfuron, ethoxysulfuron, flazasulfuron, flupyrsulfuron methyl, foramsulfuron, iodosulfuron, oxasulfuron, mesosulfuron, prosulfuron, sulfosulfuron, trifloxysulfuron, tritosulfuron, a derivative of any of the aforementioned herbicides, and a mixture of two or more of the aforementioned herbicides. The triazolopyrimidine herbicides of the invention include, but are not limited to, cloransulam, diclosulam, florasulam, flumetsulam, metosulam, and penoxsulam. The pyrimidinyloxybenzoate (or pyrimidinyl carboxy) herbicides of the invention include, but are not limited to, bispyribac, pyrithiobac, pyriminobac, pyribenzoxim and pyriftalid. The sulfonylamino-carbonyltriazolinone herbicides include, but are not limited to, flucarbazone and propoxycarbazone.

It is recognized that pyrimidinyloxybenzoate herbicides are related to the pyrimidinylthiobenzoate herbicides and can be generalized under the heading of pyrimidinylthiobenzoate herbicides by the Weed Science Society of America. Accordingly, the herbicides of the present invention further include pyrimidinylthiobenzoate herbicides, including, but not limited to, the pyrimidinyloxybenzoate herbicides described above.

III. NUCLEIC ACID MOLECULES

The present invention also provides isolated event 127 nucleic acid molecules. As used herein, the use of the term "nucleic acid molecule" is not intended to limit a nucleic acid molecule to comprise DNA, but can include any nucleotides, such as ribonucleotides and combinations of ribonucleotides and deoxyribonucleotides. Such deoxyribonucleotides and ribonucleotides include both naturally occurring molecules and synthetic analogues. The nucleic acid molecules also encompass all forms of sequences including, but not limited to, single-stranded forms, double-stranded forms, hairpins, stem-and-loop structures, and the like. In one embodiment, the event 127 nucleic acid molecule comprises a nucleic acid molecule having the nucleic acid sequence of positions 1312 to 6069 of SEQ ID NO:1. In another embodiment, the event 127 nucleic acid molecule comprises a nucleic acid molecule having the sequence of nucleotides 1302 to 6079 of SEQ ID NO:1.

The event 127 nucleic acid molecules also include fragments of SEQ ID NO:1. "Fragments" of a nucleotide sequence can be of any length, such as for example, at least 7, 15, 20, 25, 30, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or more nucleotides (nt) in length. These fragments have numerous uses that include, but are not limited to, diagnostic probes and primers. Of course, larger fragments, such as those of 601-8000 nt in length are also useful according to the present invention as are fragments corresponding to most, if not all, of the nucleotide sequences SEQ ID NO: 1. By a fragment at least 20 nt in length, for example, is intended fragments which include 20 or more contiguous bases from, for example, the nucleotide sequence of SEQ ID NO: 1.

An event 127 plant comprises a transgenic expression cassette having an AHASL coding sequence having an S653N mutation that is capable of providing resistance or tolerance to imidazolinone-inhibiting herbicides. The cassette additionally includes 5' and 3' regulatory sequences operably linked to the AHASL coding sequence. "Operably linked" is intended to mean a functional linkage between two or more elements. For example, an operable linkage between a nucleic acid molecule of interest and a regulatory sequence (e.g., a promoter) is a functional link that allows for the expression of the nucleic acid molecule of interest. Operably linked elements may be contiguous or non-contiguous. When used to refer to the joining of two protein coding regions, by operably linked it is intended that the coding regions are in the same reading frame.

Thus, the expression cassette in a soybean event 127 plant contains in the 5'-3' direction of transcription, a transcriptional and translational initiation region (e.g., a promoter), an AHASL S653N coding region, and a transcriptional and translational termination region functional in plants. "Promoter" refers to a nucleotide sequence capable of controlling the expression of a coding sequence or functional RNA. In general, a coding sequence is located 3' to a promoter sequence. The promoter sequence can comprise proximal and more distal upstream elements, the latter elements are often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters".

In one embodiment, the expression cassette in a soybean event 127 plant contains, as operably linked components, an AHASL S653N encoding sequence under the control of the *Arabidopsis thaliana* csr1-2 promoter and the csr1-2 transcription termination region. The expression cassette is derived as a PvuII fragment from the nucleic acid construct pAC321. In one embodiment, the expression cassette has the sequence of SEQ ID NO:4.

Isolated nucleic acid molecules are provided that can be used in various methods for the detection and/or identification of the event 127 nucleic acid molecule. In one embodiment, an "isolated" nucleic acid molecule is free of sequences (e.g. protein encoding sequences) that naturally flank the nucleic acid molecule (i.e., sequences located at the 5' and 3' ends of the nucleic acid) in the genomic DNA of the organism from which the nucleic acid molecule is derived. For example, in various embodiments, the isolated nucleic acid molecule can contain less than about 5 kb, 4 kb, 3 kb, 2 kb, 1 kb, 0.5 kb, or 0.1 kb of nucleotide sequence that naturally flank the nucleic acid molecule in genomic DNA of the cell from which the nucleic acid molecule is derived.

In some embodiments, the nucleic acid molecules comprise the junction DNA sequence set forth in SEQ ID NO:5 and/or 6. In other embodiments, the nucleic acid molecules comprise the junction DNA sequences set forth in SEQ ID NO:5 and/or 6 or variants and fragments thereof. Fragments and variants of junction DNA sequences are suitable for discriminatively identifying event 127 DNA. As discussed elsewhere herein, such sequences find use as primers and/or probes for use in detecting event 127 insert DNA in a sample.

In other embodiments, nucleic acid molecules are provided that can detect an event 127 plant, event 127 insert DNA, or an event 127 specific nucleic acid molecule. Such sequences include any nucleic acid molecule comprising a nucleic acid molecule set forth in SEQ ID NOs:5 and/or 6 or variants thereof or complements thereof. In some embodiments, the nucleic acid molecule used to detect an event 127 nucleic acid molecule comprises the sequence set forth in SEQ ID NO:5 and/or 6 or complements thereof. Fragments and variants of nucleic acid molecules that detect an event 127 nucleic acid molecule, an event 127 insert DNA, or an event 127 specific region are suitable for discriminatively identifying event 127 plants. As discussed elsewhere herein, such sequences find use as primers and/or probes. Further provided are isolated DNA nucleotide primer sequences comprising or consisting of a sequence set forth in SEQ ID NO:35, 36, 37, 38, 39, 40, 41, 42, 43, 44, 45, 47, 67, 68, 69, 70, or a complement thereof or variants and fragments of SEQ ID NO:35, 36, 37, 38, 39, 40, 41, 42, 43, 44, 45, 47, 67, 68, 69, 70, or complements thereof.

In one embodiment, a specific primer pair for use herein comprises the forward and reverse primers shown below (with relative positions to SEQ ID NO:1 identified). The primers are predicted to produce a band size of 327 base pairs.

| Direction | Primer Sequence 5'-3' | Position (SEQ ID NO: 1) | SEQ ID NO: |
|---|---|---|---|
| Forward | GCTCCTTCGCCGTTTAG TGTATAG | 1108-1131 | 69 |
| Reverse | CGAAATCTCTGAGAGGA TCGATTG | 1411-1434 | 70 |

As used herein, "variants" with regard to nucleic acid sequences refers to substantially similar sequences. For nucleic acid molecules, a variant comprises a nucleic acid molecule having deletions (e.g., truncations) at the 5' and/or 3' end; deletion and/or addition of one or more nucleotides at one or more internal sites in the native nucleic acid molecule; and/or substitution of one or more nucleotides at one or more sites in the native nucleic acid molecule.

Any combination of primers can be used in the present invention, such as those disclosed herein, for the detection an event 127 specific region (e.g., SEQ ID NOs:35, 36, 37, 38, 39, 40, 41, 42, 43, 44, 45, 47, 67, 68, 69, and 70). Non-limiting examples of primer pairs include SEQ ID NOs:35 and 36; SEQ ID NOs:37 and 38; SEQ ID NOs:39 and 40; SEQ ID NOs:41 and 42; SEQ ID NOs:43 and 44, SEQ ID NOS: 67 and 68, SEQ ID NOS: 69 and 70. Additional primers and primer pairs can also be designed according to the present invention for use in the disclosed methods.

The probes and primers for use in the methods provided are of sufficient nucleotide length to bind to the target DNA sequence and specifically detect and/or identify a nucleic acid molecule in a biological sample, for example, samples obtained from a plant to be tested. It is recognized that the hybridization conditions or reaction conditions can be determined by the operator to achieve this result. This length can be of any length that is useful in a detection method of choice, such as, 8, 10, 11, 14, 16, 18, 20, 22, 24, 26, 28, 30, 40, 50, 75, 100, 200, 300, 400, 500, 600, 700 nucleotides or more, or between about 11-20, 20-30, 30-40, 40-50, 50-100, 100-200, 200-300, 300-400, 400-500, 500-600, 600-700, 700-800, or more nucleotides in length. Such probes and primers can hybridize specifically to a target sequence under high stringency hybridization conditions. Probes and primers according to embodiments can have complete DNA sequence identity of contiguous nucleotides with the target sequence, although probes differing from the target DNA sequence and that retain the ability to specifically detect and/or identify a target DNA sequence may be designed by conventional methods. Accordingly, probes and primers can share about 80%, 85%, 90%, 91%, 92%, 93%, 94%, 95%, 96%, 97%, 98%, 99% or greater sequence identity or complementarity to the target nucleic acid molecule (e.g., SEQ ID NO:35, 36, 37, 38, 39, 40, 41, 42, 43, 44), or can differ from the target sequence (e.g., SEQ ID NO:35, 36, 37, 38, 39, 40, 41, 42, 43, 44) by 1, 2, 3, 4, 5, 6 or more nucleotides. Probes can be used as primers, but are generally designed to bind to the target DNA or RNA and are not used in an amplification process.

In some embodiments, specific primers can be used to amplify a fragment of the event DNA to produce an amplicon that can be used as a "specific probe" or the amplicon can itself be detected for identifying event 127 nucleic acid molecules in biological samples. Alternatively, a probe can be used during the PCR reaction to allow for the detection of the amplification event (e.g., a Taqman probe or a MGB probe) (so called real time PCR). When a probe is hybridized with nucleic acid molecules in a biological sample under conditions which allow for the binding of the probe to the sample, this binding can be detected and thus allow for an indication of the presence of event 127 in the biological sample. Such identification of a bound probe has been described in the art. In one embodiment, the probe is a sequence which, under optimized conditions, hybridizes specifically to a region including the 5' or 3' flanking region of the event and also includes a part of the insert DNA contiguous therewith, thus spanning a junction region. The specific probe may comprise a sequence of at least 80%, between 80 and 85%, between 85 and 90%, between 90 and 95%, and between 95 and 100% identical (or complementary) to a specific region of the event 127 nucleic acid molecule.

As used herein, "amplified DNA" or "amplicon" refers to the product of nucleic acid molecule amplification of a target nucleic acid molecule that is part of a nucleic acid template. For example, to determine whether a soybean plant resulting from a sexual cross contains the event 127 nucleic acid molecule, DNA extracted from the soybean plant tissue sample may be subjected to a nucleic acid molecule amplification method using a DNA primer pair that includes a first primer derived from flanking sequence adjacent to the insertion site of inserted heterologous DNA, and a second primer derived from the inserted heterologous DNA to produce an amplicon that is diagnostic for or indicative of the presence of the event 127 nucleic acid molecule. By "diagnostic" for an event 127 region the use of any method or assay which discriminates between the presence or the absence of an event 127 region in a biological sample is intended. Alternatively, the second primer may be derived from the flanking sequence. In still other embodiments, primer pairs can be derived from flanking sequence on both sides of the inserted DNA so as to produce an amplicon that includes the entire inserted nucleic acid molecule of the expression construct as well as the sequence flanking the transgenic insert, for example SEQ ID NO:1. The amplicon is of a length and has a sequence that is also diagnostic for the event (e.g., contains a junction DNA from an event 127 region). The amplicon may range in length from the combined length of the primer pairs plus one nucleotide base pair to any length of amplicon producible by a DNA amplification protocol. A member of a primer pair derived from the flanking sequence may be located a distance from the inserted DNA sequence, this distance can range from one nucleotide base pair up to the limits of the amplification reaction, or about twenty thousand nucleotide base pairs. In another embodiment, primer pairs can be designed to amplify the insert DNA, or a fragment of the insert DNA. Such primer pairs are useful to detect the presence of the event 127 insert DNA in a biological sample. The use of the term "amplicon" specifically excludes primer dimers that may be formed in the DNA thermal amplification reaction.

In certain embodiments, useful primer pairs will include one primer that overlaps with the junction point between the insert DNA and the flanking 5' or 3' genomic DNA. Such primers may be designed around the junction point between the 5' flanking DNA and the insert DNA (i.e., the junction between positions 1311 and 1312 of SEQ ID NO:1) as well as around the junction point between the insert DNA and the 3' flanking DNA (i.e., the junction between positions 6069 and 6070 of SEQ ID NO:1). Such primers may be designed to hybridize with about 10 nucleotides from either the flanking region or the insert DNA and with at least 1 nucleotide across the junction point in the insert DNA or the flanking region. Thus, for example, primers may comprise nucleotide sequences designed to hybridize with the nucleotides represented by at least the following positions of SEQ ID NO:1: 1311-1321, 1302-1312, 6060-6070, and/or 6069-6079.

In other embodiments, useful primer pairs will include one primer that overlaps with the junction point between the 5' end of the duplicated portion of the csr1-2 coding sequence of the insert DNA (at position 5694 of SEQ ID NO:1) and the adjacent insert DNA (i.e., at position 5693 of SEQ ID NO:1). Such primers may be designed to hybridize with about 10 nucleotides from either the duplicated region or the adjacent insert DNA and with at least 1 nucleotide across the junction point (e.g., at least 5693-5703, or at least 5684-5694 of SEQ ID NO:1).

Methods for preparing and using probes and primers for use in the present invention are known in the art. PCR primer pairs can be derived from a known sequence, for example, by using computer programs intended for that purpose such as the PCR primer analysis tool in Vector NTI version 6 (Informax Inc., Bethesda Md.); PrimerSelect (DNASTAR Inc., Madison, Wis.); and Primer (Version 0.5©, 1991, Whitehead Institute for Biomedical Research, Cambridge, Mass.). Additionally, the sequence can be visually scanned and primers manually identified using guidelines known to one of skill in the art.

IV. METHODS OF BREEDING

The disclosed event 127 soybean plants can be used in a breeding program using breeding methods to produce additional event 127 soybean plants, such as progeny plants. Such breeding methods can be used to produce soybean plants for example for use in commercial production in different geographic regions or to produce additional soybean breeding populations.

In addition, the event 127 soybean plants may be used in breeding programs using breeding methods to produce soybean plants having additional traits of interest combined with the AHAS-inhibitor tolerance (also referred to as "stacked traits" or "trait stacking"), such as combinations of resistance to additional herbicides, such as glyphosate, glufosinate, and/or dicamba. In addition, the event 127 soybean plants may be used in a breeding program using breeding methods to produce soybean plants having multiple AHAS-inhibiting herbicide resistance coding sequences. Also, the disclosed plants may be used in breeding programs using breeding methods to produce plants having the AHAS-inhibiting herbicide tolerance trait combined with other agronomically important traits, including input traits, (such as disease and pathogen resistance, such as those conferred by the Bt gene), and output traits, such as oil and protein quality and quantity.

The disclosed methods of breeding AHAS-inhibiting herbicide resistant soybean plants, comprise the steps of (a) crossing an event 127 soybean plant with a second soybean plant; and (b) obtaining seed from the cross. The obtained seeds may be further screened to identify seeds that contain DNA having an event 127 nucleic acid molecule. Such methods may further involve obtaining a DNA sample from the seed of the cross and assaying the sample for the presence or absence of an event 127 nucleic acid molecule. Alternatively, the seeds may be screened for AHAS-inhibiting herbicide tolerance to identify seeds or progeny that contain event 127 DNA.

An event 127 soybean plant can be bred using any breeding method available for soybean. For example, an event 127 soybean plant can be bred by first sexually crossing a first parental soybean plant grown from the transgenic event 127 soybean plant (or progeny thereof derived from transformation with the expression cassettes of the embodiments that confer herbicide tolerance) and a second parental soybean plant that lacks the herbicide tolerance phenotype, thereby producing a plurality of first progeny plants; and then selecting a first progeny plant that displays the desired herbicide tolerance; and selfing the first progeny plant, thereby producing a plurality of second progeny plants; and then selecting from the second progeny plants which display the desired herbicide tolerance. These steps can further include the back-crossing of the first herbicide tolerant progeny plant or the second herbicide tolerant progeny plant to the second parental soybean plant or a third parental soybean plant, thereby producing a soybean plant that displays the desired herbicide tolerance. It is further recognized that assaying progeny for phenotype is not required. Various methods and compositions, as disclosed elsewhere herein, can be used to detect and/or identify the event 127 insert.

It is also to be understood that two different transgenic plants can also be sexually crossed to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. However, any method may be employed to generate such plants.

Inbred soybean lines containing the event 127 nucleic acid molecule may be developed for use in the production of soybean varieties and for use as parental plants in breeding programs to create new and distinct inbred soybean lines. Inbred soybean lines are often used as targets for the introgression of novel traits through traditional breeding and/or molecular introgression techniques. Many analytical methods are available to determine the homozygosity and phenotypic stability of inbred lines.

In some embodiments, the nucleic acid molecule resulting in the production of the event 127 soybean plant of the invention can be engineered into a molecular stack with a nucleic acid molecule that confers resistance to a second herbicide, such as glyphosate. In other embodiments, the molecular stack further comprises at least one additional nucleic acid molecule that confers tolerance to a third herbicide. In one embodiment, the sequence confers tolerance to glufosinate, and in a specific embodiment, the sequence comprises pat.

In other embodiments, the event 127 soybean plant of the invention comprises one or more traits of interest, and in some embodiments, the event 127 DNA is stacked with any combination of nucleic acid molecule sequences and/or traits of interest in order to create plants with a desired combination of traits. A trait, as used herein, refers to the phenotype derived from a particular sequence or groups of sequences. For example, herbicide-tolerance nucleic acid molecules may be stacked with any other nucleic acid molecules encoding polypeptides having pesticidal and/or insecticidal activity, such as *Bacillus thuringiensis* toxic proteins (Bt proteins), lectins, and the like. The combinations generated can also include multiple copies of any one of the nucleic acid molecules of interest.

In some embodiments, soybean event 127 DNA can be stacked with other herbicide-tolerance traits to create a transgenic plant of the invention with further improved properties. Other herbicide-tolerance nucleic acid molecules that could be used in such embodiments include those conferring tolerance to glyphosate or to AHAS inhibitors by other modes of action, such as, for example, a gene that encodes a glyphosate oxido-reductase enzyme. Other traits that could be combined with the soybean event 127 DNA include those derived from nucleic acid molecules that confer on the plant the capacity to produce a higher level of 5-enolpyruvylshikimate-3-phosphate synthase (EPSPS). Other traits that could be combined with the soybean 127 event include those conferring tolerance to sulfonylurea and/or imidazolinone.

In some embodiments, the soybean event 127 DNA may be stacked with, for example, hydroxyphenylpyruvatedioxygenases which are enzymes that catalyze the reaction in which para-hydroxyphenylpyruvate (HPP) is transformed into homogentisate. Molecules which inhibit this enzyme and which bind to the enzyme in order to inhibit transformation of the HPP into homogentisate are useful as herbicides. Traits conferring tolerance to such herbicides in plants are known in the art. Other examples of suitable herbicide-tolerance traits that could be stacked with the soybean event 127 DNA include aryloxyalkanoate dioxygenase nucleic acid molecules (which reportedly confer tolerance to 2,4-D and other phenoxy auxin herbicides as well as to aryloxyphenoxypropionate herbicides) and dicamba-tolerance nucleic acid molecules.

Other examples of herbicide-tolerance traits that could be combined with the soybean event 127 DNA include those conferred by nucleic acid molecules encoding an exogenous phosphinothricin acetyltransferase. Plants containing an exogenous phosphinothricin acetyltransferase can exhibit improved tolerance to glufosinate herbicides, which inhibit the enzyme glutamine synthase. Other examples of herbicide-tolerance traits that could be combined with the soybean event 127 DNA include those conferred by nucleic acid molecules conferring altered protoporphyrinogen oxidase (protox) activity. Plants containing such nucleic acid molecules can exhibit improved tolerance to any of a variety of herbicides which target the protox enzyme (also referred to as "protox inhibitors").

Other examples of herbicide-tolerance traits that could be combined with the AHAS-inhibitor tolerance trait include those conferring tolerance to at least one herbicide in a plant such as, for example, a soybean plant. Herbicide-tolerant soybeans are known in the art, as are plants that vary in their tolerance to particular herbicides. The trait(s) responsible for these tolerances can be combined by breeding or via other methods with the event 127 soybean plant to provide a plant of the invention as well as methods of use thereof.

The soybean event 127 DNA can also be combined with at least one other trait to produce plants of the present invention that further comprise a variety of desired trait combinations including, but not limited to, traits desirable for animal feed such as high oil content; amino acid composition, protein content, improved digestibility, or altered fatty acid compositions.

The soybean event 127 DNA can also be combined with other desirable traits such as, for example, avirulence and disease resistance genes, such as soybean cyst nematode resistance traits, for example SCN, and traits desirable for processing or process products such as increased oil content or modified fatty acid composition (e.g., fatty acid desaturase genes; and polymers or bioplastics (e.g., beta-ketothiolase, polyhydroxybutyrate synthase, and acetoacetyl-CoA reductase) facilitate expression of polyhydroxyalkanoates (PHAs)). One could also combine herbicide-tolerant nucleic acid molecules with nucleic acid molecules providing any agronomic traits.

These stacked combinations can be created by any method including, but not limited to, breeding plants by any known methodology, or genetic transformation. If the sequences are stacked by genetically transforming the plants, the nucleic acid molecule sequences of interest can be combined at any time and in any order. The traits can be introduced simultaneously in a co-transformation protocol with the nucleic acid molecules of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the nucleic acid molecule of interest. This may be combined with any combination of other suppression cassettes or overexpression cassettes to generate the desired combination of traits in the plant. It is further recognized that nucleic acid molecules can be stacked at a desired genomic location using a site-specific recombination system.

Also provided are methods of breeding soybean plants having the event 127 DNA, where the method comprises (a) crossing an event 127 soybean plant or derivative thereof, with a second soybean parent plant; (b) obtaining seed from the cross; (c) obtaining a DNA sample from one or more seeds; and (d) detecting the presence of an event 127 nucleic acid molecule.

V. TRANSFORMED PLANTS

Soybean plants having traits combined with the event 127 trait can also be produced by transformation of plant material or parts obtained from event 127 soybean plants. Additional traits can be combined into event 127 soybean plants using any transformation method available to the artisan. Thus, the event 127 soybean plants can be used as the source of plant material for use in transformation methods to introduce additional heterologous nucleic acid molecules into an event 127 soybean plant. For example, transformation vectors can be prepared to introduce genes of interests into event 127 soybean plants to produce soybean plants having multiple introduced traits.

The transformation vectors for use in such methods can be used to produce plants transformed with any gene of interest, including those described herein. The transformation vector may include a selectable marker and a gene of interest to be introduced and typically expressed in the transformed event 127 soybean plant. Such selectable markers are known in the art. The genes of interest of the invention vary depending on the desired trait to be introduced. For example, various changes in phenotype can be of interest including modifying the fatty acid composition in a plant, altering the amino acid content of a plant, altering a plant's insect and/or pathogen defense mechanisms, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Any transformation vector can be used in the methods of the present invention. Numerous plant transformation vectors and methods for transforming plants are available. The transformation methods can be used to stack any trait with the AHAS-inhibiting herbicide tolerance trait provided by the event 127 insert, including those described herein.

VI. METHODS OF DETECTION

Methods and compositions for identifying and/or detecting event 127 nucleic acid molecules in a biological sample, for example from a sample obtained from a soybean plant, including progeny and derivatives, are also provided. Such methods find use in identifying and/or detecting event 127 regions or nucleic acid molecules in any biological material. Such methods include, for example, methods to confirm seed purity and methods for screening seeds in a seed lot for an event 127 nucleic acid molecule. In one embodiment, a method for identifying 127 insert nucleic acid molecule in a biological sample is provided and comprises forming a mixture of a biological sample and a first and a second nucleic acid primer capable of amplifying an event 127 nucleic acid molecule; reacting the mixture under conditions that allow the first and second nucleic acid primers to amplify a soybean event 127 nucleic acid molecule; and, detecting the presence or absence of an amplified event 127 nucleic acid molecule. In some embodiments, the event 127 nucleic acid molecule is an event 127 specific nucleic acid molecule.

Also provided are methods for identifying an event 127 nucleic acid molecule in a biological sample comprising forming a mixture containing a biological sample having soybean DNA and a nucleic acid molecule probe that is capable of hybridizing to a soybean event 127 nucleic acid molecule, reacting the mixture under conditions that allow the nucleic acid molecule probe to hybridize to an event 127 nucleic acid molecule, and detecting whether the nucleic acid molecule probe hybridizes to an event 127 nucleic acid molecule in the sample, where the presence of hybridization indicates the presence of an event 127 nucleic acid molecule.

The methods of the present invention can also be used to identify and/or detect an event 127 insert nucleic acid molecule in a biological sample. In one embodiment, a method for identifying an event 127 nucleic acid molecule in a biological sample is provided and comprises forming a mixture of a biological sample and a first and a second nucleic acid primer capable of amplifying an event 127 insert nucleic acid molecule; reacting the mixture under conditions that allow the first and second nucleic acid primers to amplify an event 127 insert nucleic acid molecule; and, detecting the presence or absence of an amplified event 127 insert nucleic acid molecule.

Also provided are methods for identifying event 127 nucleic acid molecules in a biological sample comprising forming a mixture containing a biological sample having DNA and a nucleic acid molecule probe that is capable of hybridizing to an event 127 nucleic acid molecule, reacting the mixture under conditions that allow the nucleic acid molecule probe to hybridize to an event 127 nucleic acid molecule, and detecting whether the nucleic acid molecule probe hybridizes to an event 127 nucleic acid molecule in the sample, where the presence of hybridization indicates the presence of an event 127 nucleic acid molecule.

Further provided are methods for the detection of event 127 regions in a biological sample. The event 127 regions that can be detected using the methods of the present invention include event 127 insert DNA, 5' junction regions, 3' junction regions, 5' flanking regions, 3' flanking regions, unique mutations or duplications in the insert DNA resulting from the transformation event, or combinations and fragments of any thereof.

A biological sample can comprise any sample in which one desires to determine if DNA having an event 127 nucleic acid molecule is present. For example, a biological sample can comprise any plant material or material comprising or derived from a plant material such as, but not limited to, food or feed products. As used herein, "plant material" refers to material which is obtained or derived from a plant or plant part. In specific embodiments, the biological sample comprises a soybean tissue. In other embodiments, the biological sample is obtained from soybean leaf tissue. In still other embodiments, the biological sample is obtained from soybean seed tissue.

Any event 127-related nucleic acid molecule can be detected and/or identified using the methods of the present invention. For example, nucleic acid molecules that can be detected include, but are not limited to DNA, mRNA, cDNA, and the like. In other embodiments, polypeptides encoded by the event 127 nucleic acid molecules can be detected and/or identified using the methods of the present invention. The detected and/or identified nucleic acid molecules can encompass any fragment of the event 127 insert DNA, including identified mutations in the insert DNA, for example nucleic acid molecules encoding AHAS polypeptides having S653N or R272K, and the like, promoter sequences, termination sequences, fragments of such sequences, and combinations thereof.

Primers and probes for use in the methods disclosed herein can be used to confirm (and, if necessary, to correct) the disclosed sequences by conventional methods, e.g., by re-cloning and sequencing such sequences. The nucleic acid molecule probes and primers specifically detect a target DNA sequence. Any conventional nucleic acid hybridization or amplification method can be used to detect or identify the presence of a nucleic acid molecule from a transgenic event in a sample. By "specifically detect" it is intended that the nucleic acid molecule can be used either as a primer to amplify a 127 specific region or the nucleic acid molecule can be used as a probe that hybridizes under stringent conditions to a nucleic acid molecule having an event 127 specific region. The level or degree of hybridization which allows for the specific detection of a 127 event or a specific region of a 127 event is sufficient to distinguish the nucleic acid molecule with the 127 specific region from a nucleic acid molecule lacking this region and thereby allow for discriminately identifying an event 127 molecule. By "shares sufficient sequence identity or complementarity to allow for the amplification of an event 127 nucleic acid molecule" is intended the sequence shares at least 80%, 85%, 90%, 91%, 92%, 93%, 94%, 95%, 96%, 97%, 98%, 99% or 100% identity or complementarity to a fragment or across the full length of the nucleic acid molecule having the event 127 nucleic acid molecule.

Regarding the amplification of a target nucleic acid molecule (e.g., by PCR) using a particular amplification primer pair, "stringent conditions" are conditions that permit the primer pair to hybridize to the target nucleic acid molecule to which a primer having the corresponding wild-type sequence (or its complement) would bind and preferably to produce an identifiable amplification product (the amplicon) having an event 127 nucleic acid molecule in a DNA thermal amplification reaction. In a PCR approach, oligonucleotide primers can be designed for use in PCR reactions to amplify an event 127 nucleic acid molecule. Methods for designing PCR primers and PCR cloning are generally known in the art. It is understood that a number of parameters in a specific PCR protocol may need to be adjusted to specific laboratory conditions and may be slightly modified and yet allow for the collection of similar results. These adjustments will be apparent to a person skilled in the art.

Primers for use in the disclosed methods can be used to amplify any 127 nucleic acid molecule. For example, primer pairs can be designed that are capable of amplifying regions that are indicative of a plant containing an event 127 nucleic acid molecule fragment. In one embodiment, such primer pairs can amplify a region comprising a single junction, for example 5' junction region or a 3' junction region. Such primer pairs include one primer that is capable of priming elongation from a flanking chromosomal region (e.g. 5' or 3' flanking regions) in the direction of the insert DNA, while the second primer is capable of priming from the insert DNA in the direction of the first primer in the flanking chromosomal region. Such primer pairs amplify a nucleic acid molecule that encompasses a junction region. In some embodiments, one of the primers used in the amplification pair is capable of annealing to a region that spans one of the junction regions (e.g., 5' or 3' junction regions) and is capable of amplification in the direction of the chromosomal region or in the direction of the insert. The flanking chromosomal region primers for use in such methods may be capable of annealing to either 5' or 3' flanking chromosomal regions and prime amplification in the direction of the insert. In other embodiments, primer pairs can be designed that are capable of amplifying two junctions.

Other examples of suitable primers capable of annealing to the 5' or 3' flanking regions may be designed for use in such methods and can comprise primer sequences of from about 10 or 12 to about 40 nucleotides capable of annealing to a nucleic acid molecule between positions 1-1311 of SEQ ID NO:1 or positions 6070 to 10,656 of SEQ ID NO:1.

Alternatively, random primers may be developed that are capable of annealing throughout the plant genome and can be used in conjunction with an insert specific primer to amplify a nucleic acid molecule that encompasses the insert DNA and a fragment of flanking sequence. In some embodiments, the insert specific primer can be labeled to allow for detection of a fragment amplified using the insert specific primer. In other embodiments, the resulting amplified nucleic acid molecules can be hybridized with labeled probes to identify or detect event 127 nucleic acid molecules.

In another embodiment, primer pairs can be developed that amplify the entire insert DNA or a portion of the insert that is indicative of event 127 DNA. For example, in some embodiments, the primer pairs can be designed to amplify the entire insert DNA using primers that prime from the 5' and 3' flanking regions of the insert. Alternatively, primer pairs can be designed that are capable of amplifying a region of the event 127 insert alone to identify the presence of the insert. For example, primers can be designed to amplify any region within the PvuII fragment of the plasmid pAC321 for use in detecting the presence of the insert in a biological sample. Such primers include those capable of amplifying any of the regions of the insert DNA, including the region between positions 1312 and 6069 of SEQ ID NO:1. In some embodiments primer pairs can be developed that are capable of amplifying the *Arabidopsis thaliana* mutant AHAS coding sequence of the insert DNA (e.g. positions 2762 through 4774 or fragments thereof), or any combination of the coding sequence and regulatory sequences of the insert.

The amplified nucleic acid molecule (amplicon) can be of any length that allows for the detection of the event 127 nucleic acid molecule. For example, the amplicon can be about 10, 50, 100, 200, 300, 500, 700, 100, 2000, 3000, 4000, 5000 nucleotides in length or longer.

In some embodiments, one or more specific regions of the event 127 nucleic acid molecule can be detected.

Any primer that allows an event 127 nucleic acid molecule to be amplified and/or detected can be employed in the methods of the present invention. In one embodiment, the primers comprise or are complementary to an event 127 nucleic acid molecule, such as for example 8, 10, 11, 12, 13, 14, 15, 16, 17, 18, 19, 20, 21, 22, 23, 24, 25, 26, 27, 28, 29, 30, or more contiguous nucleotides corresponding to, or complementary of, a nucleic acid molecule having a sequence of SEQ ID NO:1. For example, in some embodiments, the first and second primers comprise a nucleic acid molecule of SEQ ID NO:35, 36, 37, 38, 39, 40, 41, 42, 43, 44, 67, 68, 69, and 70, where the first or the second primer shares sufficient sequence identity or complementarity to the nucleic acid molecule to amplify the event 127 nucleic acid molecule. In still further embodiments, the first and the second primer can comprise any one or any combination of the sequences set forth in SEQ ID NO:35, 36, 37, 38, 39, 40, 41, 42, 43, 44, 67, 68, 69, and 70. The primers can be of any length sufficient to amplify a soybean event 127 region including, for example, at least 6, 7, 8, 9, 10, 15, 20, 15, or 30 or about 7-10, 10-15, 15-20, 20-25, 25-30, 30-35, 35-40, 40-45 nucleotides or longer.

As described above, in certain embodiments, useful primer pairs will include one primer that overlaps with the junction point between the insert DNA and the flanking 5' or 3' genomic DNA. Such primers may be designed around the junction point between the 5' flanking DNA and the insert DNA (i.e., the junction between positions 1311 and 1312 of SEQ ID NO:1) as well as around the junction point between the insert DNA and the 3' flanking DNA (i.e., the junction between positions 6069 and 6070 of SEQ ID NO:1). Such primers may be designed to hybridize with about 10 nucleotides from either the flanking region or the insert DNA and with at least 1 nucleotide across the junction point in the insert DNA or the flanking region. Thus, for example, primers may comprise nucleotide sequences designed to hybridize with the nucleotides represented by at least the following positions of SEQ ID NO:1: 1311-1321, 1302-1312, 6060-6070, and/or 6069-6079.

In other embodiments, useful primer pairs will include one primer that overlaps with the junction point between the 5' end of the duplicated portion of the csr1-2 coding sequence of the insert DNA (at position 5694 of SEQ ID NO:1) and the 3' end of the adjacent insert DNA portion (i.e., at position 5693 of SEQ ID NO:1). Such primers may be designed to hybridize with about 10 nucleotides from either the duplicated region or the adjacent insert DNA and with at least 1 nucleotide across the junction point (e.g., at least 5693-5703 or at least 5684-5694 of SEQ ID NO:1).

As discussed elsewhere herein, any method to PCR amplify the event 127 nucleic acid molecule can be employed, including for example, real time PCR.

Thus, in some embodiments, a method of detecting the presence of event 127 nucleic acid molecules in a biological sample is provided. The method comprises (a) extracting a DNA sample from the biological sample; (b) providing a pair of DNA primer molecules (e.g., any combination of SEQ ID NOs:35, 36, 37, 38, 39, 40, 41, 42, 43, 44, 67, 68, 69, and 70, where the combination amplifies a soybean event 127 region), including, but not limited to, i) the sequences of SEQ ID NO:35 and SEQ ID NO:36, ii) SEQ ID NO:37 and SEQ ID NO:38, iii) SEQ ID NO:39 and SEQ ID NO:40, iv) SEQ ID NO:41 and SEQ ID NO:42, v) SEQ ID NO:43 and SEQ ID NO:44, yl) SEQ ID NO:67 and SEQ ID NO:68, and vii) SEQ ID NO:69 and SEQ ID NO:70; (c) providing DNA amplification reaction conditions; (d) performing the DNA amplification reaction, thereby producing a DNA amplicon molecule; and (e) detecting the DNA amplicon molecule, where the detection of the DNA amplicon molecule in the DNA amplification reaction indicates the presence of event 127 nucleic acid molecules in the sample. In order for a nucleic acid molecule to serve as a primer or probe it needs only be sufficiently complementary in sequence to be able to form a stable double-stranded structure under the particular solvent and salt concentrations employed.

In hybridization techniques, all or part of a nucleic acid molecule that selectively hybridizes to a target event 127 nucleic acid molecule may be employed. By "stringent conditions" or "stringent hybridization conditions" when referring to a nucleic acid molecule probe conditions under which a probe will hybridize to its target sequence to a detectably greater degree than to other sequences (e.g., at least 2-fold over background) are intended. Regarding the amplification of a target nucleic acid molecule (e.g., by PCR) using a particular amplification primer pair, "stringent conditions" are conditions that permit the primer pair to hybridize to the target nucleic acid molecule to which a primer having the corresponding wild-type. Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of identity are detected (heterologous probing). Generally, a probe is less than about 1000 nucleotides in length or less than 500 nucleotides in length.

As used herein, a substantially identical or complementary sequence is a nucleic acid molecule that will specifically hybridize to the complement of the nucleic acid molecule to which it is being compared under high stringency conditions. Appropriate stringency conditions which promote DNA hybridization, for example, 6× sodium chloride/sodium citrate (SSC) at about 45° C., followed by a wash of 2×SSC at 50° C., are known to those skilled in the art. Typically, stringent conditions for hybridization and detection will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Examples of low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Examples of moderate stringency conditions include hybridization in 40 to 45% formamide, 1.0 M NaCl, 1% SDS at 37° C., and a wash in 0.5× to 1×SSC at 55 to 60° C. Examples of high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In hybridization reactions, specificity is typically the function of post-hybridization washes, the critical factors being the ionic strength and temperature of the final wash solution. For DNA-DNA hybrids, the $T_m$ can be approximated from the equation of Meinkoth and Wahl (1984) Anal. Biochem. 138: 267-284: $T_m$81.5° C.+16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. The hybridization of the probe to the target DNA molecule can be detected by any number of methods known to those skilled in the art, these can include, but are not limited to, fluorescent tags, radioactive tags, antibody based tags, and chemiluminescent tags.

A nucleic acid molecule is said to be the "complement" of another nucleic acid molecule if they exhibit complementarity. As used herein, molecules are said to exhibit "complete complementarity" when every nucleotide of one of the nucleic acid molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions.

In other embodiments, event 127 plants can be detected or identified by detection of an expressed *Arabidopsis thanliana* AHAS polypeptide. Any method can be used in the detection of the AHAS polypeptide. For example, antibodies raised against the introduced AHAS protein may be used to detect the presence of an express AHAS polypeptide.

Any method can be used to detect an event 127 nucleic acid molecule or amplicon thereof, including, but not limited to, Genetic Bit Analysis. In one method, a DNA oligonucleotide is designed which overlaps both the adjacent flanking DNA sequence and the inserted DNA sequence. In other embodiments, DNA primer oligos are designed to allow for an event 127 specific amplicon. The oligonucleotide is immobilized in wells of a microwell plate. Following PCR of the region of interest a single-stranded PCR product can be hybridized to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization, and single base extension.

Another detection method for use in the methods of the present invention is the Pyrosequencing technique. In this method, an oligonucleotide is designed that overlaps the adjacent DNA and insert DNA junction or a pair of oligos are employed that can amplify an event 127 specific region. The oligonucleotide is hybridized to a single-stranded PCR product from the region of interest (one primer in the inserted sequence and one in the flanking sequence) and incubated in the presence of a DNA polymerase, ATP, sulfurylase, luciferase, apyrase, adenosine 5' phosphosulfate and luciferin. dNTPs are added individually and the incorporation results in a light signal which is measured. A light signal indicates the presence of the transgene insert/flanking sequence due to successful amplification, hybridization, and single or multi-base extension.

Fluorescence Polarization may also be used to detect an amplicon of the invention. Using this method, an oligonucleotide is designed which overlaps the flanking and inserted DNA junction or a pair of oligos are employed that can amplify an event 127 specific region. The oligonucleotide is hybridized to a single-stranded PCR product from the region of interest (one primer in the inserted DNA and one in the flanking DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

Taqman® gene expression assay (PE Applied Biosystems, Foster City, Calif.) may also be used for detecting and quantifying the presence of an event 127 nucleic acid molecule. Briefly, a FRET oligonucleotide probe is designed which overlaps the flanking and insert DNA junction or a pair of oligos are employed that can amplify an event 127 nucleic acid molecule. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons can also be employed in the disclosed methods. Briefly, a FRET oligonucleotide probe is designed that overlaps the flanking and insert DNA junction or a pair of oligos is employed that can amplify a 127 specific region. The unique structure of the FRET probe results in it containing secondary structure that keeps the fluorescent and quenching moieties in close proximity. The FRET probe and PCR primers (one primer in the insert DNA sequence and one in the flanking sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

A hybridization reaction using a probe specific to a sequence found within the amplicon is yet another method used to detect the amplicon produced by a PCR reaction of the present invention.

In another embodiment, event 127 nucleic acid molecules can be detected or identified by methods of detecting polypeptides produced by the event 127 nucleic acid molecules. For example, the expression product of the csr-1AHAS gene can be detected using the methods disclosed herein. Such methods may involve the use of binding proteins that are capable of binding to polypeptides produced by the inserted event 127 nucleic acid molecule. Such methods include, but are not limited to, immunological assays such as, ELISA (enzyme linked immunoabsorbent assays), antigen assays, immunostaining, immuno-hisotchemistry, protein chip assays, radioimmunoprecipitation assays, rapid membrane immunochromatographic assays, and rapid stick immunochromatographic assays (lateral flow tests).

The methods disclosed herein can be adapted for use in high-throughput techniques, for example, by attaching the diagnostic molecules (such as primers and/or probes) on a substrate, to form a device, for example an array or a microarray, or to multi-well plates. The devices may be provided in any useful format, such as chips, slides, plates, membranes, fibers, beads, strips, sticks, mats, lattices, rods, fabrics, vessel walls, and the like. In addition, the substrates can be made of any material available, such as, glass, ceramics, gels (e.g. hydrogels, microgels, pseudogels), and polymeric materials (e.g. plastics, silicone, fluoropolymers). Thus, the substrates for use in the devices and methods of the present invention include, but are not limited to, silica chips, nylon membranes, optical fibers, multi-well plates, and the like. The probes or other event 127 diagnostic molecules can be attached to the substrate using any attachment methods available, such as, covalent binding, coordinate binding, and non-covalent binding (e.g. ionic binding, hydrogen binding, lipophilic attraction).

An array-based method for high-throughput detection, identification or monitoring of expression may be utilized to measure event 127 nucleic acid molecule hybridization targets. This 'chip'-based approach involves using microarrays of nucleic acid molecules as gene-specific hybridization targets to quantitatively measure expression of the corresponding genes. Every nucleotide in a large sequence can be queried at the same time. Hybridization can be used to efficiently analyze nucleotide sequences.

Any microarray method available can be used in the methods of the present invention. For example, a microarray method may compare the sequences to be analyzed by hybridization to a set of oligonucleotides or cDNA molecules representing all possible subsequences. A second method hybridizes the sample to an array of oligonucleotide or cDNA probes. An array consisting of oligonucleotides or cDNA molecules complementary to subsequences of an event 127 target sequence can be used to determine the identity of a target sequence, measure its amount, and detect differences between the target and a reference sequence. Nucleic acid molecules microarrays may also be screened with protein molecules or fragments thereof to determine nucleic acid molecules that specifically bind protein molecules or fragments thereof. Other microarray diagnostic methods for use in the methods of the present invention include, for example, those disclosed in U.S Publication No. 2007/0298423.

Thus, event 127 nucleic acid molecules can be identified or detected in a sample using any method available. Such methods include, but are not limited to, gel separation techniques, nucleic acid blot detection (e.g. Southern hybridization, Northern hybridization), qualitative, semi-quantitative, or quantitative PCR, immunoassays (e.g. ELISA, strip assays (e.g. lateral flow strips) using any immunoglobulins, monoclonal antibodies, single-chain antibodies, or binding-region-retaining antibody fragments) for detection of expression of a modified AHASL, and microarray or "microchip" based detection assays. In other embodiments, the methods can involve the use of mass spectrometry or nuclear magnetic resonance (NMR) techniques to detect or identify the presence of event 127 nucleic acid molecules in a biological sample.

Devices useful in such detection methods are also provided in various embodiments hereof, the devices comprising a solid support having a surface; and attached thereto at least one event 127 diagnostic molecule. These can be hybridization assay devices, immunoassay devices, receptor-ligand binding assay devices, or any others known in the art.

VII. KITS

The present invention also provides kits for detecting an event 127 plant, or event 127 nucleic acid molecule, where the kit comprises a first and a second nucleic acid primer that are capable of amplifying an event 127 nucleic acid molecule. The resulting amplified event 127 nucleic acid molecules may be detected directly, or used as hybridization probes in reactions with biological samples containing DNA.

As used herein, "kit" refers to a set of reagents for the purpose of performing the method embodiments, more particularly, the identification and/or the detection of the 127 event in biological samples. The kit can be used, and its components can be specifically adjusted, for purposes of quality control (e.g. purity of seed lots), detection of event 127 nucleic acid molecules in plant material, or material comprising or derived from plant material, such as but not limited to food or feed products.

In specific embodiments, a kit for identifying event 127 nucleic acid molecules in a biological sample is provided. The kit comprises a first and a second primer, wherein the first and second primer are capable of amplifying an event 127 nucleic acid molecule. In further embodiments, the kit also comprises a nucleic acid molecule for the detection of an event 127 nucleic acid molecule. The kit can comprise, for example, a first primer and a second primer comprising a nucleic acid molecule having the sequence of SEQ ID NOs: 35, 36, 37, 38, 39, 40, 41, 42, 43, and 44, where the first or the second primer shares sufficient sequence homology or complementarity to the nucleic acid molecule to amplify an event 127 nucleic acid molecule. For example, in specific embodiments, the first primer or second primer comprises a fragment of a nucleic acid molecule having the sequence of SEQ ID NO:35, 36, 37, 38, 39, 40, 41, 42, 43, 44, 67, 68, 69 and 70, where the first or the second primer shares sufficient sequence homology or complementarity to the nucleic acid molecule to amplify an event 127 molecule. The primer pair can comprise a fragment of a nucleic acid molecule having the sequence of SEQ ID NO:5 and a fragment of a nucleic acid molecule having the sequence of SEQ ID NO:6, or alternatively, the primer pair can be selected from the sequences of i) SEQ ID NO:35 and SEQ ID NO:36, ii) SEQ ID NO:37 and SEQ ID NO:38, iii) SEQ ID NO:39 and SEQ ID NO:40, iv) SEQ ID NO:41 and SEQ ID NO:42, v) SEQ ID NO:43 and SEQ ID NO:44, vi) SEQ ID NO:67 and SEQ ID NO:68, and vii) SEQ ID NO:69 and SEQ ID NO:70. In still further embodiments, the first and the second primer can comprise any one or any combination of the sequences set forth in SEQ ID NO:35, 36, 37, 38, 39, 40, 41, 42, 43, 44, 67, 68, 69, and 70. The primers can be of any length sufficient to amplify an event 127 molecule including, for example, at least 6, 7, 8, 9, 10, 15, 20, 15, or 30 or about 7-10, 10-15, 15-20, 20-25, 25-30, 30-35, 35-40, 40-45 nucleotides or longer.

Further provided are DNA detection kits comprising at least one nucleic acid molecule that can specifically detect an event 127 region, where the nucleic acid molecule comprises at least one DNA molecule of a sufficient length of contiguous nucleotides homologous or complementary to SEQ ID NO:5 and/or 6. In some embodiments, the DNA detection kit comprises a nucleic acid molecule having SEQ ID NO:5 and/or 6 or comprises a sequence which hybridizes with sequences that specifically detect an event 127 region, such as those selected from the group consisting of SEQ ID NOs:5 and/or 6.

VIII. METHODS OF CONTROLLING WEEDS

The present invention also provides methods and compositions for controlling weeds or undesired plants. The methods generally involve applying an effective amount of one or more non-selective herbicides to a cultivated area or crop field containing one or more event 127 soybean plants. Although any weeds may be controlled by the disclosed methods, in some embodiments, the methods may involve first identifying weeds or undesired plants in an area or field as susceptible to an AHAS-inhibiting herbicide.

Methods are provided for controlling weeds in an area of cultivation, preventing the development or the appearance of weeds or undesired plants in an area of cultivation, producing a crop, and increasing crop safety. The term "controlling," and derivations thereof, for example, as in "controlling weeds" refers to one or more of inhibiting the growth, germination, reproduction, and/or proliferation of; and/or killing, removing, destroying, or otherwise diminishing the occurrence and/or activity of a weed and/or undesired plant.

The methods of the invention may control weeds or undesired plants in an area by any measurable amount, such as reducing the amount of weeds or undesired plants in an area by at least about 5%, 10%, 20%, 30%, 40%, 50%, 60%, 70%, 80%, 90%, 95% compared to an area that has not been treated with the same amount and type of herbicide. The control of weeds or undesired plants can be measured by any reproducible means of measurement. In one embodiment, the control of weeds or undesired plants is measured by counting the number of weeds or undesired plants growing in an area treated with an herbicide and comparing to the number of weeds or undesired plants growing in an untreated area of similar size.

The present invention also provides methods for controlling weeds or undesired plants by contacting seeds of event 127 soybean plants before sowing and/or after pregermination with an AHAS-inhibiting herbicide. The method can further comprise sowing the seeds, for example, in a suitable growth medium, such as field soil or in a potting medium in greenhouse. The methods find particular use in controlling weeds and/or undesired plants in the immediate vicinity of the seed.

Weeds, in the broadest sense, are understood as meaning all those plants which grow in locations where they are undesired.

Weeds which can be controlled by the methods of the present invention include, for example, dicotyledonous and monocotyledonous weeds. Dicotyledonous weeds that can be controlled using the disclosed methods include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus,* and *Taraxacum*. Monocotyledonous weeds that can be controlled using the disclosed methods include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus,* and *Apera*. Particular weeds that can be controlled by the methods of the present invention include, but are not limited to, agriculturally important weeds such as *Ipomoea* spp., *Commelina* spp., *Tridax procumbens, Euphorbia* spp., *Sida* spp, *Bidens* spp., *Galinsoga* spp, *Solanum* spp., *Xanthium* spp, *Chenopodium* spp., *Spermacoce latifolia, Richardia brasiliensis, Sonchus oleraceous, Conyza* spp, *Amaranthus* spp., *Acanthospermum* spp., *Hyptis* spp. *Portulaca oleracea, Casia obtusifolia* and also includes control of cyperaceas species of *Cyperus* spp., as well as grass species including *Brachiaria* spp., *Digitaria* spp., *Panicum* spp., *Setaria* spp., *Sorghum halepense, Echnochloa* spp., *Eleusine indica,* and *Pennisetum* spp. With the use of the non-selective imidazolinone herbicides, the disclosed methods are advantageous for the control of difficult to control weeds, such as *Commelina* spp, *Conyza* spp., *Chamaesise hirta, Spermacoce latifolia, Richardia brasiliensis, Ipomoea* spp, *Euphorbia heterophylla, Echnochloa* spp and *Casia obtusifolia*.

In addition, weeds that can be controlled by the methods of the present invention include, for example, undesired crop plants that are growing in an identified location. For example, a volunteer maize plant that is in a field that predominantly comprises event 127 soybean plants can be considered a weed, if the maize plant is undesired in the field of soybean plants.

Undesired plants that can be controlled by the methods of the present invention include those plants that were previously planted in a particular field in a previous season, or have been planted in an adjacent area, and include crop plants including soybean, corn, canola, cotton, sunflowers, and the like. In some aspects, the crop plants can be tolerant of herbicides, such as glyphosate or glufosinate herbicides, or can be tolerant of AHAS-inhibiting herbicides.

As used herein, an "area of cultivation" or "cultivated area" comprises any region in which one desires to grow one or more plants such as an event 127 soybean plant. Such areas of cultivations include, but are not limited to, a field in which an event 127 soybean plant is cultivated (such as a crop field, field trial, etc), a greenhouse, a growth chamber, etc.

The methods comprise planting the area of cultivation with the event 127 soybean seeds or soybean plants, and in some embodiments, applying to the crop, seed, weed, undesired plant, soil, or area of cultivation thereof an effective amount of an herbicide of interest. The herbicide can be applied at any time during the cultivation of the event 127 soybean plants. The herbicide can be applied before or after the crop is planted in the area of cultivation. Such herbicide applications can include an application an AHAS inhibiting herbicide, or combinations thereof.

The term "effective amount" means an amount of the herbicide sufficient to result in any observable measure of weed or undesired plant control in a cultivated area. An effective amount of an AHAS-inhibiting herbicide may be in the range of between about 50 g ai/ha to about 500 g ai/ha, between about 50 g ai/ha and about 400 g ai/ha, or between about 50 g ai/ha to about 300 g ai/ha. The effective amount of an AHAS-inhibiting herbicide can also be about 70 g ai/ha, 140 g ai/ha, or 280 g ai/ha. Effective rates of application in the methods of the present invention for an AHAS-inhibiting herbicide can be influenced by many factors including the environment and should be determined under actual use conditions. The weed or undesired plant control can be obtained with one or more applications of an AHAS-inhibiting herbicide at a rate similar to or greater than the amount used for such control in areas that do not have an event 127 soybean. Such rates of application include those of, or equivalent to, 70 g ai/ha, 140, or 280 g ai/ha. Typical commercial rates of application are about 70 g ai/ha of AHAS-inhibiting herbicide, also referred to as a 1× rate of application.

In some embodiments, an effective amount can be an amount of an AHAS-inhibiting herbicide greater than the amount to which the weed or undesired plant to be controlled is tolerant. For example, in embodiments in which a weed or undesired plant is tolerant to an application of 70 g ai/ha but is susceptible to an application of 140 g ai/ha, then an effective amount is 140 g ai/ha.

Accordingly, the present invention provides methods of controlling weeds or undesired plant growth in a cultivated area comprising applying an effective amount of a non-selective herbicide to the cultivated area having one or more event 127 soybean plants.

Also provided are methods of controlling glyphosate tolerant weeds or plants in a cultivated area comprising applying an effective amount of an AHAS-inhibiting herbicide to a cultivated area having one or more event 127 soybean plants.

Also provided is a method of controlling AHAS-inhibiting herbicide tolerant weeds or plants in a cultivated area comprising applying an effective amount of an AHAS-inhibiting herbicide to a cultivated area having one or more event 127 soybean plants. In such embodiments, the effective amount of the AHAS-inhibiting herbicide is applied in an amount sufficient to control the weeds, while having substantially no effect on the event 127 soybean plants.

In some embodiments, the weeds can be controlled prior to planting seed of event 127 soybean in an area. For example, non-selective herbicides, such as AHAS-inhibiting herbicides, can be applied to an area prior to planting the seed in an effective amount to reduce or eliminate weeds in an area before planting the seed. Such applications may occur any amount of time prior to planting effective for controlling the weeds, for example, 1, 2, 3, 4, 5, 6, 7, 8, 9, 10, 11, 12, 13, 14, or more days prior to planting. In addition, any combination of agricultural compositions can be applied in such methods.

In other embodiments, weeds can be controlled after the planting of the event 127 soybean seed. For example, AHAS-inhibiting herbicides can be applied to a growing soybean plant, plant parts, the growing medium (such as soil) surrounding the growing plant and adjacent thereto, or an area, i.e., the local environment, in which a soybean event 127 plant or plants are growing, in an amount effective to control weeds in the area. The growing soybean event 127 plant can be at any developmental stage. In some such embodiments, the growing soybean is at least at the first true leaf stage at the time the herbicide is applied. In addition, any combination of agricultural compositions can be applied in such methods.

Where combinations of agricultural compositions are used in the methods, such combinations may include combinations of herbicides, fungicides, bacteriacides, insecticides, and the like. For example, an AHAS-inhibiting herbicide can be combined with other herbicides, such as, 5-enolpyruvylshikimate 3-phosphate synthase (EPSPS)-inhibiting herbicides, glutamine synthase (GS)-inhibiting herbicides, protoporphyrinogen [IX] oxidase (PPO)-inhibiting herbicides, auxinic herbicides, or combinations thereof.

IX. METHODS OF INCREASING YIELD

Also provided are methods of increasing the yield of a soybean plant or plants comprising applying an effective amount of an AHAS-inhibiting herbicide to a cultivated area having one or more event 127 soybean plants and harvesting seed from the soybean plants. In some embodiments, the increase in yield of the soybean plant or plants is the result of a decrease in weeds growing in the local area of the soybean plant or plants, which would normally compete with the soybean plant or plants.

By using such methods, soybean yield in an area can be increased compared to a comparable area not having soybean event 127 plants. Yield of soybeans can be increased any amount, including, but not limited to, 5%, 6%, 7%, 8%, 9%, 10%, 11%, 12%, 13%, 14%, 15%, 20%, 25%, or more compared to that obtained from a comparable area in which an effective amount of an AHAS-inhibiting herbicide is applied to an area not having event 127 soybean plants.

X. AGRICULTURAL CHEMICAL COMPOSITIONS

The present invention also provides agricultural compositions for application to the disclosed soybean 127 plants. Such compositions may include herbicides, fungicides, bacteriacides, fertilizers, and the like. In one embodiment, the agricultural compositions are herbicidal compositions comprising one or more herbicides or combinations of one or more herbicides with another agricultural composition, such as a fungicide, bacteriacides, fertilizer, and the like.

Any herbicide can be applied to the soybean event 127 crop, crop part, or the area of cultivation containing an event 127 soybean plant. Classification of herbicides (i.e., the grouping of herbicides into classes and subclasses) is well-known in the art and includes classifications by HRAC (Herbicide Resistance Action Committee) and WSSA (the Weed Science Society of America). The HRAC classification is available, for example, on the worldwide at the website hracglobal.com/Publications/ClassificationofHerbicideModeofAction/tabid/222/Default.aspx. An abbreviated version of the HRAC classification (with notes regarding the corresponding WSSA group).

In some embodiments, the present invention provides methods that involve the use of at least one AHAS inhibiting herbicide selected from the group consisting of imidazolinone herbicides, sulfonylurea herbicides, triazolopyrimidine herbicides, pyrimidinyloxybenzoate herbicides, sulfonylaminocarbonyltriazolinone herbicides, and mixtures thereof. In these methods, the AHAS-inhibiting herbicide can be applied by any method known in the art including, but not limited to, seed treatment, soil treatment, and foliar treatment.

In some embodiments, the AHAS-inhibiting herbicide can be combined with one or more additional agricultural compositions, such as additional herbicides, fungicides, bacteriocides, anti-viral compositions, or combinations thereof. The additional herbicides for use in the combinations include any herbicide, including sulfamide herbicides, organophosphate herbicides, and benzothiadiazinone herbicides. Sulfamide herbicides include, but are not limited to saflufenacil. Organophosphate herbicides include, but are not limited to glyphosate and glufosinate. Benzothiadiazinone herbicides include, but are not limited to bentazon. Fungicides for use in such combinations include, but are not limited to pyraclostrobin.

Treatment with combinations of AHAS-inhibiting herbicide compositions and/or with one or more AHAS-inhibiting herbicide compositions and one or more additional agricultural compositions may occur by application of a mixture of such compositions, co-application of such compositions, sequential application of such compositions, or any combination thereof.

In some embodiments, the AHAS-inhibiting herbicide compositions comprise at least one A) AHAS-inhibiting herbicide and at least one further active compound, selected from B) herbicides of classes b1) to b15):
b1) lipid biosynthesis inhibitors;
b2) acetolactate synthase inhibitors (AHAS inhibitors);
b3) photosynthesis inhibitors;
b4) protoporphyrinogen-IX oxidase inhibitors;
b5) bleacher herbicides;
b6) enolpyruvyl shikimate 3-phosphate synthase inhibitors (EPSP inhibitors);
b7) glutamine synthetase inhibitors;
b8) 7,8-dihydropteroate synthase inhibitors (DHP inhibitors);
b9) mitose inhibitors;
b10) inhibitors of the synthesis of long chain fatty acids (VLCFA inhibitors);
b11) cellulose biosynthesis inhibitors;
b12) decoupler herbicides;
b13) auxin herbicides;
b14) auxin transport inhibitors;
b15) other herbicides selected from the group consisting of benzoylprop, flamprop, flamprop-M, bromobutide, chlorflurenol, cinmethylin, methyldymuron, etobenzanid, fosamine, metam, pyributicarb, oxaziclomefone, dazomet, triaziflam and methyl bromide, and
the agriculturally acceptable salts of the active compounds B and the agriculturally acceptable derivatives of the active compounds B, provided they have a carboxyl group.

In other cases, such a combination of at least one A) AHAS-inhibiting herbicide and at least one herbicide B may be used in combination with a safener C (such safeners may also be used in combination with at least one AHAS-inhibiting herbicide). Safeners C may be selected from: benoxacor, cloquintocet, cyometrinil, dichlormid, dicyclonon, dietholate, fenchlorazole, fenclorim, flurazole, fluxofenim, furilazole, isoxadifen, mefenpyr, mephenate, naphthalic anhydride, 2,2,5-trimethyl-1-3-(dichloroacetyl)-1,3-oxazolidine (R-29148), 4-(dichloroacetyl)-1-oxa-4-azaspiro[4.5]decane (AD-67; MON 4660) and oxabetrinil, the agriculturally acceptable salts of the active compounds C and the agriculturally acceptable derivatives of the active compounds C, provided they have a carboxyl group.

Examples of herbicides B which can be used in combination with the AHAS-inhibiting compounds are:

b1) from the group of the lipid biosynthesis inhibitors: chlorazifop, clodinafop, clofop, cyhalofop, diclofop, fenoxaprop, fenoxaprop-p, fenthiaprop, fluazifop, fluazifop-P, haloxyfop, haloxyfop-P, isoxapyrifop, metamifop, propaquizafop, quizalofop, quizalofop-P, trifop, alloxydim, butroxydim, clethodim, cloproxydim, cycloxydim, profoxydim, sethoxydim, tepraloxydim, tralkoxydim, butylate, cycloate, diallate, dimepiperate, EPTC, esprocarb, ethiolate, isopolinate, methiobencarb, molinate, orbencarb, pebulate, prosulfocarb, sulfallate, thiobencarb, tiocarbazil, triallate, vernolate, benfuresate, ethofumesate and bensulide;

b2) from the group of the AHAS-inhibitors: amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac;

b3) from the group of the photosynthesis inhibitors: atraton, atrazine, ametryne, aziprotryne, cyanazine, cyanatryn, chlorazine, cyprazine, desmetryne, dimethametryne, dipropetryn, eglinazine, ipazine, mesoprazine, methometon, methoprotryne, procyazine, proglinazine, prometon, prometryne, propazine, sebuthylazine, secbumeton, simazine, simeton, simetryne, terbumeton, terbuthylazine, terbutryne, trietazine, ametridione, amibuzin, hexazinone, isomethiozin, metamitron, metribuzin, bromacil, isocil, lenacil, terbacil, brompyrazon, chloridazon, dimidazon, desmedipham, phenisopham, phenmedipham, phenmedipham-ethyl, benzthiazuron, buthiuron, ethidimuron, isouron, methabenzthiazuron, monoisouron, tebuthiuron, thiazafluoron, anisuron, buturon, chlorbromuron, chloreturon, chlorotoluron, chloroxuron, difenoxuron, dimefuron, diuron, fenuron, fluometuron, fluothiuron, isoproturon, linuron, methiuron, metobenzuron, metobromuron, metoxuron, monolinuron, monuron, neburon, parafluoron, phenobenzuron, siduron, tetrafluoron, thidiazuron, cyperquat, diethamquat, difenzoquat, diquat, morfamquat, paraquat, bromobonil, bromoxynil, chloroxynil, iodobonil, ioxynil, amicarbazone, bromofenoxim, flumezin, methazole, bentazone, propanil, pentanochlor, pyridate, and pyridafol;

b4) from the group of the protoporphyrinogen-IX oxidase inhibitors: acifluorfen, bifenox, chlomethoxyfen, chlomitrofen, ethoxyfen, fluorodifen, fluoroglycofen, fluoronitrofen, fomesafen, furyloxyfen, halosafen, lactofen, nitrofen, nitrofluorfen, oxyfluorfen, fluazolate, pyraflufen, cinidon-ethyl, flumiclorac, flumioxazin, flumipropyn, fluthiacet, thidiazimin, oxadiazon, oxadiargyl, azafenidin, carfentrazone, sulfentrazone, pentoxazone, benzfendizone, butafenacil, pyraclonil, profluazol, flufenpyr, flupropacil, nipyraclofen and etnipromid;

b5) from the group of the bleacher herbicides: metflurazon, norflurazon, flufenican, diflufenican, picolinafen, beflubutamid, fluridone, fluorochloridone, flurtamone, mesotrione, sulcotrione, isoxachlortole, isoxaflutole, benzofenap, pyrazolynate, pyrazoxyfen, benzobicyclon, amitrole, clomazone, aclonifen, 4-(3-trifluoromethylphenoxy)-2-(4-trifluoromethylphenyl)pyrimidine, and also 3-heterocyclyl-substituted benzoyl derivatives of formula I:

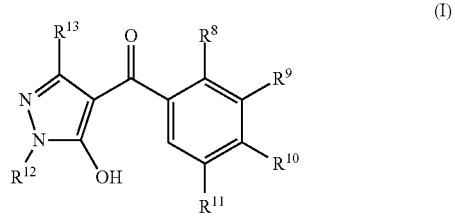

in which the variables $R^8$ to $R^{13}$ are as defined below: $R^8$, $R^{10}$ are hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl or $C_1$-$C_6$-alkylsulfonyl; $R^9$ is a heterocyclic radical selected from the group consisting of: thiazol-2-yl, thiazol-4-yl, thiazol-5-yl, isoxazol-3-yl, isoxazol-4-yl, 10 isoxazol-5-yl, 4,5-dihydroisoxazol-3-yl, 4,5-dihydroisoxazol-4-yl and 4,5-dihydroisoxazol-5-yl, where the nine radicals mentioned may be unsubstituted or mono- or polysubstituted, e.g. mono-, di-, tri- or tetrasubstituted, by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio; Ru is hydrogen, halogen or $C_1$-$C_6$-alkyl; $R^{12}$ is $C_1$-$C_6$-alkyl; $R^{13}$ is hydrogen or $C_1$-$C_6$-alkyl.

b6) from the group of the EPSP synthase inhibitors: glyphosate;

b7) from the group of the glutamine synthase inhibitors: glufosinate and bilanaphos;

b8) from the group of the DHP synthase inhibitors: asulam;

b9) from the group of the mitose inhibitors: benfluralin, butralin, dinitramine, ethalfluralin, fluchloralin, isopropalin, methalpropalin, nitralin, oryzalin, pendimethalin, prodiamine, profluralin, trifluralin, amiprofos-methyl, butamifos, dithiopyr, thiazopyr, propyzamide, tebutam, chlorthal, carbetamide, chlorbufam, chlorpropham and propham;

b10) from the group of the VLCFA inhibitors: acetochlor, alachlor, butachlor, butenachlor, delachlor, diethatyl, dimethachlor, dimethenamid, dimethenamid-P, metazachlor, metolachlor, S-metolachlor, pretilachlor, propachlor, propisochlor, prynachlor, terbuchlor, thenylchlor, xylachlor, allidochlor, CDEA, epronaz, diphenamid, napropamide, naproanilide, pethoxamid, flufenacet, mefenacet, fentrazamide, anilofos, piperophos, cafenstrole, indanofan and tridiphane;

b11) from the group of the cellulose biosynthesis inhibitors: dichlobenil, chlorthiamid, isoxaben and flupoxam;

b12) from the group of the decoupler herbicides: dinofenate, dinoprop, dinosam, dinoseb, dinoterb, DNOC, etinofen and medinoterb;

b13) from the group of the auxin herbicides: clomeprop, 2,4-D, 2,4,5-T, MCPA, MCPA thioethyl, dichlorprop, dichlorprop-P, mecoprop, mecoprop-P, 2,4-DB, MCPB, chloramben, dicamba, 2,3,6-TBA, tricamba, quinclorac, quinmerac, clopyralid, fluoroxypyr, picloram, triclopyr and benazolin;

b14) from the group of the auxin transport inhibitors: naptalam, diflufenzopyr;

b15) benzoylprop, flamprop, flamprop-M, bromobutide, chlorflurenol, cinmethylin, methyldymron, etobenzanid, fosamine, metam, pyributicarb, oxaziclomefone, dazomet, triaziflam and methyl bromide.

The active compounds B of groups b1) to b15) and the active compounds C are known herbicides and safeners, see, for example, The Compendium of Pesticide Common Names (available on the worldwide web at the cite hclrss.demon.co.uk/index.html); Farm Chemicals Handbook 2000 Vol. 86, Meister Publishing Company, 2000; B. Hock, C. Fedtke, R. R. Schmidt, Herbizide, Georg Thieme Verlag, Stuttgart 1995; W. H. Ahrens, Herbicide Handbook, 7th Edition, Weed Science Society of America, 1994; and K. K. Hatzios, Herbicide Handbook, Supplement to 7th Edition, Weed Science Society of America, 1998. 2,2,5-Trimethyl-3-(dichloroacetyl)-1,3-oxazolidine [CAS No. 52836-31-4] is also known under the name R-29148. 4-(Dichloroacetyl)-1-oxa-4-azaspiro[4.5]decane [CAS No. 71526-07-03] is also known under the names AD-67 and MON 4660. The bleacher herbicides of the formula II are disclosed in WO 96/26202, WO 97/41116, WO 97/41117 and WO 97/41118.

As active compounds C, the compositions may comprise at least one of the compounds listed below: benoxacor, cloquintocet, dichlormid, fenchlorazole, fenclorim, fluxofenim, furilazole, isoxadifen, mefenpyr, 2,2,5-trimethyl-3-(dichloracetyl)-1,3-oxazolidine, 4-(dichloroacetyl)-1-oxa-4-azaspiro[4.5]decane and oxabetrinil and/or an agriculturally acceptable salt thereof and/or, in the case of compounds having a COOH group, an agriculturally acceptable derivative.

The compositions that contain combinations of active ingredients can be binary and ternary compositions which comprise at least one AHAS-inhibiting compound as active compound-A and at least one herbicide selected from classes b1) to b15) and, if appropriate, one or more safeners C.

In binary compositions which comprise at least one AHAS-inhibiting compound as component A and at least one herbicide B, the weight ratio of the active compounds A:B is may be in the range from 1:500 to 10:1, in the range from 1:100 to 10:1, in the range from 1:50 to 10:1, or in the range from 1:25 to 5:1.

In binary compositions which comprise at least one AHAS-inhibiting compound and at least one safener C, the weight ratio of the active compounds A:C is usually in the range from 1:100 to 10:1, from 1:50 to 10:1, or in the range from 1:25 to 5:1.

In ternary compositions which comprise both an AHAS-inhibiting compound as component A, at least one herbicide B and at least one safener C, the relative weight ratios of the components A:B:C may be in the range from 10:1:1 to 1:500:10, from 10:1:1 to 1:100:10, from 10:1:1 to 1:50:1, or from 5:1:1 to 1:25:5. In one embodiment, in the ternary compositions, the weight ratio of herbicide B to safener C is in the range from 50:1 to 1:10.

The herbicidally active mixtures described in U.S. Pat. No. 7,375,058 (incorporated by reference herein in its entirety) may also be used in treatments related to soybean event 127 plants.

Protoporphyrinogen [IX] oxidase (PPO) inhibiting herbicides also find use in the compositions of the present invention. PPO inhibiting herbicides are known in the art and include, but are not limited to diphenylether herbicides (including nitrophenyl ether herbicides), such as acifluorfen (5-[2-chloro-4-(trifluoromethyl)phenoxy]-2-nitrobenzoic acid), bifenox (methyl 5-(2,4-dichlorophenoxy)-2-nitrobenzoate), DPEI (5-[2-chloro-4-(trifluoromethyl)phenoxy]-2-nitroacetophenone oxime-o-(acetic acid, methyl ester)), DPEII (5-[2-chloro-4-(trifluoromethyl)phenoxy]-3-methoxyphthalide), ethoxyfen ((1S)-1-carboxyethyl 2-chloro-5-[2-chloro-4-(trifluoromethyl)phenoxy]benzoate), fomesafen (5-[2-chloro-4-(trifluoromethyl)phenoxy]-Nethylsulfonyl)-2-nitrobenzamide), lactofen (ethyl O-[5-(2-chloro-α,α,α-trifluoro-p-tolyloxy)-2-nitrobenzoyl]-DL-lactate), and oxyfluorfen (2-chloro-1-(3-ethoxy-4-nitrophenoxy)-4-(trifluoromethyl)benzene). PPO-inhibiting herbicides also include dicaboximide herbicides such as N-phenyl-phthalimides flumiclorac ([2-chloro-5-(cyclohex-1-ene-1,2-dicarboximido)-4-fluorophenoxy]acetic acid), flumioxazin (N-(7-fluoro-3,4-dihydro-3-oxo-4-prop-2-ynyl-2H-1,4-benzoxazin-6-yl)cyclohex-1-ene-1,2-dicarboxamide). PPO-inhibiting herbicides further include triazolinone herbicides such as carfentrazone (α,2-dichloro-5-[4-(difluoromethyl)-4,5-dihydro-3-methyl-5-oxo-1H-1,2,4-triazol-1-yl]-4-fluorobenzenepropanoic acid), and sulfentrazone (N-[2,4-dichloro-5-[4-(difluoromethyl)-4,5-dihydro-3-methyl-5-oxo-1H-1,2,4-triazol-1-yl]phenyl]methanesulfonamide). PPO-inhibiting herbicides also include phenylpyrazole herbicides, including, but not limited to nipyraclofen (1-[2,6-dichloro-4-(trifluoromethyl)phenyl]-4-nitro-1H-pyrazol-5- amine) and pyraflufen (2-chloro-5-(4-chloro-5-difluoromethoxy-1-methylpyrazol-3-yl)-4-fluorophenoxyacetic acid). PPO-inhibiting herbicides also include oxadiazolone herbicides such as oxadiazon (3-[2,4-dichloro-5-(1-methylethoxy)phenyl]-5-(1,1-dimethylethyl)-1,3,4-oxadiazol-2(3H)-one) and oxadiargyl (5-tert-butyl-3-[2,4-dichloro-5-(prop-2-ynyloxy)phenyl]-1,3,4-oxadiazol-2(3H)-one). PPO-inhibiting herbicides further include thiadiazolone herbicides such as fluthiacet ([[2-chloro-4-fluoro-5-[(tetrahydro-3-oxo-1H,3H-[1,3,4]thiadiazolo[3,4-a]pyridazin-1-ylidene)amino]phenyl]thio]acetic acid); as well as those described in section 111.4) of US2008254985 to Zagar and Sievernich (herein incorporated by reference in its entirety).

Auxinic herbicides also find use in the compositions of the present invention. Auxinic herbicides include those comprising herbicidal active ingredients whose mode of action is as auxin mimics or auxin inhibitors (antiauxins). Examples of auxinic herbicides include, but are not limited to, picloram (4-amino-3,5,6-trichloropicolinic acid); dicamba (3,6-dichloro-2-methoxybenzoic acid); clofibric acid ((p-chlorophenoxy)isobutyric acid); 2-(4-chlorophenoxy)-2-methylpropanoic acid); benazolin (4-chloro-2-oxo-3-benzothiazoleacetic acid; 4-chloro-2-oxobenzothiazolin-3-yl-acetic acid); TIBA (2,3,5-triiodobenozic acid); 2,3,6-TBA (2,3,6-trichlorobenzoic acid); triclopyr (3,5,6-trichloro-2-pyridyloxyacetic acid); quinclorac (3,7-dichloroquinoline-8-carboxylic acid); and the auxin-mimicking or auxin-blocking phenoxy herbicides, for example, phenoxyacetic, phenoxypropionic, and phenoxybutyric herbicides, including: 2,4-D ((2,4-dichlorophenoxy)acetic acid), MCPA ((4-chloro-2-methylphenoxy)acetic acid), 2,4-DB (4-(2,4-dichlorophenoxy) butyric acid), 2,4-DEP (tris[2-(2,4-dichlorophenoxy)ethyl] phosphate), 4-CPA (4-chlorophenoxyacetic acid), 2,4,5-T ((2,4,5-trichlorophenoxy)acetic acid), dichlorprop (2-(2,4-dichlorophenoxy)propanoic acid), fenoprop (2-(2,4,5-trichlorophenoxy)propanoic acid), and mecoprop (2-(2-methyl-4-chloro-phenoxy)propionic acid).

Examples of combinations of agricultural compositions of the present invention include: imazapyr and imazapic; imazapyr and bentazon; imazapyr, imazapic, and bentazon; imazapyr and pyraclostrobin; imazapyr, imazapic, and pyraclostrobin; imazapyr and saflufenacil; imazapyr, imazapic, and saflufenacil; imazapic, saflufenacil, and glyphosate; imazapyr, imazapic, saflufenacil, and glyphosate; imazapic and glyphosate; imazapyr and glyphosate; imazapyr, saflufenacil, and glyphosate; and saflufenacil and glyphosate.

Prior to application, the herbicide, such as the AHAS-inhibiting herbicide, can be converted into the customary formulations, for example solutions, emulsions, suspensions, dusts, powders, pastes and granules. The use form depends on the particular intended purpose; in each case, it should ensure a fine and even distribution of the compound according to the invention.

The formulations for use in the methods of the present invention can be prepared in any known manner, for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Examples of suitable solvents for use in the formulations include water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. Solvent mixtures can also be used.

Examples of suitable carriers for use in the formulations of the present invention include ground natural minerals (for example kaolins, clays, talc, chalk) and ground synthetic minerals (for example highly disperse silica, silicates).

Suitable emulsifiers for use in the formulations of the present invention include nonionic and anionic emulsifiers (for example polyoxyethylene fatty alcohol ethers, alkylsulfonates and arylsulfonates).

Examples of dispersants for use in the formulations of the present invention include lignin-sulfite waste liquors and methylcellulose.

Suitable surfactants for use in the formulations of the present invention include alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides such as can be added to the formulation.

Suitable antifoaming agents for use in the formulations of the present invention include for example antifoaming agents based on silicon or magnesium stearate.

Suitable preservatives for use in the formulations of the present invention include, for example, dichlorophenol and benzylalcoholhemiformaldehyde.

Seed Treatment formulations of the present invention can additionally include binders and optionally colorants.

Binders can be added to the disclosed seed formulations to improve the adhesion of the active materials on the seeds after treatment. Suitable binders are block copolymers EO/PO surfactants but also polyvinylalcoholsl, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

An example of a suitable gelling agent is carrageen (Satiagel®).

Powders, materials for spreading, and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the herbicide, for example, the AHAS-inhibiting herbicide. The herbicides can be employed in a purity of from 90% to 100% by weight, preferably 95% to 100% by weight (according to NMR spectrum). For seed treatment purposes, respective formulations can be diluted 2-10 fold leading to concentrations in the ready to use preparations of 0.01 to 60% by weight active compound by weight, preferably 0.1 to 40% by weight.

An AHAS-inhibiting herbicide of the present invention can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the AHAS-inhibiting herbicide according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

The AHAS-inhibiting herbicide of the present invention can also be used successfully in the ultra-low-volume process (ULV), it being possible to apply formulations comprising over 95% by weight of active compound, or even to apply the active compound without additives.

The following are examples of AHAS-inhibiting herbicide formulations for use in the methods of the present invention:

1. Products for dilution with water for foliar applications. For seed treatment purposes, such products may be applied to the seed diluted or undiluted.

A) Water-soluble concentrates (SL, LS)
Ten parts by weight of the AHAS-inhibiting herbicide are dissolved in 90 parts by weight of water or a water-soluble solvent. As an alternative, wetters or other auxiliaries are added. The AHAS-inhibiting herbicide dissolves upon dilution with water, whereby a formulation with 10% (w/w) of AHAS-inhibiting herbicide is obtained.

B) Dispersible concentrates (DC)
Twenty parts by weight of the AHAS-inhibiting herbicide are dissolved in 70 parts by weight of cyclohexanone with addition of 10 parts by weight of a dispersant, for example polyvinylpyrrolidone. Dilution with water gives a dispersion, whereby a formulation with 20% (w/w) of AHAS-inhibiting herbicide is obtained.

C) Emulsifiable concentrates (EC)
Fifteen parts by weight of the AHAS-inhibiting herbicide are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of AHAS-inhibiting herbicide is obtained.

D) Emulsions (EW, EO, ES)
Twenty-five parts by weight of the AHAS-inhibiting herbicide are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of AHAS-inhibiting herbicide is obtained.

E) Suspensions (SC, OD, FS)
In an agitated ball mill, 20 parts by weight of the AHAS-inhibiting herbicide are comminuted with addition of 10 parts by weight of dispersants, wetters and 70 parts by weight of water or of an organic solvent to give a fine AHAS-inhibiting herbicide suspension. Dilution with water gives a stable suspension of the AHAS-inhibiting herbicide, whereby a formulation with 20% (w/w) of AHAS-inhibiting herbicide is obtained.

F) Water-dispersible granules and water-soluble granules (WG, SG)
Fifty parts by weight of the AHAS-inhibiting herbicide are ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the AHAS-inhibiting herbicide, whereby a formulation with 50% (w/w) of AHAS-inhibiting herbicide is obtained.

G) Water-dispersible powders and water-soluble powders (WP, SP, SS, WS)
Seventy-five parts by weight of the AHAS-inhibiting herbicide are ground in a rotor-stator mill with addition of 25 parts by weight of dispersants, wetters and silica gel. Dilution with water gives a stable dispersion or solution of the AHAS-inhibiting herbicide, whereby a formulation with 75% (w/w) of AHAS-inhibiting herbicide is obtained.

H) Gel-Formulation (GF)
In an agitated ball mill, 20 parts by weight of the AHAS-inhibiting herbicide are comminuted with addition of 10 parts by weight of dispersants, 1 part by weight of a gelling agent wetters and 70 parts by weight of water or of an organic solvent to give a fine AHAS-inhibiting herbicide suspension. Dilution with water gives a stable suspension of the AHAS-inhibiting herbicide, whereby a formulation with 20% (w/w) of AHAS-inhibiting herbicide is obtained. This gel formulation is suitable for us as a seed treatment.

2. Products to be applied undiluted for foliar applications. For seed treatment purposes, such products may be applied to the seed diluted.

A) Dustable powders (DP, DS)

Five parts by weight of the AHAS-inhibiting herbicide are ground finely and mixed intimately with 95 parts by weight of finely divided kaolin. This gives a dustable product having 5% (w/w) of AHAS-inhibiting herbicide.

B) Granules (GR, FG, GG, MG)

One-half part by weight of the AHAS-inhibiting herbicide is ground finely and associated with 95.5 parts by weight of carriers, whereby a formulation with 0.5% (w/w) of AHAS-inhibiting herbicide is obtained. Current methods are extrusion, spray-drying or the fluidized bed. This gives granules to be applied undiluted for foliar use.

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, or either directly on the seeds.

In one embodiment an FS formulation is used for seed treatment. Typically, an FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

For seed treatment, seeds of the event 127 soybean plants of the present invention are treated with herbicides, such as herbicides selected from the group consisting of AHAS-inhibiting herbicides such as amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid, pyrithiobac, and mixtures thereof, or with a formulation comprising a AHAS-inhibiting herbicide.

The term seed treatment comprises all suitable seed treatment techniques known in the art, such as seed dressing, seed coating, seed dusting, seed soaking, and seed pelleting.

In accordance with one variant of the present invention, a further subject of the invention is a method of treating soil by the application, in particular into the seed drill: either of a granular formulation containing the AHAS-inhibiting herbicide as a composition/formulation (e.g., a granular formulation, with optionally one or more solid or liquid, agriculturally acceptable carriers and/or optionally with one or more agriculturally acceptable surfactants. This method is advantageously employed, for example, in seedbeds of cereals, maize, cotton, and sunflower.

The present invention also comprises seeds coated with or containing with a seed treatment formulation comprising at least one AHAS-inhibiting herbicide selected from the group consisting of amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halo sulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac.

The term "seed" embraces seeds and plant propagules of all kinds including but not limited to true seeds, seed pieces, suckers, corms, bulbs, fruit, tubers, cuttings, cut shoots and the like. In a preferred embodiment true seeds are employed. "True seed" refers to a ripened plant ovule containing an embryo, and enclosed within a seed coat or testa, as well as seed-like reproductive structures that can contain these enclosed in a pericarp or shell, for example, as a caryopsis or achene.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

The seed treatment application with the AHAS-inhibiting herbicide or with a formulation comprising the AHAS-inhibiting herbicide is carried out by spraying or dusting the seeds before sowing of the plants and before emergence of the plants.

In the treatment of seeds, the corresponding formulations are applied by treating the seeds with an effective amount of the AHAS-inhibiting herbicide or a formulation comprising the AHAS-inhibiting herbicide. Herein, the application rates are generally from 0.1 g to 10 kg of the a.i. (or of the mixture of a.i. or of the formulation) per 100 kg of seed, preferably from 1 g to 5 kg per 100 kg of seed, in particular from 1 g to 2.5 kg per 100 kg of seed. For specific crops such as lettuce the rate can be higher.

Any herbicide formulation applied over the event 127 soybean plant can be prepared as a "tank-mix" composition. In such embodiments, each ingredient or a combination of ingredients can be stored separately from one another. The ingredients can then be mixed with one another prior to application. Typically, such mixing occurs shortly before application. In a tank-mix process, each ingredient, before mixing, typically is present in water or a suitable organic solvent. Methods and guidance for the preparation of such formulations are known in the art.

The methods further allow for the development of herbicide combinations to be used with the event 127 soybean plants. In such methods, the environmental conditions in an area of cultivation are evaluated. Environmental conditions that can be evaluated include, but are not limited to, ground and surface water pollution concerns, intended use of the crop, crop tolerance, soil residuals, weeds present in area of cultivation, soil texture, pH of soil, amount of organic matter in soil, application equipment, and tillage practices. Upon the evaluation of the environmental conditions, an effective amount of a combination of herbicides can be applied to the crop, crop part, seed of the crop or area of cultivation.

In some embodiments, the herbicide applied to the event 127 soybean plants serves to prevent the initiation of growth of susceptible weeds or undesired plants and/or serve to cause damage to weeds or undesired plants that are growing in the area of interest. In some embodiments, the herbicide or herbicide mixture exert these effects on weeds or undesired plants affecting crops that are subsequently planted in the area of interest (i.e., field or area of cultivation). In the methods, the application of the herbicide combination need not occur at the same time. So long as the field in which the crop is planted contains detectable amounts of the first herbicide and the second herbicide is applied at some time during the period in which the crop is in the area of cultivation, the crop is considered to have been treated with a mixture of herbicides according to the invention. Thus, the provided methods encompass applications of herbicide which are "preemergent," "postemergent," "preplant incorporation" and/or which involve seed treatment prior to planting.

In addition, methods are provided for coating seeds of event 127 soybean plants. The methods comprise coating a seed with an effective amount of an herbicide or a combination of herbicides (as disclosed elsewhere herein). The seeds can then be planted in an area of cultivation. Further provided are seeds of event 127 plants having a coating comprising an effective amount of an herbicide or a combination of herbicides (as disclosed elsewhere herein).

"Preemergent" refers to an herbicide which is applied to an area of interest (e.g., a field or area of cultivation) before a plant emerges visibly from the soil and/or before germination of seed. "Postemergent" refers to an herbicide which is applied to an area after a plant emerges visibly from the soil. In some instances, the terms "preemergent" and "postemergent" are used with reference to a weed or undesired plant in an area of interest, and in some instances these terms are used with reference to a crop plant in an area of interest. When used with reference to a weed or undesired plant, these terms may apply to only a particular type of weed or species of weed or undesired plant that is present or believed to be present in the area of interest. While any herbicide may be applied in a preemergent and/or postemergent treatment, some herbicides are known to be more effective in controlling a weed or weeds or undesired plants when applied either preemergence or postemergence. For example, rimsulfuron has both preemergence and postemergence activity, while other herbicides have predominately preemergence (metolachlor) or postemergence (glyphosate) activity. These properties of particular herbicides are known in the art and are readily determined by one of skill in the art. Further, one of skill in the art would readily be able to select appropriate herbicides and application times for use with the transgenic plants of the invention and/or on areas in which transgenic plants of the invention are to be planted. "Preplant incorporation" involves the incorporation of compounds into the soil prior to planting.

Thus, improved methods of growing a crop and/or controlling weeds or undesired plants are provided such as, for example, "pre-planting burn down," where an area is treated with one or more herbicides prior to planting the crop of interest in order to better control weeds or undesired plants. Further provided are methods of growing a crop and/or controlling weeds or undesired plants which are "no-till" or "low-till" (also referred to as "reduced tillage"). In such methods, the soil is not cultivated or is cultivated less frequently during the growing cycle in comparison to traditional methods; these methods can save costs that would otherwise be incurred due to additional cultivation, including labor and fuel costs.

The methods encompass the use of simultaneous and/or sequential applications of multiple classes of herbicides. In some embodiments, the methods involve treating a plant of the invention and/or an area of interest (e.g., a field or area of cultivation) and/or weed and/or undesired plant with just one herbicide or other chemical such as, for example, an imidazolinone herbicide.

The time at which an herbicide is applied to an area of interest (and any plants therein) may be important in optimizing weed or undesired plant control. The time at which an herbicide is applied may be determined with reference to the size of plants and/or the stage of growth and/or development of plants in the area of interest, e.g., crop plants or weeds or undesired plants growing in the area. The stages of growth and/or development of plants are known in the art. For example, soybean plants normally progress through vegetative growth stages known as $V_E$ (emergence), $V_c$ (unifoliolate), $V_1$ (first trifoliolate), and $V_2$ to $V_N$. Soybeans then switch to the reproductive growth phase in response to photoperiod cues; reproductive stages include $R_1$ (beginning bloom), $R_2$ (full bloom), $R_3$ (beginning pod), $R_4$ (full pod), $R_5$ (beginning seed), $R_6$ (full seed), $R_7$ (beginning maturity), and $R_8$ (full maturity). Thus, for example, the time at which an herbicide or other chemical is applied to an area of interest in which plants are growing may be the time at which some or all of the plants in a particular area have reached at least a particular size and/or stage of growth and/or development, or the time at which some or all of the plants in a particular area have not yet reached a particular size and/or stage of growth and/or development.

In some embodiments, the event 127 soybean plants show improved tolerance to postemergence herbicide treatments. For example, the event 127 plants may be tolerant to higher doses of herbicide, tolerant to a broader range of herbicides (i.e., tolerance to more AHAS inhibitor chemistries), and/or may be tolerant to doses of herbicide applied at earlier or later times of development in comparison to an appropriate control plant.

Different chemicals such as herbicides have different "residual" effects, i.e., different amounts of time for which treatment with the chemical or herbicide continues to have an effect on plants growing in the treated area. Such effects may be desirable or undesirable, depending on the desired future purpose of the treated area (e.g., field or area of cultivation). Thus, a crop rotation scheme may be chosen based on residual effects from treatments that will be used for each crop and their effect on the crop that will subsequently be grown in the same area. One of skill in the art is familiar with techniques that can be used to evaluate the residual effect of an herbicide; for example, herbicides that act to inhibit AHAS vary in their residual activity levels. Residual activities for various herbicides are known in the art, and are also known to vary with various environmental factors such as, for example, soil moisture levels, temperature, pH, and soil composition (texture and organic matter). The event 127 soybean plants find particular use in methods of growing a crop where improved tolerance to residual activity of an herbicide is beneficial.

In addition, the soybean event 127 plants of the present invention provide improved tolerance to treatment with additional chemicals used on crops in conjunction with herbicide treatments, such as safeners, adjuvants such as ammonium sulfonate, and crop oil concentrate, and the like.

In addition, the disclosed methods can comprise the use of an AHAS-inhibiting herbicide or a mixture of herbicides, as well as, one or more other insecticides, fungicides, nematocides, bactericides, acaricides, growth regulators, chemosterilants, semiochemicals, repellents, attractants, pheromones, feeding stimulants or other biologically active compounds or entomopathogenic bacteria, virus, or fungi to form a multi-component mixture giving an even broader spectrum of agricultural protection. Examples of such agricultural protectants that can be used in methods include: insecticides such as abamectin, acephate, acetamiprid, amidoflumet (S-1955), avermectin, azadirachtin, azinphos-methyl, bifenthrin, bifenazate, buprofezin, carbofuran, cartap, chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyriprole, pyriproxyfen, rotenone, ryanodine, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron; fungicides such as acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazole, guazatine, imazalil, imibenconazole, iminoctadine, iodicarb, ipconazole, iprobenfos, iprodione, iprovalicarb, isoconazole, isoprothiolane, kasugamycin, kresoxim-methyl, mancozeb, mandipropamid, maneb, mapanipyrin, mefenoxam, mepronil, metalaxyl, metconazole, methasulfocarb, metiram, metominostrobin/fenominostrobin, mepanipyrim, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penthiopyrad, perfurazoate, phosphonic acid, phthalide, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pryazophos, pyrifenox, pyrimethanil, pyrifenox, pyroInitrine, pyroquilon, quinconazole, quinoxyfen, quintozene, silthiofam, simeconazole, spiroxamine, streptomycin, sulfur, tebuconazole, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimoprhamide tricyclazole, trifloxystrobin, triforine, triticonazole, uniconazole, validamycin, vinclozolin, zineb, ziram, and zoxamide; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *Aizawai, Bacillus thuringiensis* subsp. *Kurstaki,* and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV. The weight ratios of these various mixing partners to other compositions (e.g., herbicides) used in the methods typically are between 100:1 and 1:100, or between 30:1 and 1:30, between 10:1 and 1:10, or between 4:1 and 1:4.

Further provided are compositions comprising a biologically effective amount of an AHAS-inhibiting herbicide of interest or a mixture of herbicides, and an effective amount of at least one additional biologically active compound or agent and can further comprise at least one of a surfactant, a solid diluent or a liquid diluent. Examples of such biologically active compounds or agents are: insecticides such as abamectin, acephate, acetamiprid, amidoflumet (S-1955), avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenvalerate, fipronil, flonicamid, flucythrinate, tau-fluvalinate, flufenerim (UR-50701), flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin (BSN 2060), sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron; fungicides such as acibenzolar, azoxystrobin, benomyl, blasticidin-S, Bordeaux mixture (tribasic copper sulfate), bromuconazole, carpropamid, captafol, captan, carbendazim, chloroneb, chlorothalonil, copper oxychloride, copper salts, cyflufenamid, cymoxanil, cyproconazole, cyprodinil, (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenyl-amino)-4H-imid-azol-4-one (RP 407213), dimethomorph, dimoxystrobin, diniconazole, diniconazole-M, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), flumorf/flumorlin (SYP-L190), fluoxastrobin (HEC 5725), fluquinconazole, flusilazole, flutolanil, flutriafol, folpet, fosetyl-aluminum, furalaxyl, furametapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metomino-strobin/fenominostrobin (SSF-126), metrafenone (AC375839), myclobutanil, neo-asozin (ferric methane-arsonate), nicobifen (BAS 510), orysastrobin, oxadixyl, penconazole, pencycuron, probenazole, prochloraz, propamocarb, propiconazole, proquinazid (DPX-KQ926), prothioconazole (JAU 6476), pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *Aizawai, Bacillus thuringiensis* subsp. *Kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV. Methods may also comprise the use of plants genetically transformed to express proteins toxic to invertebrate pests (such as *Bacillus thuringiensis* delta-endotoxins). In such embodiments, the effect of exogenously applied invertebrate pest control compounds may be synergistic with the expressed toxin proteins.

Thus, the methods can employ an AHAS-inhibiting herbicide or AHAS-inhibiting herbicide combination and may further comprise the use of insecticides and/or fungicides, and/or other agricultural chemicals such as fertilizers. The use of such combined treatments can broaden the spectrum of activity against additional weed species and suppress the proliferation of any resistant biotypes.

Embodiments are further defined in the following Examples. It should be understood that these Examples are given by way of illustration only. From the above discussion and these Examples, one skilled in the art can ascertain the essential characteristics, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

EXAMPLES

Example 1

Preparation of Transgenic Plants

Transgenic soybean (*Glycine max* L.) plants were developed using a linearized fragment (PvuII) of DNA from plasmid pAC321 containing a mutant acetohydroxyacid synthase large subunit (AHASL) coding sequence providing resistance to imidazaolinone herbicides. The pAC321 plasmid contains a mutated *Arabidopsis thaliana* AHASL gene (csr1-2) coding sequence having an asparagine at a position corresponding to position 653, rather than the native serine (S653N). The AHAS (S653N) coding sequence is under the control of the native *A. thaliana* AHAS promoter sequence and transcription termination sequence. See, e.g. U.S. Publication No. 2005/0034187, the entirety of which is hereby incorporated by reference. The PvuII fragment includes the *Arabidopsis* AHASL promoter, the herbicide-tolerant *Arabidopsis* AHASL1(csr1-2) coding sequence and the *Arabidopsis* AHASL terminator. This promoter, coding sequence and terminator cassette is referred to herein as the csr1-2 cassette.

Embryogenic axis tissue derived from the apical meristem of a single soybean seed of the commercial variety "Conquista" was used for biolistic transformation. Biolistic transformation (microprojectile or particle bombardment) (Aragão, F. J. L., et al., Theor. Appl. Genet. 1996; 93:142-150) was used to produce soybean transformation events containing the csr1-2 gene. Prior to bombardment, DNA containing the csr1-2 gene fragment was precipitated onto microscopic gold particles. The precipitated DNA and particles were then placed onto a plastic macrocarrier and accelerated at high velocity such that a stopping screen retained the macrocarrier. The particles with DNA were permitted to continue their flight and eventual penetration and incorporation into the soybean plant cells. Bombarded cells were transferred to a selective media containing the equivalent of 50 g ai/ha imazapyr, an imidazolinone herbicide, and only those cells transformed with the csr1-2 gene continued to grow. From this process a tolerant T0 plant was identified and named Soybean event 127 (Table 1).

Example 2

Line Development

The initial transformant of soybean event 127 was maintained by self-crossing ("selfing") to the T4 generation as provided in Table 1 below.

TABLE 1

Early generation development of soybean event 127

| Generation | Selection criteria | Material Selected to advance |
| --- | --- | --- |
| T0 | 50 g ai/ha imazapyr | T1 seed from 1 T0 plant |
| T1 | 100 g ai/ha imazapyr | Bulk T2 seed from 3 T1 plants |
| T2 | 100 g ai/ha imazapyr | T3 seed from 10 individual T2 plants |
| T3 | 100 g ai/ha imazapyr | Bulk T4 seed from 10 T3 plants per each of 10 T2:3 families (E01 through E10) |
| T4 | | 50 T4 seeds from each of the 9 T2:3 families |

Genetic analysis of seeds from nine T3 plants (E01, E02, E03, E04, E05, E06, E07, E09, and E10) revealed that transgene segregation did not always follow simple Mendelian patterns, suggesting that there more than one active locus. The T4 progeny from T3 plants (E09, E10, and E05) that exhibited Medelian segregation for tolerance to imazapyr and which had a normal phenotype were crossed to non-transgenic varieties (BRS137, Conquista, and BR97-7066) to develop four populations (Table 2, FIG. 2).

TABLE 2

Development and identification of soybean populations containing event 127

| Cross | F1 | F2 | F3 | F4 | F5 |
|---|---|---|---|---|---|
| T4-E09 X BRS 137 | F1 | IMI01P1 | V2-1 | P9-1 | V03-541 |
|  |  |  |  |  | V03-565 to 567 |
|  |  |  | V2-2 | P9-2 | V03-542 |
|  |  |  |  |  | V03-568 to 570 |
|  |  |  | V3-1 | P9-3 | V03-543 |
|  |  |  |  |  | V03-571 to 573 |
|  |  |  | V9-1 | P35-3 | V03-545 |
|  |  |  |  |  | V03-575 to 576 |
|  |  | IMI245 | V288 (211) | V03-546 | V03-602 to 611 |
| T4-E10 X Conquista | F1 | IMI209 | V283 (193) | V03-551 | V03-586 to 601 |
| T4-E05 X BR97-7066 | F1 | IMI63 | V03-447 | V03-613 |  |
|  |  |  | V03-448 | V03-614 |  |
|  |  |  |  | V03-615 |  |
| T4-E09 X Conquista | F1 | IMI141 | V259 (125) | V03-547 |  |
|  |  |  | V260 (126) | V03-548 |  |
|  |  |  | V261 (131) | V03-549 |  |
|  |  |  | V261 (130) | V03-550 |  |
|  |  |  | V260 (128) | V03-563 |  |

In the F2 and F3 generations, families and individual plants were selected that had a normal phenotype and tolerance to imazapyr in the greenhouse. The segregation pattern (38 tolerant:13 intolerant) for tolerance to imazapyr (100 g ai/ha) in the F2 population of a cross between transgenic Conquista (T4-E10)× nontransgenic Conquista showed that a single dominant gene in transgenic line V03-603 (CV-603), containing event 127, controls tolerance to imazapyr.

Subsequent field trials using F4 and/or F5 lines from each of four crosses (Table 2) support the selection of the line V03-603, containing event 127 as the elite soybean line for subsequent analysis and development. The field trials were planted in four locations using a randomized complete block design with three replications and a split-plot treatment design. Entries were whole plots and imazapyr application rates (0, 70, 240, or 280 g ai/ha) were subplots. Plants were sprayed 18-21 days after planting and evaluated 14 days after application. Plants were evaluated for percent injury (0=no dead plants in plot to 100=all plants dead in plot). Additional data collected included plant height, seed yield, seed size, days to flowering and days to maturity.

TABLE 3

Percent injury to soybean lines containing event 127 14 days after application of different rates of imazapyr

| | Location | | | | | | | | | | | | | | | |
|---|---|---|---|---|---|---|---|---|---|---|---|---|---|---|---|---|
| | Londrina | | | | Campinas (1) | | | | Campinas (2) | | | | Mean across locations | | | |
| | Rate of imazapyr (g ai/ha) | | | | | | | | | | | | | | | |
| Line | 0 | 70 | 140 | 280 | 0 | 70 | 140 | 280 | 0 | 70 | 140 | 280 | 0 | 70 | 140 | 280 |
| V03-541 | 0 | 1.7 | 10 | 16.7 | 0 | 1 | 14 | 32.3 | 0 | 3.7 | 13.3 | 33 | 0 | 2.1 | 12.4 | 27.3 |
| V03-542 | 0 | 0 | 4.3 | 10 | 0 | 1.3 | 9 | 21 | 0 | 2.3 | 7 | 28 | 0 | 1.2 | 6.8 | 19.7 |
| V03-543 | 0 | 0 | 2.7 | 8.3 | 0 | 1.3 | 4.7 | 18.3 | 0 | 2.3 | 5 | 18 | 0 | 1.2 | 4.1 | 14.9 |
| V03-544 | 0 | 0 | 3.3 | 9 | 0 | 0.7 | 3 | 14.7 | 0 | 1.7 | 5 | 15 | 0 | 0.8 | 3.8 | 12.9 |
| V03-545 | 0 | 0 | 8.3 | 15 | 0 | 0 | 7 | 18 | 0 | 2.3 | 6 | 23 | 0 | 0.8 | 7.1 | 18.7 |
| Conquista | 0 | 90 | 95 | 98 | 0 | 90 | 90 | 90 | 0 | 95 | 95 | 95 | 0 | 91.7 | 93.3 | 94.3 |

TABLE 4

Percent injury to soybean lines containing event 127 14 days after application of different rates of imazapyr

| | Location | | | | | | | | | | | | |
|---|---|---|---|---|---|---|---|---|---|---|---|---|---|
| | Londrina | | | | Ponta Grossa | | | | Mean across locations | | | |
| | Rate of imazapyr (g ai/ha) | | | | | | | | | | | | |
| Line | 0 | 70 | 140 | 280 | 0 | 70 | 140 | 280 | 0 | 70 | 140 | 280 |
| V03-589 | 0 | 0 | 4.7 | 9.3 | 0 | 3.3 | 10 | 23.3 | 0 | 1.7 | 7.4 | 16.3 |
| V03-590 | 0 | 0 | 4.7 | 11.7 | 0 | 1.7 | 8.3 | 18.3 | 0 | 0.9 | 6.5 | 15 |
| V03-598 | 0 | 0 | 4.3 | 9 | 0 | 1.7 | 11.7 | 18.3 | 0 | 0.9 | 8 | 13.7 |
| V03-602 | 0 | 0 | 4.3 | 12.3 | 0 | 1.7 | 11.7 | 20 | 0 | 0.9 | 8 | 16.2 |
| V03-603 | 0 | 0 | 5.7 | 13.3 | 0 | 1.7 | 6.7 | 16.7 | 0 | 0.9 | 6.2 | 15.0 |
| V03-607 | 0 | 4 | 8.3 | 15.7 | 0 | 3.3 | 13.3 | 23.3 | 0 | 3.7 | 10.8 | 19.5 |
| V03-610 | 0 | 0 | 7.3 | 12.3 | 0 | 8.3 | 13.3 | 18.3 | 0 | 4.2 | 10.3 | 15.3 |
| Conquista | 0 | 90 | 95 | 98 | 0 | 90 | 90 | 90 | 0 | 90 | 92.5 | 94.0 |

TABLE 5

Percent injury to soybean lines containing event 127 14 days after application of different rates of imazapyr

| | Location | | | | | | | | | | | | | | | | | | |
|---|---|---|---|---|---|---|---|---|---|---|---|---|---|---|---|---|---|---|---|
| | Londrina | | | | Ponta Grossa | | | | Campinas (1) | | | | Campinas (2) | | | | Mean across locations | | |
| | | | | | | | | Rate of imazapyr (g ai/ha) | | | | | | | | | | | |
| Line | 0 | 70 | 140 | 280 | 0 | 70 | 140 | 280 | 0 | 70 | 140 | 280 | 0 | 70 | 140 | 280 | 0 | 70 | 140 | 280 |
| 613 | 0 | 1.7 | 6.7 | 12.3 | 0 | 0 | 6.7 | 21.7 | 0 | 0 | 6 | 17.7 | 0 | 1.7 | 5 | 17 | 0 | 0.9 | 6.1 | 17.2 |
| 614 | 0 | 0 | 8.3 | 15 | 0 | 3.3 | 11.7 | 23.3 | 0 | 0 | 4.3 | 16.3 | 0 | 1.3 | 7 | 18 | 0 | 1.2 | 7.8 | 18.2 |
| 615 | 0 | 1.7 | 9 | 13.7 | 0 | 0 | 11.7 | 23.3 | 0 | 0 | 8.3 | 18.7 | 0 | 2 | 9 | 20 | 0 | 0.9 | 9.5 | 18.9 |
| Conquista | 0 | 90 | 95 | 98 | 0 | 90 | 90 | 90 | 0 | 95 | 95 | 95 | 0 | 81.7 | 83.3 | 88.3 | 0 | 89.2 | 90.8 | 92.8 |

Example 3

Molecular Characterization

A: DNA and RNA Isolation and Quantitation Methods

DNA was isolated from soybean leaf tissue via a modified cetyl trimethyl ammonium bromide (CTAB) method (Carlson et al., 1991). Silica gel-desiccated leaf tissue was frozen with liquid nitrogen and ground with an Autogrinder (Autogen; Holliston, Mass.). The ground tissue was incubated with preheated extraction buffer consisting of 2% (w/v) CTAB, 100 mM Tris-HCl, 1.4 M NaCl, 1% (w/v) polyvinylpyrrolidone (PVP), 20 mM ethylenediamine tetraacetic acid (EDTA), pH 9.5 (5 ml/60 mg dried leaf tissue) and β-mercaptoethanol (10 µl/ml buffer) at 74° C. for 20 mM. After centrifugation at 2440×g for 10 min, the supernatant was extracted twice with an equal volume of chloroform/isoamyl alcohol (24:1). DNA was precipitated with 0.7 volume of isopropanol and dissolved in TE buffer (10 mM Tris-HCl, 1 mM EDTA, pH 8.0) with 0.5 mg/ml RNase A (Invitrogen; Carlsbad, Calif.) added to a final concentration of about 500 ng/µl. The isolated DNA was quantified with Hoechst 33258 dye (Invitrogen) with calf thymus DNA (Invitrogen) used as the DNA standard on a Packard FluoroCount™ BF 10000 Microplate Fluorometer (Packard Instrument Company; Meriden, Conn.) according to the fluorometer user manual.

Total RNA was extracted from silica gel-desiccated young leaves derived from F7 and F8 generation plants of Event 127 and from leaves of the non-transgenic parental soybean variety Conquista with the Qiagen RNeasy Mini Kit (Qiagen; Valencia, Calif.). About 25 mg of silica gel-desiccated leaf tissue was frozen with liquid nitrogen and ground with an Autogrinder. The total RNA isolation procedure was carried out according to the manufacturer's directions. On-column DNase digestion was performed with RNase-Free DNase (Qiagen) to eliminate any soybean genomic DNA from the total RNA preparation according to the recommendation in the RNeasy Mini Kit user manual. The isolated RNA was quantitated by measuring the absorbance at 260 nm using a BioMate™ 3 spectrophotometer (Thermo Electron Corporation; Waltham, Mass.).

B: Probe Isolation and Labeling Methods.

Figure 1B:
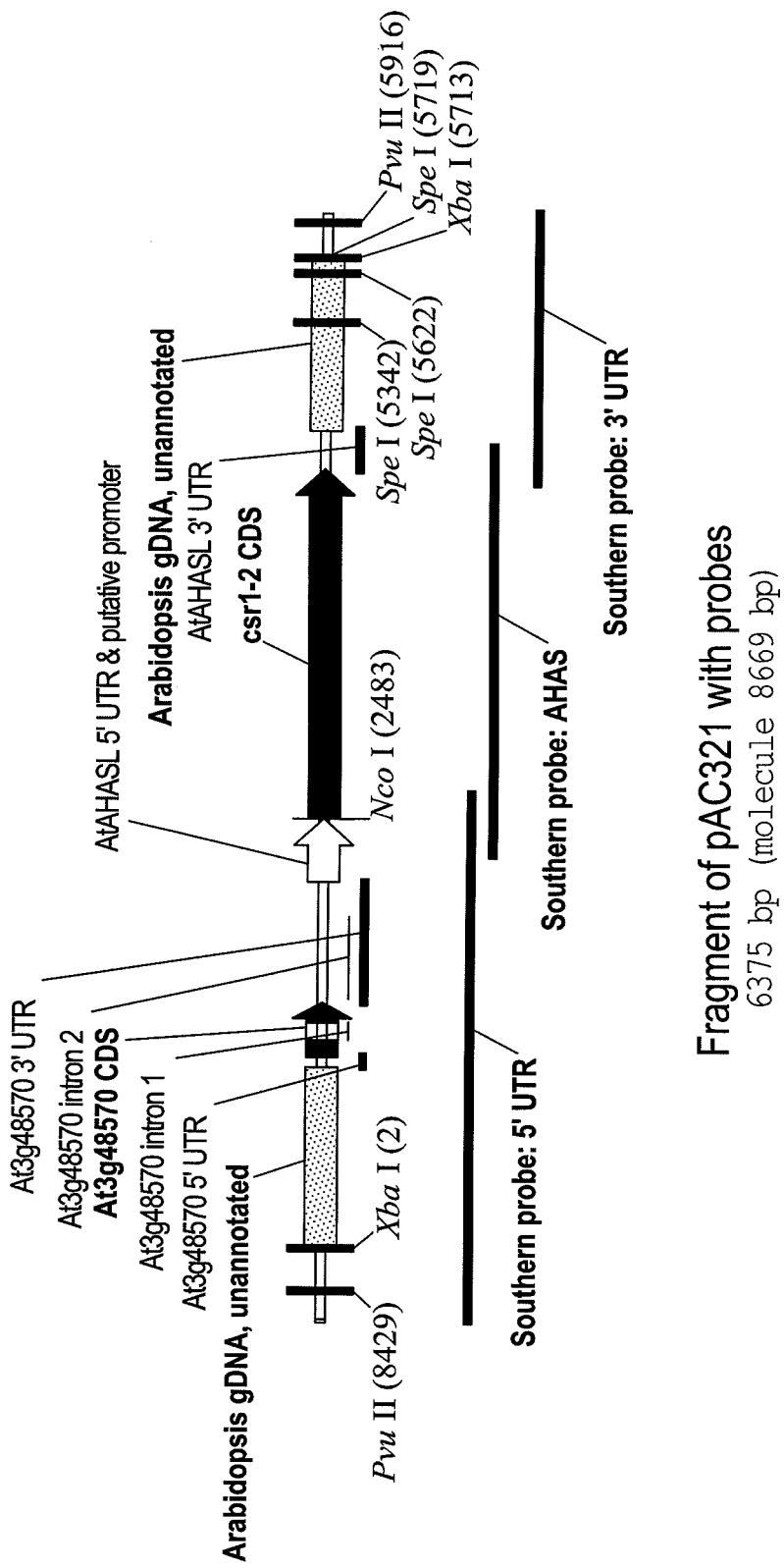
FIG. 1B provides a schematic representation of the PvuII fragment of pAC321 containing the AHASL 5' UTR, csr1-2 coding sequence and AHASL 3' UTR that was used for transformation. The restriction sites of the enzymes (NcoI, XbaI, SpeI) used for Southern blot analyses of copy number, absence of backbone and intergenerational stability are indicated.

The location of DNA fragments used as transgene probes are indicated in FIG. 1B. The vector backbone probes are indicated in FIG. 5C. PCR primers for use in generating the identified transgene and vector probes are provided in Table 3 below. Together these 5 overlapping probes span the entire plasmid. Specifically, probe 1 spans the AHASL promoter region, probe 2 the csr1-2 coding sequence, probe 3 the AHASL terminator region, and probes 4 and 5 together cover the complete vector backbone (VB). The probe DNA fragments were generated by PCR amplification using plasmid pAC321 as a template. The probes (25-50 ng each) were radiolabeled with 50 µCi of ($\alpha$-$^{32}$P)-dCTP (3000 Ci/mmol) (MP Biomedicals; Irvine, Calif.) using the Rediprime™ II DNA Labeling System (Amersham; Piscataway, N.J.) according to the manufacturer's instructions. The labeled probes were purified with a Spin-X® Centrifuge Tube Filter (Corning Costar Corporation; Acton, Mass.).

TABLE 6

Primers Used to Generate Probes for Southern Blot Analysis

| Purpose | Direction | Primer Sequence 5'-3' | Position (SEQ ID NO: 1) | SEQ ID NO: |
|---|---|---|---|---|
| Probe 1 | Forward | TGCGTTATCCCCTGATTCTG | 8261-8280 | 7 |
| 5' UTR | Reverse | TGTTGGGGTTTAGGGAG | 2597-2613 | 8 |
| Probe 2 | Forward | CGAAGGCTCAATCACAAATAC | 2269-2289 | 9 |
| AHASL | Reverse | AGCAGGCAGATCAACAAC | 4604-4621 | 10 |
| Probe 3 | Forward | GAACATGTGTTGCCGATGAT | 4416-4435 | 11 |
| 3' UTR | Reverse | CGCAACTGTTGGGAAGGG | 5949-5966 | 12 |
| Probe 4 | Forward | GTTTTACAACGTCGTGACTG | 5839-5858 | 13 |
| VP1 | Reverse | CGGTTAGCTCCTTCGGTC | 6997-7014 | 14 |
| Probe 5 | Forward | CACTGCGGCCAACTTACT | 6962-6979 | 15 |
| VP2 | Reverse | CTTGGCGTAATCATGGTC | 8592-8609 | 16 |

C: Copy Number, Insert Integrity and Stability.

Figure 3:
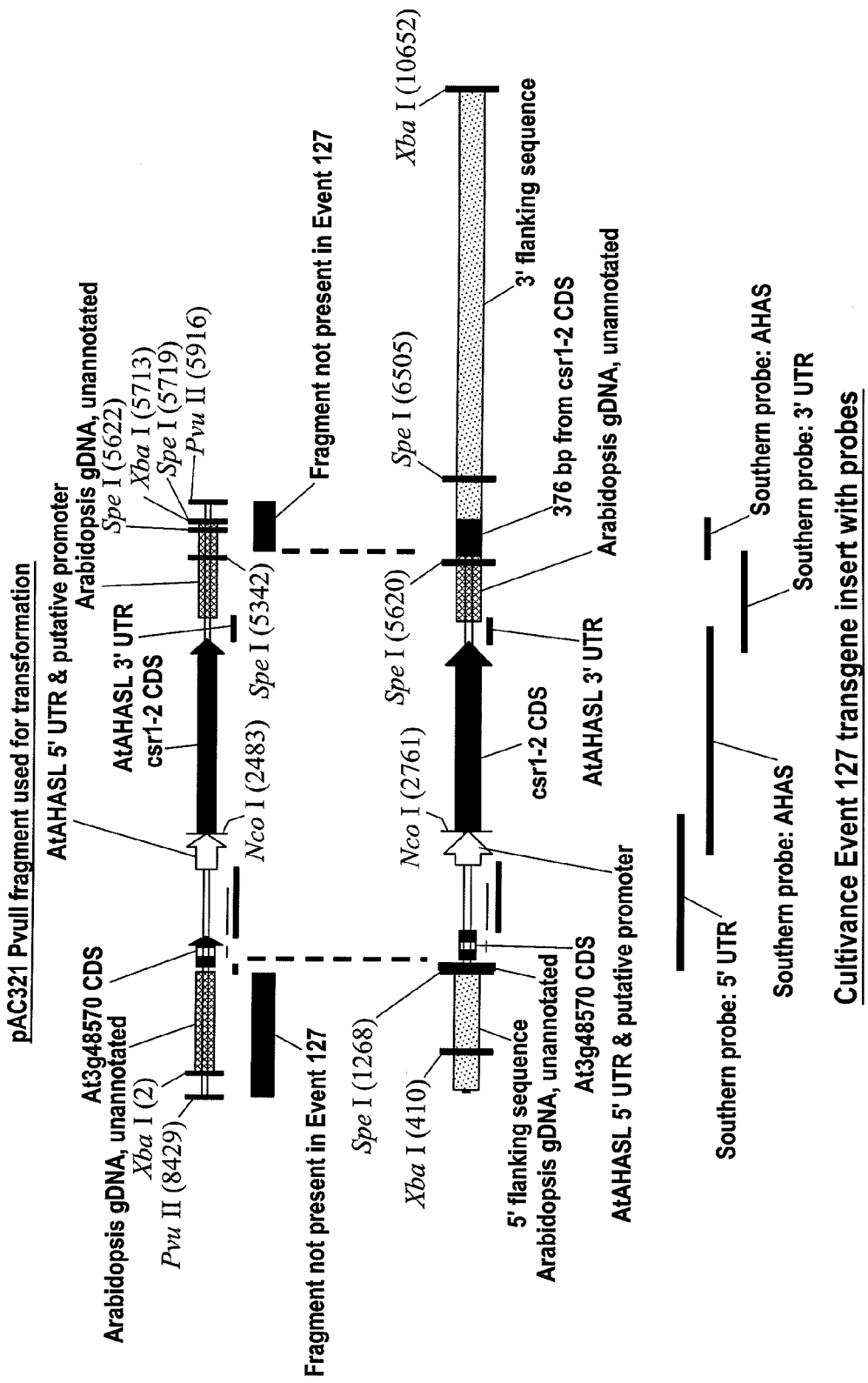
FIG. 3 provides a schematic representation of an alignment of the pAC321 PvuII transformation fragment with the soybean event 127 Insert.

Southern blot analyses were used to determine the number of copies and the integrity of the csr1-2 expression cassette as well as to confirm the absence of plasmid backbone in Event 127. Restriction enzymes NcoI, SpeI and XbaI were used to digest genomic DNA obtained from an event 127 plant and non-transgenic control Conquista. The pAC321 PvuII transformation fragment was aligned with the soybean event 127 insert in FIG. 3. The PvuII fragment from plasmid pAC321 that was used to transform soybean is shown in the upper portion of FIG. 3. Parts of this fragment that are not contained within the transgene insert in Soybean Event 127 are indicated by boxes filled with diagonal stripes. Characteristics of the transgene insert and the flanking genomic soybean DNA in Soybean Event 127 are shown in the lower portion of the figure. The DNA between the vertical dotted lines that are drawn between the maps of the PvuII transformation fragment and the transgene insertion region is common to both DNA fragments. Restriction sites relevant to the Southern blot analysis are indicated. The numbering system of the PvuII transformation fragment corresponds to that of the pAC321 plasmid map in FIG. 1. The numbering system for the Soybean Event 127 insert corresponds to that in FIG. 8, where #1 is the first nucleotide at the 5' end of the soybean genomic flanking sequence (positions 1-1311 represent the 5' flanking DNA, positions 1312-6069 represent the insert DNA encoding a modified AHASL protein, and positions 6070-10 656 represent the 3' flanking DNA). A single NcoI restriction site in the csr1-2 cassette is located at the 5' end of the csr1-2 coding sequence and digestion of genomic DNA of Event 127 with NcoI was predicted to generate two fragments that contain DNA from the csr1-2 cassette. Both fragments are defined by the NcoI site in the csr1-2 cassette and by the nearest NcoI sites in the flanking soybean genomic sequence. There is one SpeI restriction site in the 5' flanking soybean genomic sequence and two SpeI restriction sites downstream of the AHASL 3' UTR in event 127. The XbaI restriction sites flank the complete csr1-2 expression cassette. The number and sizes of the DNA fragments expected to be detected by Southern hybridization are listed in Table 7 below.

TABLE 7

The number and sizes of the DNA fragments expected to be detected by Southern hybridization

| FIG. | Probe | Restriction Enzyme | Predicted Fragment Size from Event 127 Insert (bp)[a] | Observed Event 127 Fragment Size | Predicted Fragment Size from Plasmid pAC321 (bp) | Observed Plasmid Fragment Size |
|---|---|---|---|---|---|---|
| 4A | 5' UTR | NcoI | >2760 | ~4500 | 8669 | ~9000 |
|  |  | SpeI | 4352 | ~4400 | 8292 | ~8500 |
|  |  | XbaI | 10242 | ~10000 | 5711[b] | ~5500 |
|  |  |  |  |  | 2958 | ~3000 |
| 4B | AHAS | NcoI | >7896 | ~9000 | 8669 | ~9000 |
|  |  | SpeI | 4352 | ~4400 | 8292 | ~8500 |
|  |  |  | 885 | ~800[c] |  |  |
|  |  | XbaI | 10242 | ~10000 | 5711 | ~5500 |
| 4C | 3' UTR | NcoI | >7896 | ~9000 | 8669 | ~9000 |
|  |  | SpeI | 4352 | ~4400 | 8292 | ~8500 |
|  |  |  |  |  | 280 |  |
|  |  |  |  |  | 97 |  |
|  |  | XbaI | 10242 | ~10000 | 5711[b] | ~5500 |
|  |  |  |  |  | 2958 | ~3000 |
| 5A | VP1 | NcoI | none | none | 8669 | ~9000 |
|  |  | SpeI | none | none | 8292 | ~8500 |
|  |  | XbaI | none | none | 2958 | ~3000 |
| 5B | VP2 | NcoI | none | none | 8669 | ~9000 |
|  |  | SpeI | none | none | 8292 | ~8500 |
|  |  | XbaI | none | none | 2958 | ~3000 |

[a]The predicted fragment size is estimated based on the cloned insert and flanking sequences in Event 127.
[b]The 5' UTR probe and the 3' UTR probe each overlap a XbaI site and therefore hybridize to both XbaI fragments of the plasmid.
[c]Sequence analysis of the Event 127 insert indicates that a small portion of the csr1-2 coding region was duplicated immediately upstream of the 3' transgene integration site, confirming the identity of the 800 by band seen in these Southern blots.

Figure 4D:
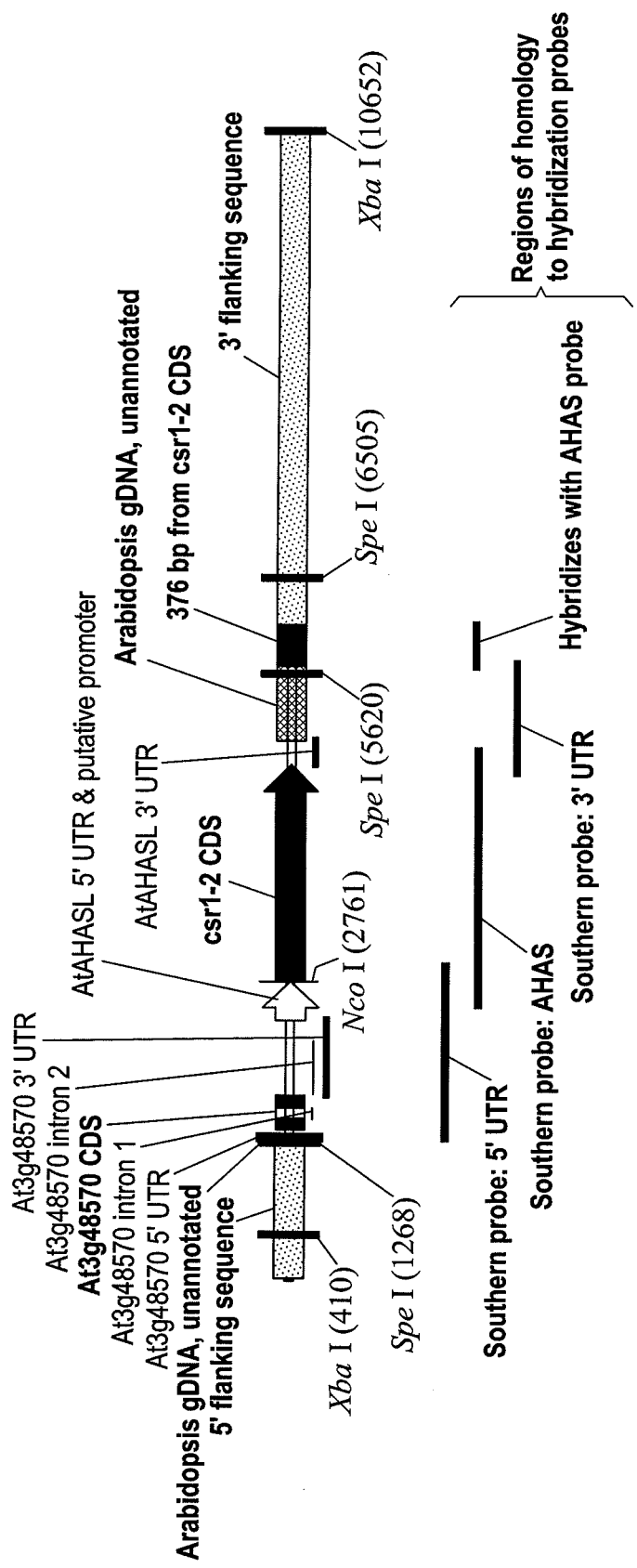
FIG. 4D provides a schematic representation of the relative locations of the probes used in the hybridization experiments.

The predicted fragment sizes are estimated based on the cloned insert and flanking sequences in event 127 plants. The 5' UTR probe and the 3' UTR probe each overlap an XbaI site and therefore hybridize to both XbaI fragments of the plasmid pAC321 (marked with dots in lane 11 of FIGS. 4A and 4C). The sequence analysis of the event 127 region indicated that a small portion of the csr1-2 coding region was duplicated immediately upstream of the 3' transgene integration site, confirming the identity of the 800 bp band identified in the Southern blot results.

Genomic DNA (7 μg) from the F8 generation of Event 127 and from the non-transgenic control Conquista was digested overnight in a volume of 40 μl with the restriction enzymes listed above (8 units/μg DNA) under the conditions specified by the enzyme manufacturers (New England Biolabs; Ipswich, Mass.; or Amersham). Restriction digests were separated by electrophoresis in 10 cm long 0.8% agarose gels. The DNA was further fragmented by soaking the gels in 0.25 N HCl for about 20 min and were denatured with 0.4 N NaOH for about 30 min. The gels were rinsed with 2× NaCl/sodium citrate solution (SSC) and the denatured DNA was transferred onto Hybond N+nylon membrane (Amersham) using 0.4 N NaOH as a transfer buffer.

Southern hybridization was carried out according to Sambrook et al. (1989). The membranes were prehybridized at 65° C. for 2-4 h and hybridized at 65° C. overnight in 20-30 ml (about 0.2 ml/cm$^2$) of hybridization buffer (2×SSC, 0.6% SDS, 50 mM Na$_2$HPO$_4$, 1×Denhardt's solution, 2.5 mM EDTA, 5% dextran sulfate, pH 7.2) in a Hybaid MAXI 14 Hybridization Oven (Thermo Electron Corporation). After hybridization, the membranes were washed with 2×SSC, 0.5% SDS (1 ml/cm$^2$) at room temperature for 15 min, 2×SSC, 0.1% SDS (4 ml/cm$^2$) at 65° C. for 30 min, and finally with 0.1×SSC, 0.1% SDS (4 ml/cm$^2$) at 65° C. for 15 min. After washing, the membranes were wrapped in plastic wrap and exposed to Hyperfilm™ MP film (Amersham) for 2-5 days, depending on the radioactive signal intensity, in cassettes with intensifying screens at −80° C.

Figure 2:
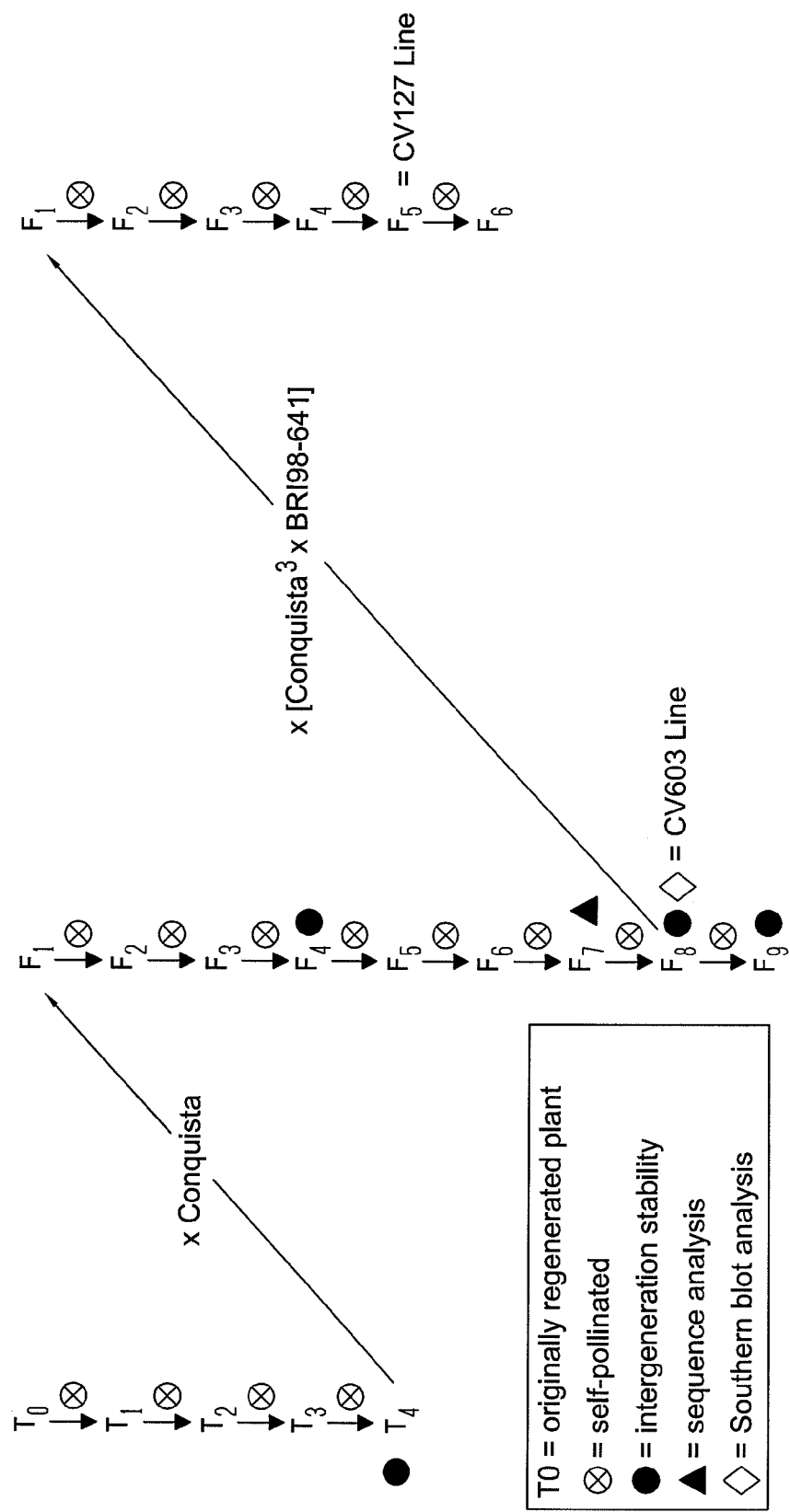
FIG. 2 provides a schematic representation of the breeding history of one example of a soybean event 127 plant.

Southern blot analyses were also conducted as described above to monitor the stability of the insert across multiple generations. Plant material was obtained from the T4, F4, F8 and F9 generations (FIG. 2). Genomic DNA from these samples was digested with NcoI and SpeI (as described above) and Southern blot analysis was carried out as described above.

The copy number of the insert in Event 127 was evaluated by Southern blot analysis of genomic DNA from Event 127 F8 generation plants digested with NcoI, SpeI and XbaI restriction enzymes using the method described above.

The results of the Southern blot analyses are provided in FIGS. 4A, 4B, and 4C. Genomic DNA of non-transgenic soybean variety Conquista (lanes 1, 5 and 9); Conquista spiked with 1-(lanes 2, 6 and 10); or 2-genome copy equivalents of pAC321 (lanes 3, 7 and 11); and genomic DNA of Soybean Event 127 from the F8 generation (lanes 4, 8 and 12) were digested with NcoI (1-4), SpeI (5-8) and XbaI (9-12) restriction enzymes as described. Blots were hybridized with probe 5' UTR (FIG. 4 A), probe AHAS (FIG. 4 B) and probe 3' UTR (FIG. 4 C). The first and last lanes (labeled M) contain a λ/HindIII ladder; band sizes are indicated in kilobases. FIG. 4 D indicates regions of homology between the Southern hybridization probes and the Event 127 insert. The arrow in FIG. 4 B indicates an approximately 885 bp SpeI fragment containing an additional 376 bp fragment of csr1-2 present in Event 127 at the 3' flanking sequence junction.

Non-transgenic Conquista DNA digested with all three restriction enzymes and hybridized with the three probes did not show any signal, indicating that neither the endogenous soybean AHASL gene nor the endogenous soybean Sec61γ subunit gene are detected at the Southern blot stringency conditions used (FIG. 4, lanes 1, 5 and 9). DNA samples from Event 127 F8 generation treated with the different enzyme and probe combinations all gave single bands (FIGS. 4A, B, and C, lanes 4, 8 and 12) except for the SpeI digest hybridized with the AHASL coding sequence probe, which had an additional small band of about 800 bp (FIG. 4B, lane 8, arrow). This AHASL-hybridizing 800 bp SpeI fragment is consistent with the observation that a small fragment of the AHASL coding sequence being repeated at the 3' flanking sequence junction in Event 127 (see section on Complete Sequence; Example 3E). All major bands had signal intensities roughly similar to the one-genome copy equivalent of pAC321.

Genomic DNA from Event 127 that was digested with NcoI and probed with At AHASL 5' UTR produced a hybridizing band approximately 4.5 kb in size. The size of this band is consistent with the production of a single DNA fragment defined by the NcoI site within the insert (nt 2761, FIG. 4D) and an NcoI site approximately 4.5 kb upstream in the 5' genomic soybean flanking sequence. The same digest probed with either the AtAHASL coding sequence or AtAHASL 3'UTR produced a hybridizing band approximately 9.0 kb in size. The size of this band is consistent with a single DNA fragment defined by the NcoI site in the insert (nt 2761, FIG. 4D) and an NcoI site approximately 9.0 kb downstream in the 3' soybean genomic flanking sequence.

Digestion of Event 127 genomic DNA with SpeI and probed with At AHASL 5' UTR produced a hybridizing band of approximate size 4.4 kb. This is consistent with the production of a single DNA fragment from a SpeI site in the insert (nt 5620, FIG. 4 D) and a SpeI restriction site approximately 4.4 kb upstream in the 5' DNA flanking sequence of the soybean genome (nt 1268, FIG. 4 D). The presence of this upstream SpeI site was confirmed in the analysis of the 5' flanking sequence of event 127 (See, section on Flanking sequence; Example 3D). The same digest probed with either the At AHASL coding sequence or the At AHASL 3' UTR also produced a 4.4 kb hybridizing band corresponding to the same fragment described above. In addition, a hybridizing band of approximate size 0.8 kb was detected when the SpeI digest was probed with At AHASL coding sequence, consistent with a single SpeI DNA fragment containing the 376 bp segment of the csr1-2 gene at the 3' flanking DNA sequence junction. This hybridizing fragment was produced from the SpeI site in the DNA insert and a SpeI site 0.8 kb downstream in the soybean genome (nt 5620-6505, FIG. 4 D). The 0.8 kb hybridizing band was not detected by the At AHASL 3' UTR probe, indicating that At AHASL 3' UTR DNA was not included in the 0.8 kb fragment, and the SpeI nt 5620 site in the insert is adjacent to the 376 bp segment of the csr1-2 gene. Therefore, SpeI restriction enzyme sites at nucleotide 5622 and 5719 in the linear PvuII fragment of plasmid pAC321 used for transformation (shown in FIG. 1B) were not included in the DNA insert in the event 127 genome. This was confirmed by DNA sequence analysis of the DNA insert (See, Complete Sequence section; Example 3E). The smaller predicted SpeI fragments of 280 and 97 bp in the pAC321-spiked controls would produce signal below the level of detection using this method.

Event 127 genomic DNA when digested with XbaI and probed with At AHASL 5' UTR shows a single hybridizing band of approximate size 10 kb. Based on the positions of the XbaI restriction sites in the linear DNA used for transformation (FIG. 1B), a hybridizing band of approximately 5.7 kb was expected, produced from within the DNA insert in the event 127 genome. However, DNA sequence analysis of the DNA insert in event 127 showed that neither of the XbaI restriction sites in the linear transformation DNA was included in the DNA insert (See, section on Complete Sequence; Example 3E). Therefore, the 10 kb hybridizing band was produced from XbaI restriction sites within the 5' and 3' DNA sequences flanking the insert (nt 410 and 10652, FIG. 4D). Accordingly, the same digest probed with either the At AHASL coding sequence or At AHASL 3' UTR produced the same 10 kb hybridizing band corresponding to the same DNA fragment described above.

Analysis of the number and size of all hybridizing bands on the Southern blots shown in FIG. 4 is consistent with the integration of a single DNA insert in the event 127 soybean genome containing a single functional copy of the csr1-2 gene, as well as coding sequences for the protein SEC61γ on the 5' end of the csr1-2 gene, and a single DNA fragment containing a 376 bp segment of the csr1-2 gene at the 3' end of the insert.

Although the transformation was carried out with the PvuII restriction fragment of pAC321 that did not include vector backbone DNA, Southern blot studies were conducted to confirm the absence of plasmid pAC321 vector DNA in the event 127 genome. In order to determine whether there was any vector backbone integrated in Event 127, the same set of blots used for Southern analysis described above (FIG. 4) was hybridized with two vector backbone-specific probes (FIG. 5). As expected, no hybridizing bands were detected in lanes containing non-transgenic Conquista genomic DNA. Non-transgenic Conquista genomic DNA spiked with one- or two-genome copy equivalents of transformation plasmid pAC321 showed hybridizing bands of the expected sizes (Table 7). The blot was hybridized with probe VP1 (FIG. 5 A) and probe VP2 (FIG. 5 B). No hybridizing bands were detected in event 127 F8 generation DNA, indicating that no vector backbone DNA was integrated into the soybean genome in this event. FIG. 5 C indicates the positions of probes VP1 and VP2 relative to the components of pAC321.

Figure 6D:
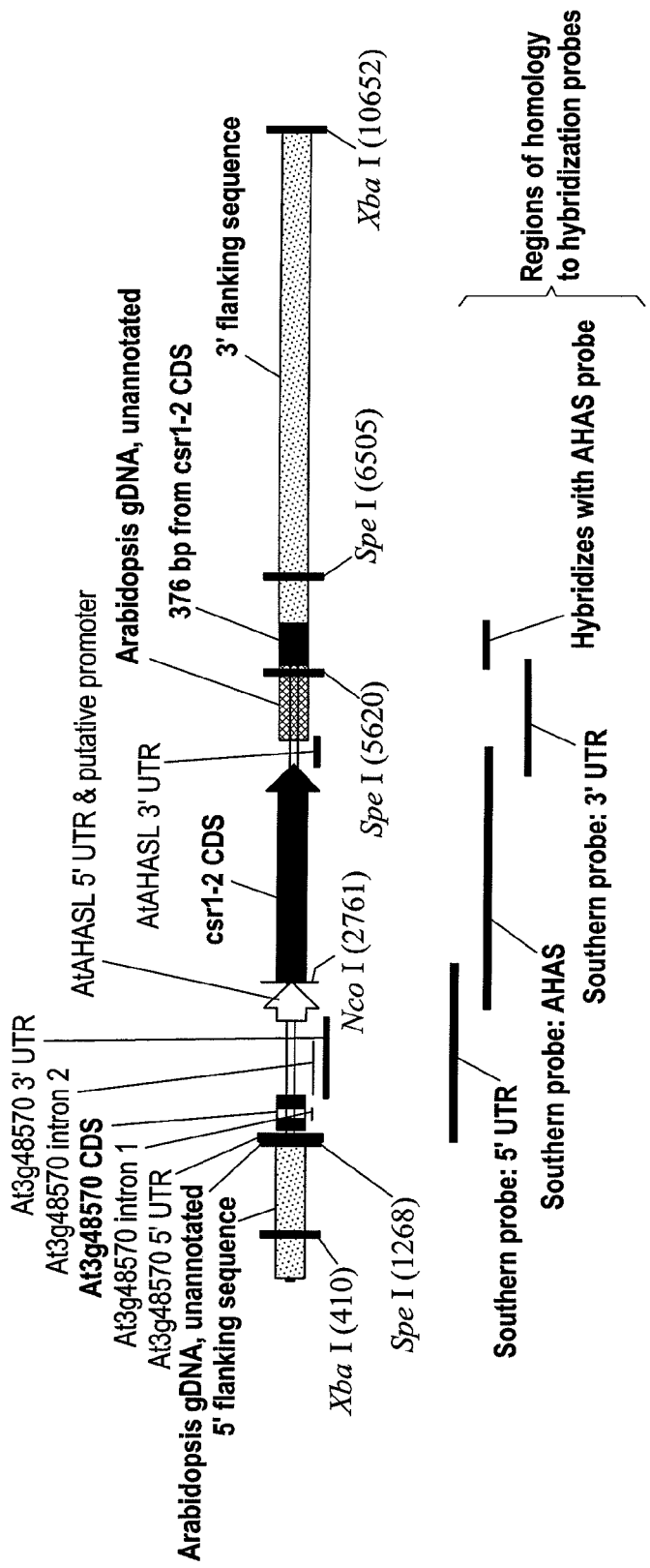
FIG. 6D provides a schematic representation of hybridization regions on the event 127 sequence of the respective probes.

In order to determine the stability of the insert in event 127, DNA samples from four different generations, T4, F4, F8 and F9, (FIG. 2) were subjected to Southern blot analysis. Genomic DNA samples were digested with NcoI and SpeI and probed with either the At AHASL 5' UTR, At AHASL coding sequence or At AHASL 3' UTR probes spanning the entire DNA fragment used for transformation (FIG. 1B). The combination of these restriction enzymes and probes provides a unique fingerprint for the DNA insert in event 127 (FIG. 4). Non-transgenic Conquista genomic DNA was used as a negative control and Conquista spiked with one- and two-genome copy equivalents of pAC321 was used as a positive control (FIG. 6). Multiple bands from event 127 T4 generation DNA digested with either NcoI or SpeI were detected with all three probes, indicating that the T4 generation contains multiple copies of the csr1-2 cassette. However, DNA from the F4, F8 and F9 generations all showed the same Southern pattern (FIG. 6) previously observed in the insert and copy number analyses (FIG. 4). This result indicates that the multiple copies of the insert in the T4 generation segregated in the progeny of the cross between T4 and Conquista and that only a single copy is retained in the segregant selected. Moreover, this single copy is stably inherited in subsequent generations.

D: Genomic Sequence Flanking the 5' and 3' Ends of the Insert DNA

Inverse-PCR was used to obtain the sequence of the soybean genomic DNA flanking the inserted csr1-2 cassette (Triglia et al., 1988). Genomic DNA (1 μg) from the event 127 F7 generation was digested with 15 units of XbaI, SpeI, HindIII, NcoI, EcoRI, BamHI or BglII in 20 μl reaction volumes for 3 h. The XbaI, HindIII, NcoI and EcoRI digests were incubated at 65° C. for 20 min to inactivate the enzymes while the BamHI and BglII digests were subjected to isopropanol precipitation. T4 DNA ligase (800 units, New England Biolabs) was directly added to each digestion reaction. Water was also added to bring the reaction volume to 200 μl. The reactions were incubated at 16° C. overnight and the circularized DNA was directly used as a template for inverse-PCR. The transgene flanking sequences were amplified with the GeneAmp® XL PCR kit (Applied Biosystems; Foster City, Calif.). The 100 μl primary PCR contained 1× manufacturer-supplied PCR buffer, 200 μM of each dNTP, 25 ng of the circularized genomic DNA fragments, 1.2 mM magnesium acetate, 2 units of rTth DNA polymerase XL, and 0.2 μM of each primary PCR primer. The 100 μl nested PCR contained the same components as the primary PCR except that 10 μl of a 1:50 dilution of the primary PCR was used as a template. The primary and nested PCRs were carried out on the GeneAmp PCR System 9700 (Applied Biosystems). Sequences of the primary and nested primers are provided in Table 4 below. After an initial one-minute denaturing step at 94° C., 30 cycles of 94° C. for 15 sec, 60° C. for 8 min and 72° C. for 2 min were performed followed by a final 10 min extension step at 72° C.

TABLE 8

Primers Used for Obtaining Flanking DNA Sequence Data

| Purpose | Direction | Primer Sequence | Position (FIG. 8) | SEQ ID NO: |
|---------|-----------|-----------------|-------------------|------------|
| 5' flank | Forward 1° PCR | GCAGCTTGTATCCATTCTCTTAACC | 2450-2474 | 17 |
| NcoI | Reverse 1° PCR | TTGTTGATTGGGATGAAAACGA | 1657-1678 | 18 |
| digest | Forward 2° PCR | Same as Forward 1° PCR primer (NcoI digest IPCR) | | 17 |
|  | Reverse 2° PCR | ACGAAGAATCCAACGAATCCC | 1631-1651 | 19 |
| 3' flank | Forward 1° PCR | AAGGAAATCCAGAAGCACTAATCA | 5517-5540 | 20 |
| XbaI | Reverse 1° PCR | TAATGCGAGATCAATTACCTC | 1718-1738 | 21 |
| digest | Forward 2° PCR | Same as Forward 1° PCR primer (XbaI digest IPCR) | | 20 |
|  | Reverse 2° PCR | CAATTACCTCGTAAAGAAAGTACTA | 1703-1727 | 22 |

After the PCR reactions were complete, the products were purified with Zymo DNA Clean & COncentrator™-5 (Zymo Research; Orange, Calif.). PCR products were either directly sequenced or sequenced after cloning. When the PCR products or cloned fragments were longer than 1 kb, primer walking was employed to obtain full-length sequence. Both DNA strands were sequenced to obtain a sequence quality of greater than Phred 40 at each base. Sequencing was performed with the BigDye™ Terminator v3.1 Ready Reaction Cycle Sequencing Kit and ABI 3730 DNA Analyzer from Applied Biosystems.

The 3' flanking PCR product amplified from the XbaI digest was about 6 kb and the amplification was too weak to obtain enough DNA for direct sequencing. Therefore, the PCR product was digested with SpeI and the resulting restriction fragments, one of about 800 bp and the other of about 5.2 kb, were treated with DNA Polymerase I, Large (Klenow) Fragment (New England Biolabs) to generate blunt ends and cloned into the pCR®-Blunt II-TOPO cloning vector (Zero Blunt® TOPO® PCR Cloning Kit; Invitrogen). Ten clones of each fragment were verified by restriction digestion and were sequenced by primer walking. The junction of the restriction fragments was confirmed by PCR amplification and sequencing across the junction.

A 3 kb DNA fragment was amplified by inverse PCR from the intramolecularly circularized NcoI digest of event 127 F7 generation genomic DNA. Sequencing of both ends of the fragment indicated that it was specifically amplified from the 5' side of the transgene insert. The fragment was further sequenced to obtain 1.3 kb of the 5' soybean flanking genomic sequence. A 6 kb DNA fragment was amplified by inverse PCR from the XbaI digest of event 127 F7 generation genomic DNA and was entirely sequenced after subcloning. The obtained sequence indicates that it flanks the insert on the 3' side. PCR analysis of non-transgenic variety Conquista DNA using primers from the 5' and 3' flanking regions was conducted to confirm that the flanking sequence was native to the plant genome (data not shown).

The entire Soybean event 127 transgene insert sequence with 5' and 3' flanking sequence is displayed in FIG. 8 (SEQ ID NO:1). BLAST analysis of the 5' flanking sequence queried against available public DNA databases (all GenBank+ EMBL+DDBJ+PDB sequences) and BASF Plant Science proprietary DNA databases revealed a region of sequence identity with a proprietary soybean expressed sequence tag (EST), confirming that the origin of the identified flanking sequence is native soybean DNA. The sequence was further analyzed for predicted open reading frames. Results indicated that there is a 315 bp ORF, from nucleotides 941 to 1255 of the flanking sequence, upstream of the 5' end of the insertion. Alignment of the 5' flanking sequence with the transformation sequence revealed that the integration point is at nucleotide 1312 (FIG. 8; SEQ ID NO:1), which is 60 bp downstream from the stop codon of the predicted ORF.

Analysis of the 3' flanking sequence showed that, before the 3' integration point, there is a 376 bp segment of sequence which differs from a portion of the csr1-2 coding sequence (nucleotides 3768-4143 of FIG. 8; SEQ ID NO:1) by only a single nucleotide. The insertion of this 376 bp sequence at the 3' flanking sequence junction created an ORF of 501 bp that extends from the transgene insert into the 3' flanking sequence. The potential transcription of this ORF was investigated by RT-PCR. BLAST analysis of the 3' flanking sequence queried against available public DNA databases (all GenBank+EMBL+DDBJ+PDB sequences) and BASF Plant Science proprietary DNA databases revealed a region of sequence similarity in the proximal 3' flanking sequence to a soybean catalase gene (accession No. Z12021). However, the integration point is about 500 bp upstream of the potential gene homolog and the putative coding sequence is about 2.4 kb downstream of the integration point. Therefore even if the possible catalase homolog is an active gene, it is unlikely to be affected by the insertion. In addition, a region of the distal 3' flanking sequence shared sequence identity with a proprietary soybean EST.

Studies were conducted to PCR-amplify the Event 127 integration site from the genome of non-transgenic Conquista. PCR primer sets A and B that include one primer in the 5' flanking region and a second primer in the 3' flanking region to amplify the insertion site did not produce an amplified DNA product using genomic DNA from the non-transgenic variety Conquista as a template. PCR primer set C with primers specific to the 3' flanking sequence did not produce an amplification product from non-transgenic variety Conquista DNA while the expected amplicon was produced with genomic DNA from event 127 (data not shown). This demonstrates that the DNA fragment amplified by primer set C is present in event 127 but does not exist in the same context in the genome of Conquista, which suggests that a DNA rearrangement at the insertion site has occurred in event 127. This is consistent with the identification of a 376 bp segment of duplicated sequence from the csr1-2 coding region near the junction of the inserted DNA and the genomic soybean DNA.

E. Complete Sequence of Insert DNA

Figure 7:
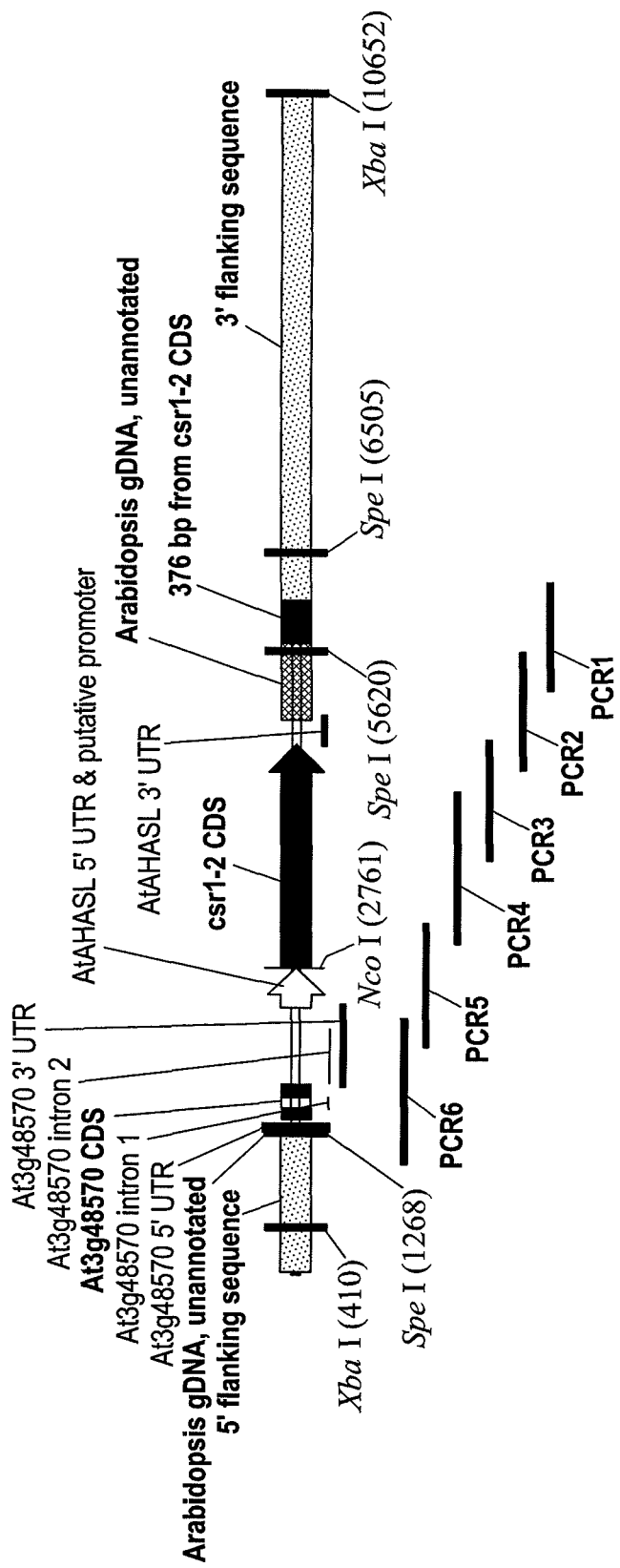
FIG. 7 provides a diagram of an insert and flanking sequence in one example of a soybean event 127 plant. Six amplicons used for sequencing as described in Example 3 are also indicated.

Six PCR-generated amplicons were designed to span the entire insert as well as the junctions with the adjacent soybean genomic sequences (FIG. 7). The complete sequence of the inserted DNA was obtained by PCR amplification of these six overlapping fragments followed by DNA sequence analysis. Sequences of the primers used for PCR amplification are provided in Table 5. PCR amplicons containing sequence discrepancies relative to the sequence of the transformation fragment were re-amplified with rTth DNA polymerase XL. PCR products were purified with the Zymo DNA Clean & Concentrator™-5 and were sequenced on both strands to a quality level of Phred 40 bp direct sequencing and primer walking. DNA sequencing was performed as described above.

TABLE 9

Primers Used for Event 127 DNA Insert Amplification

| Purpose | Direction | Primer Sequence | Position (FIG. 8) | SEQ ID NO: |
|---|---|---|---|---|
| PCR1 | Forward | GCTTGATATGCCTTTTGGTTC | 5265-5285 | 23 |
|  | Reverse | TTGTCTTCCCTCATTGGAC | 6150-6168 | 24 |
| PCR2 | Forward | GACGAGATATTCCCGAAC | 4544-4561 | 25 |
|  | Reverse | GTCTGATTAGTGCTTCTGG | 5525-5543 | 26 |
| PCR3 | Forward | CCCTGTTGCGAGTACGTTGA | 3739-3758 | 27 |
|  | Reverse | CTTCCGTTATGACATCGTTG | 4732-4751 | 28 |
| PCR4 | Forward | AACCACTCCCTCTCCAAC | 2980-2997 | 29 |
|  | Reverse | CTGATGATAGCCACTGCC | 4266-4283 | 30 |
| PCR5 | Forward | TTCGTTCGCTCTGGTGTC | 2062-2079 | 31 |
|  | Reverse | ACGGTTTCTACGCCTTG | 3089-3105 | 32 |
| PCR6 | Forward | GAAAATAGGAAGTTTAGGCTTG | 1000-1021 | 33 |
|  | Reverse | GGGCTGATAATGTCGTTTG | 2229-2247 | 34 |

Although Southern blot analysis suggested that the transgene insert contained the complete csr1-2 expression cassette, cloning and sequencing of the insert was performed to confirm insert integrity. The complete sequence of the inserted DNA was obtained by PCR amplification of six overlapping amplicons with Taq DNA polymerase (FIG. 7). The complete Soybean event 127 insert sequence is 4758 bp in length and other than the insertion of the 376 bp fragment from csr1-2 at the 3' integration point, the sequence is identical to the sequence of the transformation fragment except for three point mutations (FIG. 8; SEQ ID NO:1). One of the point mutations is a G to A mutation in the AHASL coding sequence, which results in an amino acid change from $R_{272}$ to $K_{272}$. This is a conservative amino acid substitution and has no impact on the herbicide tolerance or enzymatic properties of the At AHAS protein. The other two mutations include a G to A mutation and a G to C mutation, both of which are located downstream of the 3'UTR of the csr1-2 gene and so are genetically silent.

Experiments were carried out to determine at what point in the production and breeding development of Soybean Event 127 the G to A mutation in the AHASL coding sequence occurred. Initially, the PCR4 reaction (FIG. 7) used in sequencing of the insert was set up with genomic DNA from both event 127 T4 and F8 generations as template and PCR products were sequenced. Sequence from the event 127 T4 generation did not differ from the expected (pAC321) sequence. Considering that the T4 generation contains multiple copies of the insert and the PCR4 product is likely a mix of sequences from various copies of the insert, an event 127 locus-specific PCR amplicon of 2.5 kb was designed with a forward primer (5'-GCCCTCCTTATTTATCCCCTTA-3'; SEQ ID NO:35) in the 5' flanking sequence and a reverse primer (5'-ACAAACCTACCCAATTCATCGC-3'; SEQ ID NO:36) in the csr1-2 coding sequence. PCR products were sequenced directly. Sequence comparison revealed that the G to A mutation also exists in the event 127 T4 generation, indicating that the mutation occurred sometime before the T4 generation (data not shown) and has been maintained for the subsequent eight generations.

The initial transformation sequence contains a 2.5 kb segment which was originally annotated as the AHASL promoter and 5' UTR. Recent sequence analysis has revealed that this sequence segment also contains a previously unannotated *Arabidopsis* gene encoding the gamma subunit of SEC61, a multimeric transport protein. The event 127 insert sequence contains the majority of the AtSec61γ subunit gene including the complete coding sequence. The AtSec61γ 5' UTR, as annotated by The *Arabidopsis* Information Resource, begins 18 nucleotides downstream from the 5' transgene integration site. As such, it is unlikely that the insert contains the complete native promoter for the AtSec61γ gene.

Figure 9:
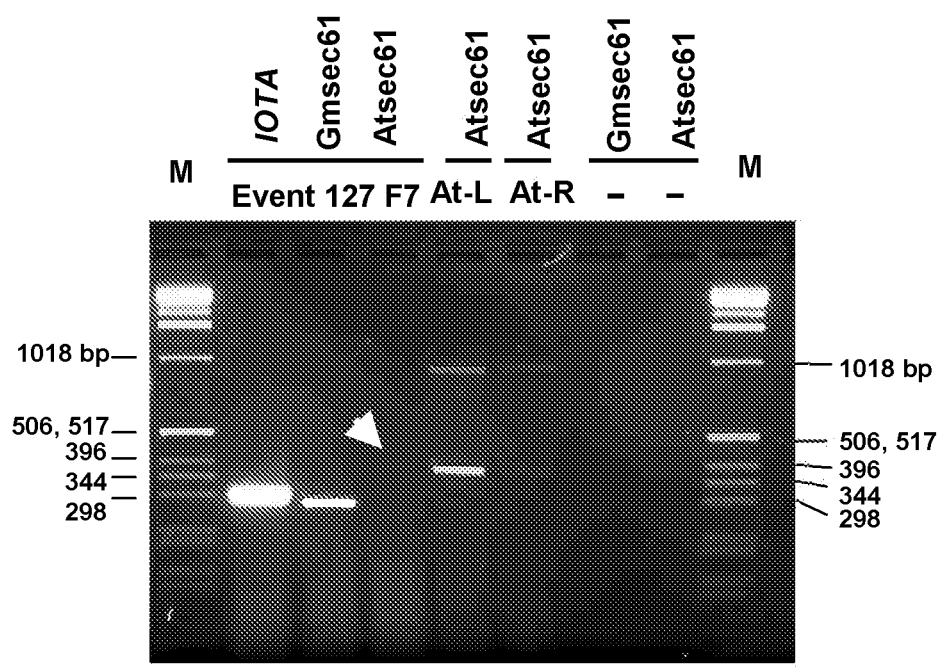
FIG. 9 provides gel electrophoresis results of RT-PCR analysis of the transcription of an AtSec 61γ subunit in one example of a soybean event 127 plant as described in Example 3.

The possible transcription of the *Arabidopsis* AtSEC61γ subunit gene found in the insert in Soybean event 127 was evaluated using RT-PCR. RT-PCR was carried out using DNase-treated total RNA extracted from the F7 generation of event 127 as a template. Primers specific to two endogenous soybean genes, Iota and GmSec61γ, were used as positive controls to confirm the quality of template RNA. Total RNA from *Arabidopsis* leaf and root tissues without DNase treatment was also used as a positive control. Results showed that both endogenous soybean positive controls, Iota and GmSec61γ were strongly transcribed in young soybean leaf tissue while the AtSec61γ subunit gene in the event 127 F7 generation was only weakly transcribed. The arrow in FIG. 9 indicates the faint RT-PCR product corresponding to the AtSec61γ subunit amplified from event 127. The amplified 393 bp AtSec61γ subunit DNA band from the F7 generation of event 127 is the same size as that amplified from *Arabidopsis* leaves and roots (FIG. 9). The same pair of primers also amplified a band of the expected size, 965 bp, from contaminating genomic DNA in *Arabidopsis* leaf and root samples. To confirm the identity of the event 127 RT-PCR product, it was sequenced and compared with the predicted mRNA sequence of the AtSec61γ subunit (data not presented). Both sequences matched, indicating that the AtSec61γ subunit is weakly transcribed in leaves of event 127.

Figure 10:
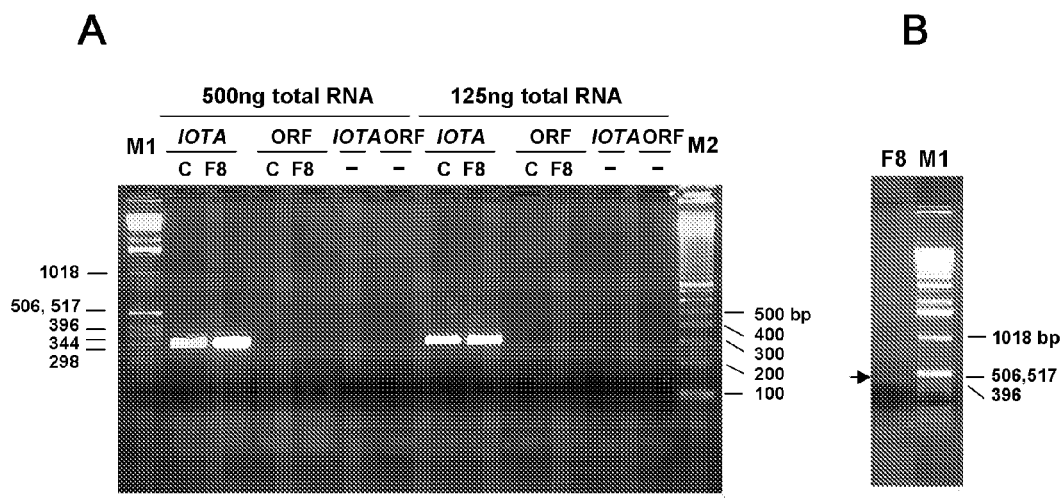
FIG. 10 provides gel electrophoresis results of RT-PCR analysis of the transcription of 501 bp open reading frame (ORF) created by the insertion of a 376 bp duplication of the csr1-2 coding sequence at the 3' flanking junction in one example of a soybean event 127 plant as described in Example 3.

The insertion of a 376 bp portion of the csr1-2 coding sequence near the 3' flanking sequence junction (FIG. 7) created a 501 bp ORF. The possible transcription of this ORF was investigated by RT-PCR analysis. RT-PCR was carried out with two different amounts of RNA template, 500 ng and 125 ng. Event 127 F8 generation genomic DNA was also used in a positive control reaction with ORF-specific primers. Primers specific for the soybean Iota gene were used in positive control reactions to confirm the quality of the template RNA. The ORF-specific primers amplify a 435 bp fragment from event 127 genomic DNA. However, no detectable RT-PCR product was observed using total RNA from young leaf tissue as a template, suggesting that the ORF is not expressed in Event 127 (FIG. 10).

F. PCR Assay for Qualitative Event-Specific Detection

Event-specific PCR was developed using the information obtained from both the DNA flanking sequence and the insert sequence. Four pairs of primers were designed with one primer of each pair in the 5' soybean flanking sequence and the other in the csr1-2 cassette. The sequences of the primers for use in event-specific PCR are provided below in Table 10.

TABLE 10

Primers Used for Event-Specific PCR

| Purpose | Direction | Primer Sequence | Position (Fig. 8) | SEQ ID NO: |
|---|---|---|---|---|
| Event PCR1 | Forward | GAAAATAGGAAGTTTAGGCTTG | 1000-1021 | 37 |
| | Reverse | CACTGCTCTTAGCGAAATCTC | 1426-1446 | 38 |
| Event PCR2 | Forward | GCCCTCCTTATTTATCCCCTTA | 1210-1231 | 39 |
| | Reverse | GCCGTACGCACAGCTACTTTC | 1592-1612 | 40 |
| Event PCR3 | Forward | ATAGGAAAGCGCAAACTG | 1128-1145 | 41 |
| | Reverse | CGAACACTGCTCTTAGCGAAAT | 1429-1450 | 42 |
| Event PCR4 | Forward | GCCCTCCTTATTTATCCCCTTA | 1210-1231 | 43 |
| | Reverse | AGGATCGATTGCGGAATCA | 1403-1421 | 44 |

The primers were designed to amplify PCR products between about 200 to about 400 bp in length. Genomic DNA from both Event 127 and the non-transgenic variety Conquista was used as template. PCRs were performed in 25 μl total volume with 25 ng of the template DNA, 200 μM of each dNTP, 0.4 μM of each primer and 1 unit Taq DNA polymerase per reaction. After an initial 4 min denaturation at 94° C., 30 cycles of 94° C. for 30 sec, 60° C. (Event PCR1 and 3) or 66° C. (Event PCR2 and 4) for 30 sec, and 72° C. for 45 sec were performed, followed by a final 10 min extension at 72° C. Four plants each of Soybean event 127 and the non-transgenic variety Conquista from six different planting locations were analyzed by qualitative PCR using the "Event PCR3" primer set.

Figure 11:
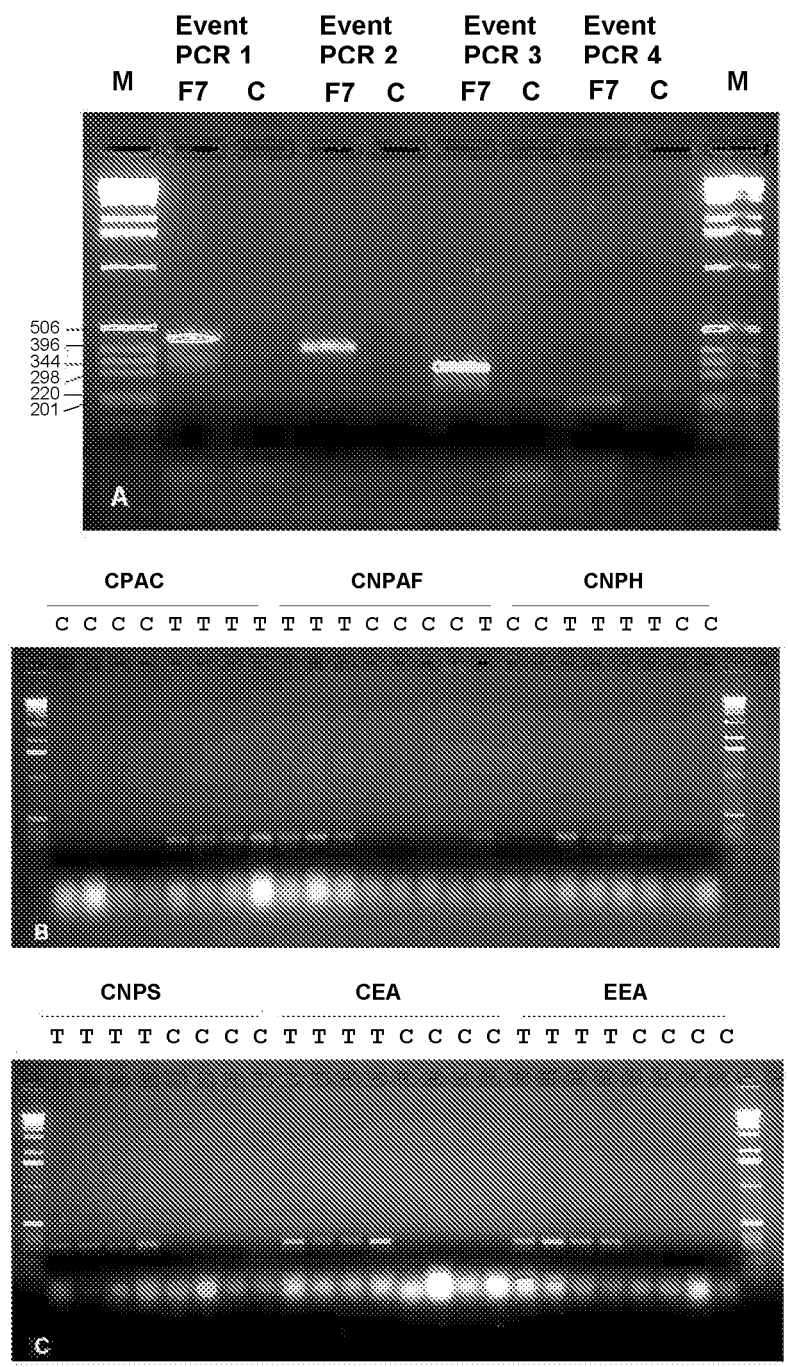
FIG. 11 provides gel electrophoresis results of examples of event 127-specific PCR detection methods as described in Example 3.

All four PCRs generated products of the expected size specifically from Soybean event 127 (FIG. 11A), suggesting that any of the four primer sets may be used for detection of an event 127 nucleic acid molecule in a sample. Event-specific PCR product 3 was further validated with samples of event 127 soybean plants and non-transgenic variety Conquista collected from six different planting locations. Results showed that PCR product 3 was amplified specifically in all 24 samples of event 127 soybean but not in non-transgenic control variety Conquista (FIGS. 11B and C).

G. PCR Assay for Quantitative Event-Specific Detection

Event-specific quantitative PCR has been designed to detect and accurately and precisely quantify event 127 nucleic acid in a mixed batch of seeds if event 127 nucleic acid soybeans are present in the sample between 0.08% and 5% of the total amount of nucleic acid present in the sample. In this method, two pairs of primers along with intervening probes are used. The sequences of the primers for use in event-specific PCR are provided below in Table 11.

mixture of genomic DNA from event 127 soybean (10%) and Conquista (non-GM)(90%) is diluted to 20 ng/μl. For the standard curve, this was then diluted with 10 ng/μl salmon sperm DNA to 20, 4, and 0.8 ng soybean DNA (volume in reaction is 5 μl). PCR reactions were performed in 25 μl volumes in 96-well plates, with all standard components (TaqMan Universal PCR master mix with Uracil-N-glycosylase (AmpErase®UNG, ABI)). For event PCR, primers are added at a concentration of 400 nM and probes at 100 nM. For endogenous PCR, primers are added at a concentration of 150 nM and probes at 50 nM. Assays are run on an Applied Biosystems 7500 Fast Real-Time PCR System. After an initial single cycle of 2 min at 50° C. and 10 min at 95° C., 45 cycles of 95° C. for 15 sec and 60° C. for 60 sec are performed. Three samples each of event 127 soybean and the non-transgenic variety Conquista and the mixtures are analyzed by quantitative PCR.

H. Analysis of Duplication and SEC61γ Gene

RT-PCR was conducted to determine if either the 376 bp duplication of a portion of the csr1-2 coding sequence or the AtSec61γ gene present in soybean event 127 was transcribed. Total RNA was used as template for RT-PCR using the Qiagen OneStep RT-PCR Kit (Qiagen). For RT-PCR analysis of the AtSec61γ coding sequence, Arabidopsis total RNA samples from leaves and roots were also used as positive controls. The Arabidopsis total RNA samples were prepared with TRIzol reagent (Invitrogen) without DNase treatment.

TABLE 11

Primers Used for Q-PCR Analysis

| Purpose | Direction | Primer Sequence | Position (FIG. 8) | SEQ ID NO: |
|---|---|---|---|---|
| Event PCR | Forward | AACAGAAGTTTCCGTTGAGCTTTAAGAC | 6030-6057 | 45 |
|  | Probe | TTTGGGGAAGCTGTCCCATGCCC | 6059-6081 | 46 |
|  | Reverse | CATTCGTAGCTCGGATCGTGTAC | 6095-6117 | 47 |
| Endogenous PCR | Forward | CCAGCTTCGCCGCTTCCTTC | NA | 48 |
|  | Probe | CTTCACCTTCTATGCCCCTGACAC | NA | 49 |
|  | Reverse | GAAGGCAAGCCCATCTGCAAGCC | NA | 50 |

In this Taq-Man based assay, the level of event-specific PCR product is compared with that of an endogenous control during each cycle in two different reaction mixes.

The assay format makes use of standard curves for each of the two PCR systems; each standard curve is comprised of four standard points each derived from triplicate measurements. The standards are produced by preparing solutions of 20 ng/μl of total genomic DNA containing 10% event 127 soybean DNA (standard 1) and subsequent serial 1:5 dilutions with dilution buffer (standards 2 to 4). Three no-template controls (NTC) per system are run to verify the purity of reagents. Each sample (unknown) is analyzed at 100 ng genomic DNA per reaction.

Event and endogenous PCR probes are conjugated to FAM (Excitation 495 nm; Emission, 520 nm). Primers are designed to produce short amplicons of less than 100 bp in length. A The RT-PCR reactions contained 1× Qiagen OneStep RT-PCR Buffer, 400 μM of each dNTP, 0.6 μM of each primer, 2 μl of Qiagen OneStep RT-PCR Enzyme mix, and 500 ng or 125 ng of total RNA in a total volume of 50 μl. The RT-PCR was conducted using the GeneAmp PCR System 9700. Following a 30 min reverse transcription step at 50° C., PCR amplification was carried out under the following conditions: one 15 min denaturation step at 95° C.; 30 cycles at 94° C. for 30 sec, 64° C. for 30 sec, and 72° C. for one min; and one ten-min extension at 72° C. The sequences of the primers used for the RT-PCR analysis are provided in Table 12.

The endogenous soybean Sec61γ subunit and Iota genes were used as positive controls. The soybean Iota subunit gene is expressed constitutively and ubiquitously in soybean (Yamamoto and Knap, 2001).

TABLE 12

Primers Used for RT-PCR Analysis

| Purpose | Direction | Primer Sequence | Position (FIG. 8) | SEQ ID NO: |
|---|---|---|---|---|
| RT-PCR AtSec61 | Forward | ACGAACCTGCTGAAACCCTAAT | 1338-1359 | 51 |
|  | Reverse | TAAGAATGGAGAATTTGGCTACA | 2280-2302 | 52 |

TABLE 12-continued

Primers Used for RT-PCR Analysis

| Purpose | Direction | Primer Sequence | Position (FIG. 8) | SEQ ID NO: |
|---------|-----------|-----------------|-------------------|------------|
| RT-PCR Iota | Forward | TGAAGCAGCAGCTGAGTTTCGC | N/A* | 53 |
|  | Reverse | GGCAGTCTGAACCGTCTCCTC | N/A | 54 |
| RT-PCR GmSec61 | Forward | GCTTGGGAGACAGAGAAAGAGA | N/A* | 55 |
|  | Reverse | CCTTTTGCTTGACAACCTGAAT | N/A | 56 |
| RT-PCR ORF501 | Forward | TTGGAATGCATGGGACTGT | 3807-3825, 5733-5751 | 57 |
|  | Reverse | TGTCTTCCCTCATTGGACTG | 6148-6167 | 58 |

*N/A - not applicable. This is a positive control; primer set is expected to amplify cDNA derived from an endogenous soybean transcript unrelated to the Event 127 insert.

I. PCR Analysis of the Integration Site

Three PCR reactions were carried out to characterize the insertion site in the non-transgenic soybean variety Conquista. The PCR primers used in this study were derived from the DNA sequence that was determined for the 5' and 3' genomic regions flanking the novel expression cassette in the genome of Event 127.

PCR primers for PCRA (see table 13 below) were designed such that the forward primer would bind in the 5' flanking sequence and the reverse primer would bind in the 3' flanking sequence immediately after the 3' integration point. Primers for PCRB were designed so that the forward primer would bind in the 5' flanking sequence while the reverse primer would bind close to the distal end of the 3' flanking sequence. Both primers for PCRC were designed to bind within the 3' flanking sequence.

TABLE 13

Primers Used for Analysis of Integration Site

| Purpose | Direction | Primer Sequence | Position (FIG. 8) | SEQ ID NO: |
|---------|-----------|-----------------|-------------------|------------|
| PCRA | Forward | CCACAATGTGCCAATTAAGT | 936-955 | 59 |
|  | Reverse | GCGTGTTTCTTTAGCATCA | 6,319-6,337 | 60 |
| PCRB | Forward | CTCCTTCGCCGTTTAGTGTA | 1,109-1,128 | 61 |
|  | Reverse | GTTTCGCGTTTAGGGTTCC | 10,098-10,116 | 62 |
| PCRC | Forward | ATAAGCCAATTTGGGTCTGCC | 8,312-8,332 | 63 |
|  | Reverse | GTTTCGCGTTTAGGGTTCC | 10,098-10,116 | 64 |

PCRA and PCRC were carried out with Qiagen Taq DNA polymerase and PCR2 with GeneAmp® XL PCR kit. Twenty-five ng of either Event 127 or Conquista DNA was used in all PCR amplifications. For the PCR with Qiagen Taq DNA polymerase, the reaction contained 1× Qiagen PCR buffer, 200 µM of each dNTP, 0.4 µM of each primer and 1 unit of Taq DNA polymerase in 25 µl total volume. After an initial 4 minute denaturation step at 94° C., 30 cycles at 94° C. for 30 sec, 66° C. for 45 sec and 72° C. for 2 min were performed followed by a final 10 minute extension step at 72° C.

For PCR with the GeneAmp® XL PCR kit, the reaction contained the same components as used in the cloning of flanking sequence except for the template DNA. After an initial 1 min denaturation step at 94° C., 30 cycles at 94° C. for 1 min and 66° C. for 10 min were performed followed by a final 10 minute extension at 72° C.

J. Bioinformatics analysis.

DNA sequence assembly was carried out with Staden Pregap4 and Gap4 (Staden, 1996). Alignment of the cloned and expected insert sequences was conducted with LI-COR AlignIR software (Licor Biotechnology; Lincoln, Nebr.). The flanking sequences were queried against available public DNA databases (all GenBank+EMBL+DDBJ+PDB sequences) and BASF Plant Science proprietary DNA databases via BLAST analysis (Altschul et al., 1997). Open reading frames of 30 codons or more were identified with the ORF analysis function of Vector NTI v9.0 (Invitrogen).

Based on the results of these experiments, soybean event 127 contains a single copy insert of 4758 bp that includes the complete expression cassette of csr1-2, as well as the 5' UTR, the entire coding sequence, and the 3' UTR of the AtSec61γ subunit gene. A 376 bp repeat of coding sequence from the csr1-2 gene is also integrated at the 3' junction with the flanking sequence. No vector backbone sequence was found to be integrated in the soybean genome. The insert was stably inherited across eight breeding generations, demonstrating that the insert is stably integrated in the soybean genome. There are three point mutations in the csr1-2 expression cassette: one conservative mutation in the AHASL coding sequence that has no impact on the herbicide tolerance or enzymatic properties of the mutant AHASL protein, and two mutations downstream of the 3' UTR. It appears that a rearrangement of the soybean genomic DNA occurred in DNA flanking the 3' end of the insert, and this most likely occurred during the DNA integration process. The insert contains the coding sequence of the AtSec61γ subunit gene, which was included in the DNA fragment used for transformation. This gene is only weakly transcribed. A 376 bp fragment of the csr1-2 coding sequence created a new ORF of 501 bp. RT-PCR experiments indicated no detectable transcription of this ORF.

Example 4

Weed Control

A. Example 4A

Postemergent Application

Three field experiments were established at three different locations in the central region of Brazil: Agricultural Research Station (ARS) in Santo Antonio de Posse, SP, Embrapa Rice and Beans (CNPAF) in Santo Antonio de Goiás, GO and Embrapa-Epamig (CTTP) in Uberaba, MG. The weed infestation in each site was presented in the Table 13.

TABLE 13

Weed infestation at each site when the herbicides were applied - at early postemergence

| Locations | Weeds (infestation - pl/sqm) |
|---|---|
| ARS | CYPRO (25), RCHBR (12) and IPOGR (14) |
| CNPAF | COMBE (18) and BOILF (22) |
| CTTP | EPHHL (21) and SIDRH (17) |

CYPRO = *Cyperus rotundus*;
BOILF = *Spermacoce latifolia*;
COMBE = *Commelina benghalensis*;
EPHHL = *Euphorbia heterophylla*;
SIDRH = *Sida rombifolia*;
RCHBR = *Richardia brasiliensis*;
IPOGR = *Ipomoea grandifolia*.

All the procedures from planting to harvest were the same for all three locations. The herbicides were applied at early post-emergence, when the weeds were with 2 to 4 leaves and soybean crop with the first trifoliate leaf completely opened. A completely randomized block design with three replications was used. The main treatments are presented in Table 15.

TABLE 15

Main treatments applied at early post-emergence of the weeds:

| Treatments | Rate (gai/ha) | Formulation |
|---|---|---|
| 1. Imazapyr | 72 | 480 g/l - AS |
| 2. Imazapyr + imazapic (Kifix) | 70 | 525 + 175 g/kg - WG |
| 3. Glyphosate | 540 | 360 g/l - AS |

The imidazolinone herbicides were applied over imidazolinone tolerant soybean (derived from event 127) and glyphosate was applied over Roundup Ready soybean (Valiosa RR), planted side by side at each location. The imidazolinone herbicides (imazapyr and Kifix) were applied with a nonionic adjuvant—Dash—at 0.25% v/v. A CO2 backpack sprayer with 80015 low pressure nozzles delivering 170 l/ha at 190 kpa was used for all herbicide applications. All soybean seed were planted 5 cm deep at population of 380,000 seeds/ha in 50 cm row spacing.

Crop injury was assessed 15 and 30 days after application (DAA) based on a 0 to 100 scale where 0 is no injury and 100 is crop death. Herbicide efficacy was assessed at 15, 30 and 60 DAA based on a 0 to 100 scale, where 0 is no control and 100 is total control.

Table 16 below shows the efficiency of these key treatments over the weeds presented in the areas at the moment of the herbicide application. According to these results, imazapyr and an imazapyr+imazapic combination had similar efficacy. At 30 DAA both products were very efficient over these seven important Brazilian weeds: CYPRO (87%), COMBE (87-90%), EPHHL (85-87%), IPOGR (90-91%), BOILF (82-83%), SIDRH (86-87%) and RCHBR (83%). At 60 DAA, imidazolinone herbicides were superior to glyphosate over CYPRO, COMBE, RCHBR and IPOGR when applied postemergent.

TABLE 16

Efficacy of imazapyr, an imazapyr + imazapic combination, and glyphosate applied at post emergence on soybeans (Event 127 and RR).

| | | Weeds | | | | | | | | |
|---|---|---|---|---|---|---|---|---|---|---|
| | gai/ha - | CYPRO | | | BOILF | | | COMBE | | |
| Products | DAT | 15 | 30 | 60 | 15 | 30 | 60 | 15 | 30 | 60 |
| Imazapyr | 72 | 95 | 87 | 81 | 88 | 83 | 75 | 93 | 87 | 80 |
| Imazapyr + imazapic | 70 | 97 | 88 | 82 | 88 | 82 | 73 | 91 | 90 | 83 |
| Glyphosate | 540 | 67 | 43 | 35 | 82 | 75 | 68 | 70 | 61 | 50 |

| | | Weeds | | | | | | | | |
|---|---|---|---|---|---|---|---|---|---|---|
| | gai/ha - | EPHHL | | | SIDRH | | | RCHBR | | IPOGR |
| Products | DAT | 15 | 30 | 60 | 15 | 30 | 60 | 15 | 30 | 60 | 15 | 30 | 60 |
| Imazapyr | 72 | 92 | 85 | 83 | 94 | 87 | 81 | 86 | 83 | 77 | 96 | 91 | 85 |
| Imazapyr + imazapic | 70 | 98 | 87 | 83 | 93 | 86 | 82 | 92 | 83 | 75 | 97 | 90 | 84 |
| Glyphosate | 540 | 85 | 77 | 72 | 82 | 77 | 70 | 78 | 57 | 43 | 90 | 87 | 73 |

Example 4B

Burndown Applications

Three field experiments were established at three different locations in the central region of Brazil: Agricultural Research Station (ARS) in Santo Antonio de Posse, SP, Embrapa Rice and Beans (CNPAF) in Santo Antonio de Goias, GO and Embrapa-Epamig (CTTP) in Uberaba, MG. The weed infestation in each of these areas was presented in the Table 17.

TABLE 17

Weed infestation at each site when the herbicides were applied - at burn down:

| Locations | Weeds (infestation - pl/sqm) |
|---|---|
| ARS | CYPRO (23), EPHHL (15) and GASPA (32) |
| CNPAF | DIGHO (24), COMBE (15) and IPOGR (11) |
| CTTP | BRAPL (41) and BIDPI (25) |

BRAPL = *Brachiaria plantaginea*;
DIGHO = *Digitaria horizontalis*;
CYPRO = *Cyperus rotundus*;
COMBE = *Commelina benghalensis*;
EPHHL = *Euphorbia heterophylla*;
IPOGR = *Ipomoea grandifolia*;
GASPA = *Galinsoga parviflora*;
BIDPI = *Bidens pilosa*.

All the procedures from planting to harvest were the same for all three locations. The herbicides were applied at burn down five days before the soybean planting.

A completely randomized block design with three replications was used. The main treatments were listed in the Table 18.

TABLE 18

Main treatments applied at burn down - 5 days before planting:

| Treatments | Rate (g.a.i./ha) | Formulation |
|---|---|---|
| 1. Glyphosate | 1080 | 360 g/l - AS |
| 2. Imazapic | 70 | 700 g/kg - WG |
| 3. Imazapic + imazapyr | 70 | 525 + 175 g/kg - WG |

Imidazolinone-tolerant soybean derived from event 127 was planted 5 cm deep at population of 380,000 seeds/ha in 50 cm row spacing. The imidazolinones herbicides were applied with a nonionic adjuvant, Dash, at 0.25% v/v. A $CO^2$ backpack sprayer with 80015 low pressure nozzles delivering 170 l/ha at 190 kpa was used for all herbicide applications (Table 18).

Crop injury was assessed 15 and 30 days after planting (DAP) based on a 0 to 100 scale where 0 is no injury and 100 is crop death. Herbicide efficacy was assessed at 15, 30 and 60 DAP based on a 0 to 100 scale, where 0 is no control and 100 is total control.

The Table 19 shows the efficiency of these key treatments over the weeds presented in the areas at burn down application. The results at 30 and 60 DAA showed the residual effect of the imidazolinone herbicides compared to glyphosate. At 30 DAA, an imazapyr+imazapic combination was a little better than imazapic, but both were efficient on BRAPL (85%), DIGHO (95%), CYPRO (88%), COMBE (75-94%), EPHHL (95%), IPOGR (75%), GASPA (84-95%) and BIDPI (79-93%). Glyphosate had no residual activity and it was not efficient over these 8 weeds at 30 and 60 DAA.

TABLE 19

Efficacy (%) of imazapic, an imazapyr + imazapic combination, and glyphosate applied at burn down over key Brazilian weeds

| | | Weeds | | | | | | | |
|---|---|---|---|---|---|---|---|---|---|
| | g ai/ha - | BRAPL | | DIGHO | | CYPRO | | COMBE | |
| Products | DAT | 30 | 60 | 30 | 60 | 30 | 60 | 30 | 60 |
| Glyphosate | 1080 | 53 | 25 | 60 | 41 | 60 | 53 | 38 | 22 |
| Imazapic | 70 | 85 | 79 | 95 | 86 | 88 | 76 | 75 | 64 |
| Imazapic + imazapyr | 70 | 87 | 82 | 98 | 87 | 95 | 87 | 94 | 87 |

| | | Weeds | | | | | | | |
|---|---|---|---|---|---|---|---|---|---|
| | gai/ha - | EPHHL | | IPOGR | | GASPA | | BIDPI | |
| Products | DAT | 30 | 60 | 30 | 60 | 30 | 60 | 30 | 60 |
| Glyphosate | 1080 | 15 | 7 | 23 | 15 | 19 | 12 | 25 | 21 |
| Imazapic | 70 | 98 | 86 | 75 | 73 | 84 | 78 | 79 | 73 |
| Imazapic + imazapyr | 70 | 95 | 82 | 91 | 83 | 95 | 81 | 93 | 82 |

Example 4C

Control of Glyphosate Tolerant Plants

Greenhouse studies were conducted to determine whether imidazolinone herbicides could be used in the control of undesired glyphosate tolerant weeds and crops growing in a cultivated area. Seeds of glyphosate resistant plants were planted in 4.5 inch pots using metro mix for postemergence application and North Carolina soil for Preemergence application with slow release fertilizers on the soil surface. Plants were maintained in a greenhouse with overhead watering.

Five individual plants of each of glyphosate resistant soybean, corn, and horseweed were subjected to spray treatments of glyphosate, imazapyr, or imazapic applied either postemergence or preemergence. Postemergence sprays were conducted at the 2-true leaf stage for corn and soybean and at the 9-true leaf stage for horseweed. Glyphosate was applied at a rate of 774 g ae/ha, while imazapyr and imazapic herbicides were applied at rates of 20 g ai/ha, 40 g ai/ha, 80 g ai/ha, 160 g ai/ha, and 240 g ai/ha. The percent overall injury rate was visually determined 14 days after treatment (DAT) and 25 days after treatment (DAT). Untreated control plants exhibited no visual injury in any of the studies. The results of the postemergence tests are summarized in Table 20 and the results of the pre-emergence study are summarized in Table 21. Results are provided as averages of the 5 individual plants.

TABLE 20

Injury rate from postemergence application
of glyphosate and imidazolinone herbicides

| | | Average Overall Injury (%) | | | | | | | | | |
|---|---|---|---|---|---|---|---|---|---|---|---|
| | | Gly | Imazapyr | | | | | Imazapic | | | |
| | DAT | 774 | 20 | 40 | 80 | 120 | 240 | 20 | 40 | 80 | 160 | 240 |
| Soybean | 14 | 1 | 75 | 96 | 97 | 98 | 99 | 35 | 61 | 71 | 87 | 96 |
| Corn | 14 | 1 | 96 | 98 | 99 | 100 | 100 | 83 | 87 | 93 | 99 | 99 |
| Horseweed | 14 | 34 | 70 | 79 | 90 | 96 | 97 | 56 | 59 | 80 | 92 | 94 |
| Horseweed | 25 | 16 | 44 | 73 | 97 | 99 | 99 | 27 | 28 | 69 | 77 | 88 |

TABLE 21

Injury rate from preemergence application of glyphosate and imidazolinone herbicides

| | | Average Overall Injury (%) | | | | | | | | | |
|---|---|---|---|---|---|---|---|---|---|---|---|
| | | Gly | Imazapyr | | | | | Imazapic | | | |
| | DAT | 774 | 20 | 40 | 80 | 120 | 240 | 20 | 40 | 80 | 160 | 240 |
| Soybean | 14 | 0 | 41 | 43 | 66 | 83 | 87 | 12 | 39 | 60 | 70 | 81 |
| Corn | 14 | 0 | 37 | 47 | 65 | 81 | 91 | 32 | 38 | 67 | 86 | 90 |
| Horseweed | 14 | N/D | N/D | N/D | N/D | N/D | N/D | N/D | N/D | N/D | N/D | N/D |
| Horseweed | 25 | 0 | 46 | 63 | 84 | 96 | 88 | 65 | 90 | 99 | 99 | 99 |

These results indicate that imidazolinone herbicides can be used to control glyphosate tolerant weeds and crops either pre- or postemergence. One advantage is the ability to use imidazolinone herbicides with event 127 plants to control resistant weeds and undesired plants that glyphosate is no longer effective to control.

Example 4D

Increased Soybean Production Using Soybean Event 127

Field trials were conducted to evaluate the agronomic, phenotypic, and phenologic characteristics of a transgenic soybean line with tolerance to imidazolinone herbicides (event 127) relative to a nontransgenic isogenic control (null) and to other nontransgenic (conventional) soybean varieties (checks). To this end, studies were conducted at field locations in Brazil which are representative of areas of commercial soybean production and to which all genotypes are adapted.

Five treatments (Table 22) were replicated four times in a completely randomized block design in all field locations. Each plot consisted of six 8 m-long rows with 0.5 m spacing between rows of the same plot and 1.0 m spacing between rows of adjacent plots. Phenotypic and agronomic measurements were determined from plants within the 3$^{rd}$ and 4$^{th}$ rows.

The five treatments included in these evaluations represented a combination of the specific soybean genotypes and herbicide formulations (imidazolinone and non-imidazolinone herbicides) required to generate data appropriate to meeting the objectives of these studies.

Two herbicide treatments were used in these evaluations: 1) imazapyr, sprayed at a rate of 70 g ai/ha, and 2) Volt, a combination of Bentazon (400 g ai/ha) and Acifluorfen (170 g ai/ha), sprayed at a rate of 570 g ai/ha. The different soybean genotypes and herbicide formulations were combined to create five treatments (Table 22). These five treatments (T1, T2, T3, T4, T5) constituted a complete replication in the experimental design.

TABLE 22

Experiment treatments (entries) included in each soybean field trial.

| Treatment | Genotype | Herbicide |
|---|---|---|
| Treatment 1 (T1) | Event 127 | Imazapyr (70 g ai/ha) |
| Treatment 2 (T2) | Event 127 | Volt (570 g ai/ha) |
| Treatment 3 (T3) | Isogenic control | Volt (570 g ai/ha) |
| Treatment 4 (T4) | Monsoy 8001 | Volt (570 g ai/ha) |
| Treatment 5 (T5) | Coodetec 217 (CD 217) | Volt (570 g ai/ha) |

The experiments were planted at seven Experimental Stations in Brazil (Table 23). The stations are located in regions that are representative of areas of soybean production and areas in which the soybean genotypes are adapted. All locations had a Certificate of Quality in Biosafety (CQB), an established infrastructure, laboratory facilities and field equipment, and personnel experienced in agricultural research and trained in biosafety.

TABLE 23

Experimental Station locations with location, experiment, and CQB codes.

| CITY, STATE | LOCATION (EXPERIMENT) CODE |
|---|---|
| Santo Antonio de Posse, SP | EEA (011) |
| Ponta Grossa, PR | SNT (008) |
| Londrina, PR | CNPSO (010) |
| Uberaba, MG | CTTP (012) |
| Brasília, DF | CNPH (016) |
| Santo Antônio de Goiás, GO | CNPAF (014) |
| Sete Lagoas, MG | CNPMS (013) |

The phenotypic, phenologic, and agronomic similarities of event 127, isogenic control, and check varieties was determined by recording various characteristics routinely used to describe the phenotype and behavior of a soybean genotype. The characteristics were recorded for all plots at all locations (unless otherwise noted). Tukey's test was used to compare means of sources of variation determined by ANOVA to have a significant effect on a particular characteristic.

As an average across locations, the performance of Event 127 with imazapyr (T1) or with Volt (T2) and the performance of the isogenic control with imazapyr (T3) were not significantly different for Germination, Final Stand, Green Stem, Lodging, Days to Flower, Days to Maturity, or Yield (Table 24). Only for Plant Height and Seed Size did T1 significantly differ from T3 and only for Seed Size did T2 significantly differ from T3. In addition, none of the differences in trait means locations for T1 and T2 were significantly different (Table 24).

TABLE 24

Treatment means over location for each evaluated trait.

| Treatment[‡] | Trait[†] | | | | | | | | |
|---|---|---|---|---|---|---|---|---|---|
| | G | FS | PH | GS | L | DF | DM | 100SW | Yield |
| T1 | 85.0 a[§] | 90.7 a | 79.0 bc | 4.5 a | 1.5 ab | 45 a | 126 a | 19.7 a | 3748 a |
| T2 | 85.8 a | 90.5 a | 83.4 ab | 2.0 a | 1.6 ab | 45 a | 126 a | 18.8 a | 3816 a |
| T3 | 88.3 a | 94.6 a | 86.0 a | 1.1 a | 1.9 a | 45 a | 125 ab | 16.9 b | 3463 a |
| T4 | 87.9 a | 93.5 a | 79.0 bc | 1.6 a | 1.1 b | 45 a | 122 c | 13.2 c | 3502 a |
| T5 | 85.9 a | 91.4 a | 74.7 c | 0.9 a | 2.1 a | 46 a | 122 bc | 13.5 c | 3570 a |

[†]G = initial germination (%); FS = final plant stand; PH = plant height (cm); GS = green stem (%); L = degree of lodging; DF = days to full flower (vegetative cycle); DM = days to full maturity (total cycle); 100SW = seed size (weight of 100 seeds (g)); and Yield = grain yield (kg/ha).
[‡]T1 = BPS-CV-127-9 treated with imazapyr, T2 = BPS-CV-127-9 treated with Volt, T3 = Isoline Control treated with Volt, T4 = Monsoy 8001 treated with Volt, T5 = Coodetec 217 treated with Volt.
[§]Means followed by the same letter do not differ significantly by the Tukey test at 5% probability.

The results of this study indicate that soybean lines containing event 127 can be used to maintain levels of yield after application of imidazolinone herbicides having residual activity that are equivalent to other commercial varieties in the absence of such herbicide application.

Example 5

Gel-based PCR Assay for Qualitative Event-Specific Detection

A qualitative gel-based PCR assay method was developed for use in the detection of event-127 nucleic acids in seed and grain samples. The method was capable of detecting 0.05% event-127 soybean DNA in a mixture of non-transgenic soybean DNA.

Grain and seed samples were ground in a 25 ml grinding beaker for 30 seconds at 30 Hz using a mixer mill MM 400 (Retsch; Haan, Germany) to yield a homogenous powder. Genomic DNA was extracted from 0.1-1 g ground grain samples using CTAB (Cetyl trimethyl ammonium bromide) buffer followed by chloroform:octanol extraction and alcohol precipitation. The resulting precipitate was dissolved and the remaining inhibitors were removed by anion-exchange chromatography using a Genomic-tip 20/G gravity-flow column (Qiagen; Hilden, Germany).

The concentration and purity of the DNA was assayed with the spectrophotometer Nanodrop ND-1000 (Peqlab Biotechnologie; Erlangen, Germany) by determining the ratio of sample light absorbance at wavelengths of 260 and 280 nm ($A_{260/280}$) and at 260 and 230 nm ($A_{260/230}$). DNA having $A_{260/280}$ ratios close to 1.8 and $A_{260/230}$ higher than 1.8 were selected for subsequent PCR.

Another set of primers were developed to amplify an event 127 specific region and a soybean-specific gene was used as an endogenous control. The event-specific PCR assay targets the transgene insert-native soybean genomic DNA junction unique to event 127. All PCR amplifications were performed in a T1 Thermal Cycler (Biometra; Gottingen, Germany). One hundred nanograms of genomic DNA were used as template in each of the PCR reactions.

A soybean-specific PCR system to detect the *Glycine max* (soybean) lectin gene (Le 1), (GenBank Accession No. K00821) was used as the reference system. The primer sequences and the PCR cycling conditions for the lectin gene PCR were adapted from Hird et al. (J. AOAC Int., 86: 66-71 (2003)). The primer sequences were SoyLec-F (5'-TGGTCGCGCCCTCTACTC) (SEQ ID NO: 65) and SoyLec-R (5'-GGCGAAGCTGGCAACG) (SEQ ID NO: 66). The primers were designed to amplify a fragment specific to soybean of 70 base-pairs (bp).

PCRs for the endogenous controls were performed in 20 μl total volume with 100 ng of genomic DNA, 200 μM of dNTP, 2 mM MgCl$_2$, 500 nM of each primer and 1 unit Taq DNA polymerase per reaction. After an initial 2 min denaturation at 94° C., 32 cycles of 94° C. for 30 sec, 60° C. for 30 sec, and 72° C. for 30 sec were performed, followed by a final 1 min extension at 72° C.

Reactions using the above primers and conditions were conducted with individual DNA samples obtained from rice (*Oryza sativa*), rapeseed (*Brassica napus*), cotton (*Gossypium hirsutum*, 2 different lines), maize (*Zea mays*), soybean Conquista, soybean event 127, and no DNA template (as a control) and run on an agarose gel. A 70-basepair product was obtained in DNA samples from soybean plants (Conquista and event 127), while no amplification product was obtained in the other samples. Thus, the endogenous control primers are capable of detecting genomic DNA from soybean specifically.

The event-specific assay for event 127 soybean was established at the 5' insert-to-genomic soybean DNA junction. The forward primer-binding site is located within native genomic soybean DNA (127-61F: 5'-GGGCAAACTAGT CTCGTAATATAT) (SEQ ID NO: 67) and the binding site of the reverse primer is located in the 127 insert (127-176R: 5'-CGGAATTGGTAATCGAAATT) (SEQ ID NO: 68). The reaction amplifies a fragment of 116 base pairs (bp).

The specificity of the event specific primers (127-61F and 127-176R) was determined using 100 ng genomic DNA (from rice (*Oryza sativa*), rapeseed (*Brassica napus*), cotton (*Gossypium hirsutum*), maize (*Zea mays*), Soybean GTS 40-3-2, Soybean 305423, Soybean 356043, Soybean A2704-

12, Soybean Conquista, Soybean event 127, and a no template control). PCR for the event specific reactions was performed in 20 μl total volume with 100 ng of the template DNA, 200 μM of dNTP, 2 mM MgCl$_2$, 500 nM of each primer and 1 unit Taq DNA polymerase per reaction. After an initial 2 min denaturation at 94° C., 32 cycles of 94° C. for 30 sec, 56° C. for 30 sec, and 72° C. for 30 sec were performed, followed by a final 1 min extension at 72° C.

The absence or presence of soybean event 127 in the samples was determined by separation of amplified event 127-specific 116 bp PCR fragments in an ethidium bromide-stained 4% agarose gel.

An event 127-specific 116 bp PCR fragment was obtained in all reactions corresponding to soybean event 127 samples, while no 127-specific PCR fragment was obtained in any of the other samples. Thus, the event specific primers 127-61F and 127-176R are capable of specifically detecting DNA from event 127 soybean plants. A nucleotide sequence search using the amplified event-specific amplicon sequence did not identify any 100% identical match using a DNA-DNA Basic Local Alignment Search Tool (BLASTN) analysis.

In order to determine the limit of detection of reactions using the 127-61 F and 127-176R primers, standards containing defined event 127 DNA content (100%, 1%, 0.5%, 0.1%, 0.05%, and 0%) were produced by subsequent dilutions of event 127 DNA with Conquista DNA. At each dilution, 22 replicated PCR amplifications were performed using the conditions discussed above. One no-DNA template control (NTC) per system was run to verify the purity of the reagents.

Event 127-specific PCR products (116 bp fragment) were detected in all dilutions tested in a range from 0.05% to 100% event 127 DNA. As expected, no event 127-specific bands were detected in non-transgenic soybean samples or no-template controls (NTC) even though all non-transgenic soybean samples were shown to have amplifiable DNA by the presence of the expected amplicon in a soybean-specific PCR amplification. The lowest amount of event 127 DNA in a sample that can be detected reliably using the 127-61F and 127-176R primers is 0.05%.

The event-specific PCR using 127-61F and 127-176R primers demonstrate a relative LOD of <0.1% with 95% confidence. In addition, the 127-61F and 127-176R primers do not amplify any detectable PCR products in the 0% event 127 reference (100% non-transgenic soybean) or no-template control reactions.

In order to assess the influence of varying the annealing temperature in the PCR reactions, four samples (0%, 0.05%, 1%, and 100% of event 127 soybean DNA diluted in a non-transgenic Conquista soybean DNA background) were analyzed in triplicate in experiments with annealing temperatures of 54° C. and 58° C. The results demonstrate that annealing temperatures deviating from the optimal annealing temperature by ±2° C. result in 100% correct detection of event 127-specific DNA.

In order to assess the influence of different PCR platforms, three samples (0.05%, 1%, and 100% event 127 soybean DNA diluted in a non-transgenic Conquista soybean DNA background) were analyzed in triplicate using an ABI 7500 Fast Real-Time PCR System (Applied Biosystems; Darmstadt, Germany). A 0% event 127 sample (100% Conquista DNA) and a sample without DNA-template were included as controls.

The results demonstrate good performance of the event 127-specific PCR assay using 127-61F and 127-176R primers in different PCR instruments. The relative limit of detection was 0.05% in all three reactions. As expected, no PCR products were detected in samples containing 0% event 127 DNA in a non-transgenic soybean DNA background or in no-template controls.

In order to assess the reproducibility of the assay between laboratories (inter-laboratory transferability), two independent experiments were performed in a separate laboratory. Different samples containing from 0.05% to 100% event 127 DNA content in a non-transgenic soybean DNA background were analyzed in duplicate in two independent experiments using 100 ng genomic DNA per reaction on a DNA Engine Dyad thermal cycler (BioRad; München, Germany). The results indicate good reproducibility of the assay between laboratories (inter-laboratory transferability). The results demonstrated 100% positive results with 100%, 1%, and 0.5% event 127 DNA samples. In addition, at least 95% positive results were obtained with 0.1% and 0.05% event 127 DNA samples (assuming that relative LOD<0.05%), and no positive results were obtained in 0% event 127 DNA samples or no-template controls.

The qualitative event-specific, gel-based PCR detection method using the 127-61F and 127-176R primers is capable of detecting the event 127-specific target sequence in a mixture of 0.05% event 127 DNA in a non-transgenic soybean DNA background. None of the samples containing only non-transgenic soybean DNA or other transgenic events produced a detectable event 127-specific PCR product, thereby experimentally demonstrating the specificity of the method.

Example 6

Increased Plant Health Using Soybean Event 127 with Combinations of Imidazolinones and Strobilurins Soybean event 127 plants were treated with (1) an imidazolinone herbicide or herbicides, (2) a strobilurin fungicide, and (3) a combination of an imidazolinone herbicide or herbicides along with a strobilurin fungicide.

Soybean event 127 plants were grown in 25 cm diameter pots with 5 plants/pot. The various applications of the herbicide(s) and/or fungicide (described below in Table X) took place 23 days post-seeding for treatments 1-16 and took place 24 days post-seeding for treatments 17-32.

TABLE 25

| Treatment No. | Actives in treatment | Active ingredient application rate (grams active ingredient/hectare) |
|---|---|---|
| 1 | None (control) | |
| 2 | pyraclostrobin | 50 g a/ha |
| 3 | pyraclostrobin | 75 g a/ha |
| 4 | pyraclostrobin | 150 g a/ha |
| 5 | imazapyr | 36 g/ha |
| 6 | imazapyr | 72 g a/ha |
| 7 | imazapyr | 144 g a/ha |
| 8 | imazapyr<br>pyraclostrobin | 36 g a/ha<br>50 g a/ha |
| 9 | imazapyr<br>pyraclostrobin | 36 g a/ha<br>75 g a/ha |
| 10 | imazapyr<br>pyraclostrobin | 36 g a/ha<br>150 g a/ha |
| 11 | imazapyr<br>pyraclostrobin | 72 g a/ha<br>50 g a/ha |
| 12 | imazapyr<br>pyraclostrobin | 72 g a/ha<br>75 g a/ha |
| 13 | imazapyr<br>pyraclostrobin | 72 g a/ha<br>150 g a/ha |
| 14 | imazapyr<br>pyraclostrobin | 144 g a/ha<br>150 g a/ha |

TABLE 25-continued

| Treatment No. | Actives in treatment | Active ingredient application rate (grams active ingredient/hectare) |
|---|---|---|
| 15 | imazapyr | 144 g a/ha |
|    | pyraclostrobin | 75 g a/ha |
| 16 | imazapyr | 144 g a/ha |
|    | pyraclostrobin | 150 g a/ha |
| 17 | None (control) | |
| 18 | pyraclostrobin | 50 g a/ha |
| 19 | pyraclostrobin | 75 g a/ha |
| 20 | pyraclostrobin | 150 g a/ha |
| 21 | imazapic + imazapyr (1:3 by weight) | 35 g a/ha |
| 22 | imazapic + imazapyr (1:3 by weight) | 70 g a/ha |
| 23 | imazapic + imazapyr (1:3 by weight) | 140 g a/ha |
| 24 | imazapic + imazapyr (1:3 by weight) | 35 g a/ha |
|    | pyraclostrobin | 50 g a/ha |
| 25 | imazapic + imazapyr (1:3 by weight) | 35 g a/ha |
|    | pyraclostrobin | 75 g a/ha |
| 26 | imazapic + imazapyr (1:3 by weight) | 35 g a/ha |
|    | pyraclostrobin | 150 g a/ha |
| 27 | imazapic + imazapyr (1:3 by weight) | 70 g a/ha |
|    | pyraclostrobin | 50 g a/ha |
| 28 | imazapic + imazapyr (1:3 by weight) | 70 g a/ha |
|    | pyraclostrobin | 75 g a/ha |
| 29 | imazapic + imazapyr (1:3 by weight) | 75 g a/ha |
|    | pyraclostrobin | 150 g a/ha |
| 30 | imazapic + imazapyr (1:3 by weight) | 140 g a/ha |
|    | pyraclostrobin | 50 g a/ha |
| 31 | imazapic + imazapyr (1:3 by weight) | 140 g a/ha |
|    | pyraclostrobin | 75 g a/ha |
| 32 | imazapic + imazapyr (1:3 by weight) | 140 g a/ha |
|    | pyraclostrobin | 150 g a/ha |

At 1, 7, and 14 days after application (DAA), the plants were assessed for phytotoxicity, vigor, plant height, relative photosynthesis, relative SPAD (i.e., a relative measure of leaf chlorophyll/greenness), and stomatal conductance.

As shown in Table 26 below, the addition of pyraclostrobin to treatments with imazapic or with imazapic plus imazapyr noticeably increased the net photosynthesis, increased overall plant greening (relative SPAD), and increased stomatal conductance relative to certain treatments without the pyraclostrobin at certain time points.

TABLE 26

| | Treatment without Pyraclostrobin (relative %) | Comparative Treatment with Pyraclostrobin (relative %) |
|---|---|---|
| RELATIVE PHOTOSYNTHESIS | | |
| 1 DAA | 22 (38.5%) | 27 (63.9%) |
|       | 23 (44.1%) | 30 (69.3%) |
| 7 DAA | 7 (74.7%)  | 14 (93.1%) |
|       | 23 (69.9%) | 31 (85.8%) |
|       |            | 32 (86.1%) |
| 14 DAA | 7 (85.1%) | 14 (97.5%) |
| RELATIVE SPAD | | |
| 1 DAA | 5 (89.6%) | 9 (103.5%) |
|       |           | 10 (106.1%) |
|       | 6 (89.4%) | 11 (103.7%) |
|       |           | 12 (109.5%) |
|       | 7 (98.5%) | 14 (108.6%) |
|       |           | 16 (124.8%) |
|       | 21 (78.1%) | 24 (104.3%) |
|       |            | 25 (83.5%) |
|       |            | 26 (81.7%) |
|       | 22 (74.9%) | 27 (92.2%) |
|       |            | 28 (86.5%) |
|       |            | 29 (91.9%) |
| 14 DAA | 6 (66.9%) | 11 (76.2%) |
|        |           | 12 (72.5%) |
|        |           | 13 (87.3%) |
|        | 21 (77.9%) | 24 (84.9%) |
|        |            | 25 (89.4%) |
|        | 23 (87.9%) | 31 (97.3%) |
|        |            | 32 (87.9%) |
| RELATIVE STOMATAL CONDUCTANCE | | |
| 1 DAA | 23 (42.6%) | 30 (109.3%) |
|       |            | 31 (86.9%) |
|       |            | 32 (58.2%) |
| 7 DAA | 7 (2.8%)   | 14 (31.3%) |
|       |            | 15 (68.4%) |
|       |            | 16 (38%) |
| 14 DAA | 7 (102.3%) | 14 (104.5%) |
|        |            | 15 (103.5%) |
|        |            | 16 (103.2%) |

This indicates that the combination of pyraclostrobin with an AHAS-inhibiting herbicide (or herbicides) provides a surprising degree of benefit to event 127 soy plants.

What is claimed is:

1. A method for controlling weeds in a cultivated area, comprising:
applying an effective amount of an herbicidal composition comprising an AHAS-inhibiting herbicide to the cultivated area having a soybean plant comprising an event 127 nucleic acid molecule, a representative sample of seeds comprising the event 127 nucleic acid molecule having been deposited as NCIMB Patent Deposit No. 41603.

2. The method of claim 1, wherein the event 127 nucleic acid molecule comprises an event 127 specific nucleic acid molecule.

3. The method of claim 1, wherein the event 127 nucleic acid molecule comprises the nucleic acid sequence of SEQ ID NO:1.

4. The method of claim 1, wherein the herbicidal composition comprises one of more of imidazolinone herbicides, other AHAS-inhibiting herbicides, EPSPS-inhibiting herbicides, GS-inhibiting herbicides, PPO-inhibiting herbicides, auxinic herbicides, and combinations thereof.

5. The method of claim 4, wherein the herbicidal composition comprises imazapyr, imazapic, or a combination thereof.

6. The method of claim 1, wherein the weeds are resistant to glyphosate.

7. A method for controlling glyphosate tolerant weeds in a crop field, comprising:
applying an effective amount of an herbicidal composition comprising an AHAS-inhibiting herbicide to the crop field having a soybean plant comprising an event 127 nucleic acid molecule, a representative sample of seeds comprising the event 127 nucleic acid molecule having been deposited as NCIMB Patent Deposit No. 41603.

8. The method of claim 7, wherein the soybean plant comprises a nucleic acid molecule having the nucleic acid sequence of SEQ ID NO:1.

9. The method of claim 7, wherein the event 127 nucleic acid molecule comprises an event 127 specific nucleic acid molecule.

10. The method of claim 7, wherein the herbicidal composition comprises imazapyr or imazapic, or a combination thereof.

11. An isolated nucleic acid molecule comprising the nucleic acid sequence of positions 1312 to 6069 of SEQ ID NO:1.

12. The isolated nucleic acid molecule of claim 11, wherein the nucleic acid molecule is in a recombinant nucleic acid construct.

13. A soybean plant comprising the isolated nucleic acid molecule of claim 11.

14. A transgenic soybean plant comprising a heterologous nucleic acid molecule comprising the nucleic acid sequence of nucleotides 1302 to 6079 of SEQ ID NO:1.

15. The transgenic soybean plant of claim 14, wherein the soybean plant is resistant to an AHAS-inhibiting herbicide.

16. A method for increasing yield in a soybean plant comprising an event 127 nucleic acid molecule in a cultivated area, the method comprising:
   applying an effective amount of an herbicidal composition comprising an AHAS-inhibiting herbicide to one or more soybean plants comprising an event 127 nucleic acid molecule and the cultivated area, wherein the herbicidal composition reduces weed growth in the cultivated area; and
   harvesting seed from the one or more soybean plants, a representative sample of seeds comprising the event 127 nucleic acid molecule having been deposited as NCIMB Patent Deposit No. 41603.

17. A seed of a transgenic soybean plant comprising an event 127 nucleic acid molecule, a representative sample of seeds comprising the event 127 nucleic acid molecule having been deposited as NCIMB Patent Deposit No. 41603.

18. The seed of claim 17, wherein the event 127 nucleic acid molecule comprises the nucleic acid sequence of SEQ ID NO:1.

19. The seed of claim 18, wherein the seed is of a plant of, or is of a plant that is progeny of, line 'BPS-CV127-9'.

20. A transgenic soybean plant, or part thereof, produced by growing the seed of claim 17.

21. A method for growing a transgenic soybean plant, comprising:
   (A) providing a soybean seed comprising an event 127 nucleic acid molecule, a representative sample of seeds comprising the event 127 nucleic acid molecule having been deposited as NCIMB Patent Deposit No. 41603;
   (B) planting the soybean seed in a growth medium under conditions that allow the seed to germinate to produce a growing soybean plant comprising an event 127 nucleic acid molecule; and
   (C) contacting the growth medium, seed, or plant with an herbicidal composition comprising at least one component selected from the group consisting of imidazolinone herbicides, sulfonylurea herbicides, combinations thereof with one another, and combinations thereof with at least one other active ingredient.

22. The method of claim 21, wherein step (C) is performed before step (B) and comprises contacting the growth medium with the herbicidal composition.

23. The method of claim 21, wherein step (C) is performed after step (B) and comprises contacting the plant or growth medium after the plant has emerged from the growth medium.

24. The method of claim 21, wherein the herbicidal composition comprises a combination of (1) at least one imidazolinone herbicide, or at least one sulfamide herbicide, or both, with (2) at least one other active ingredient that is selected from the group consisting of fungicides, bacteriacides, organophosphate herbicides, sulfamide herbicides, benzothiadiazinone herbicides, and combinations thereof.

25. The method of claim 12, wherein the herbicidal composition comprises imazapyr, imazapic, or any one of the following combinations of:
   (A) imazapyr and imazapic;
   (B) imazapyr, imazapic, and bentazon;
   (C) imazapyr, imazapic, and pyraclostrobin;
   (D) imazapyr, imazapic, and saflufenacil;
   (E) imazapyr, imazapic, saflufenacil, and glyphosate;
   (F) imazaypr and bentazon;
   (G) imazapyr and pyraclostrobin;
   (H) imazapyr and saflufenacil;
   (I) imazapyr, saflufenacil, and glyphosate;
   (J) imazapyr and glyphosate;
   (K) imazapic and glyphosate; or
   (L) imazapic, saflufenacil, and glyphosate.

26. The method of claim 21, wherein the event 127 nucleic acid molecule has the nucleic acid sequence of nucleotides 1302 to 6069 of SEQ ID NO:1.

27. The method of claim 1, wherein the method further comprises applying a strobilurin to the cultivated area.

28. The method of claim 27, wherein strobilurin comprises pyraclostrobin.

29. The method of claim 7, wherein the method further comprises applying a strobilurin to the cultivated area.

30. The method of claim 3, wherein the herbicidal composition
   (A) comprises:
   imazapyr;
   imazapic;
   or any one of the following:
   a combination of imazapyr and imazapic;
   a combination of imazapyr, imazapic, and bentazon;
   a combination of imazapyr, imazapic, and pyraclostrobin;
   a combination of imazapyr, imazapic, and saflufenacil;
   a combination of imazapyr, imazapic, saflufenacil, and glyphosate;
   a combination of imazaypr and bentazon;
   a combination of imazapyr and pyraclostrobin;
   a combination of imazapyr and saflufenacil;
   a combination of imazapyr, saflufenacil, and glyphosate;
   a combination of imazapyr and glyphosate;
   a combination of imazapic and glyphosate; and
   a combination of imazapic, saflufenacil, and glyphosate; or
   (B) further comprises a combination of saflufenacil and glyphosate.

31. The method of claim 4, wherein the EPSPS-inhibiting herbicide comprises glyphosate and the PPO-inhibiting herbicide comprises saflufenacil.

32. The method of claim 16, wherein the herbicidal composition comprises imazapyr, imazapic, or a combination thereof.

33. The seed of claim 17, wherein the seed is treated with an herbicidal composition comprising an AHAS-inhibiting herbicide or a combination of AHAS-inhibiting herbicides.

34. The seed of claim 33, wherein the herbicidal composition comprises imazapyr, imazapic, or a combination thereof.

35. A method of controlling weeds in a cultivated area, comprising:

planting the seed of claim 33 in the cultivated area.

\* \* \* \* \*